US011185582B2

(12) United States Patent
Gardner et al.

(10) Patent No.: US 11,185,582 B2
(45) Date of Patent: Nov. 30, 2021

(54) BROADLY NEUTRALIZING ANTI-HUMAN CYTOMEGALOVIRUS (HCMV) ANTIBODIES AND METHODS OF USE THEREOF

(71) Applicant: Icahn School of Medicine at Mount Sinai, New York, NY (US)

(72) Inventors: Thomas Gardner, New York, NY (US); Thomas Moran, New York, NY (US); Domenico Tortorella, New York, NY (US)

(73) Assignee: ICAHN SCHOOL OF MEDICINE AT MOUNT SINAI, New York, NY (US)

( * ) Notice: Subject to any disclaimer, the term of this patent is extended or adjusted under 35 U.S.C. 154(b) by 0 days.

(21) Appl. No.: 16/099,524

(22) PCT Filed: May 9, 2017

(86) PCT No.: PCT/US2017/031718
§ 371 (c)(1),
(2) Date: Nov. 7, 2018

(87) PCT Pub. No.: WO2017/196819
PCT Pub. Date: Nov. 16, 2017

(65) Prior Publication Data
US 2020/0330588 A1 Oct. 22, 2020

Related U.S. Application Data

(60) Provisional application No. 62/334,270, filed on May 10, 2016, provisional application No. 62/333,671, filed on May 9, 2016.

(51) Int. Cl.
| | | |
|---|---|---|
| *A61K 39/25* | (2006.01) | |
| *A61P 31/20* | (2006.01) | |
| *C07K 16/08* | (2006.01) | |
| *C12N 15/63* | (2006.01) | |
| *G01N 33/569* | (2006.01) | |
| *A61K 39/39* | (2006.01) | |
| *A61K 45/06* | (2006.01) | |
| *A61K 39/00* | (2006.01) | |

(52) U.S. Cl.
CPC .............. *A61K 39/25* (2013.01); *A61P 31/20* (2018.01); *C07K 16/088* (2013.01); *C12N 15/63* (2013.01); *G01N 33/56966* (2013.01); *A61K 39/39* (2013.01); *A61K 45/06* (2013.01); *A61K 2039/505* (2013.01)

(58) Field of Classification Search
CPC ........ A61K 39/25; A61K 39/39; A61K 45/06; A61K 2039/505; A61P 31/20; C07K 16/088; C07K 2317/33; C07K 2317/76; C07K 16/34; C07K 16/44; C12N 15/63; G01N 33/56966
See application file for complete search history.

(56) References Cited

U.S. PATENT DOCUMENTS

| | | |
|---|---|---|
| 2004/0005647 A1 | 1/2004 | Denardo et al. |
| 2004/0082033 A1 | 4/2004 | Smith et al. |
| 2006/0269550 A1 | 11/2006 | Heiman |
| 2009/0060920 A1 | 3/2009 | Witcher et al. |
| 2011/0027270 A1 | 2/2011 | Garcia-Sastre et al. |
| 2011/0123536 A1 | 5/2011 | Chermann et al. |
| 2013/0202608 A1 | 8/2013 | Mookkan et al. |
| 2013/0224191 A1 | 8/2013 | Stull et al. |
| 2014/0193428 A1 | 7/2014 | Lanzavecchia et al. |

FOREIGN PATENT DOCUMENTS

WO 2014/200898 A2 12/2014

OTHER PUBLICATIONS

Klein M, Schoppel K, Amvrossiadis N, Mach M. Strain-specific neutralization of human cytomegalovirus isolates by human sera. J Virol. Feb. 1999;73(2):878-86. (Year: 1999).*
Urban M, Britt W, Mach M. The dominant linear neutralizing antibody-binding site of glycoprotein gp86 of human cytomegalovirus is strain specific. J Virol. Mar. 1992;66(3):1303-11. (Year: 1992).*
Martí-Carreras J, Maes P. Human cytomegalovirus genomics and transcriptomics through the lens of next-generation sequencing: revision and future challenges. Virus Genes. Apr. 2019;55(2):138-164. Epub Jan. 2, 2019. (Year: 2019).*
Bowie JU, Reidhaar-Olson JF, Lim WA, Sauer RT. Deciphering the message in protein sequences: tolerance to amino acid substitutions. Science. Mar. 16, 1990;247(4948):1306-10. (Year: 1990).*
Winkler K, Kramer A, Küttner G, Seifert M, Scholz C, Wessner H, Schneider-Mergener J, Höhne W. Changing the antigen binding specificity by single point mutations of an anti-p24 (HIV-1) antibody. J Immunol. Oct. 15, 2000;165(8):4505-14. (Year: 2000).*
Kussie PH, Parhami-Seren B, Wysocki LJ, Margolies MN. A single engineered amino acid substitution changes antibody fine specificity. J Immunol. Jan. 1, 1994;152(1):146-52. (Year: 1994).*
Chen Z, Wang J, Bao L, Guo L, Zhang W, Xue Y, Zhou H, Xiao Y, Wang J, Wu F, Deng Y, Qin C, Jin Q. Human monoclonal antibodies targeting the haemagglutinin glycoprotein can neutralize H7N9 influenza virus. NatCommun. Mar. 30, 2015;6:6714. (Year: 2015).*
Sela-Culang I, Kunik V, Ofran Y. The structural basis of antibody-antigen recognition. Front Immunol. Oct. 8, 2013;4:302. (Year: 2013).*
Sirin S, Apgar JR, Bennett EM, Keating AE. AB-Bind: Antibody binding mutational database for computational affinity predictions. Protein Sci. Feb. 2016;25(2):393-409. Epub Nov. 6, 2015. (Year: 2015).*
Tsuchiya Y, Mizuguchi K. The diversity of H3 loops determines the antigen-binding tendencies of antibody CDR loops. Protein Sci. Apr. 2016;25(4):815-25. Epub Jan. 20, 2016. (Year: 2016).*

(Continued)

*Primary Examiner* — Rachel B Gill
(74) *Attorney, Agent, or Firm* — Fox Rothschild, LLP

(57) ABSTRACT

The present disclosure relates to anti-human cytomegalovirus (anti-HCMV) antibodies and vaccines as well as diagnostic and therapeutic methods of use.

Figure 1A:
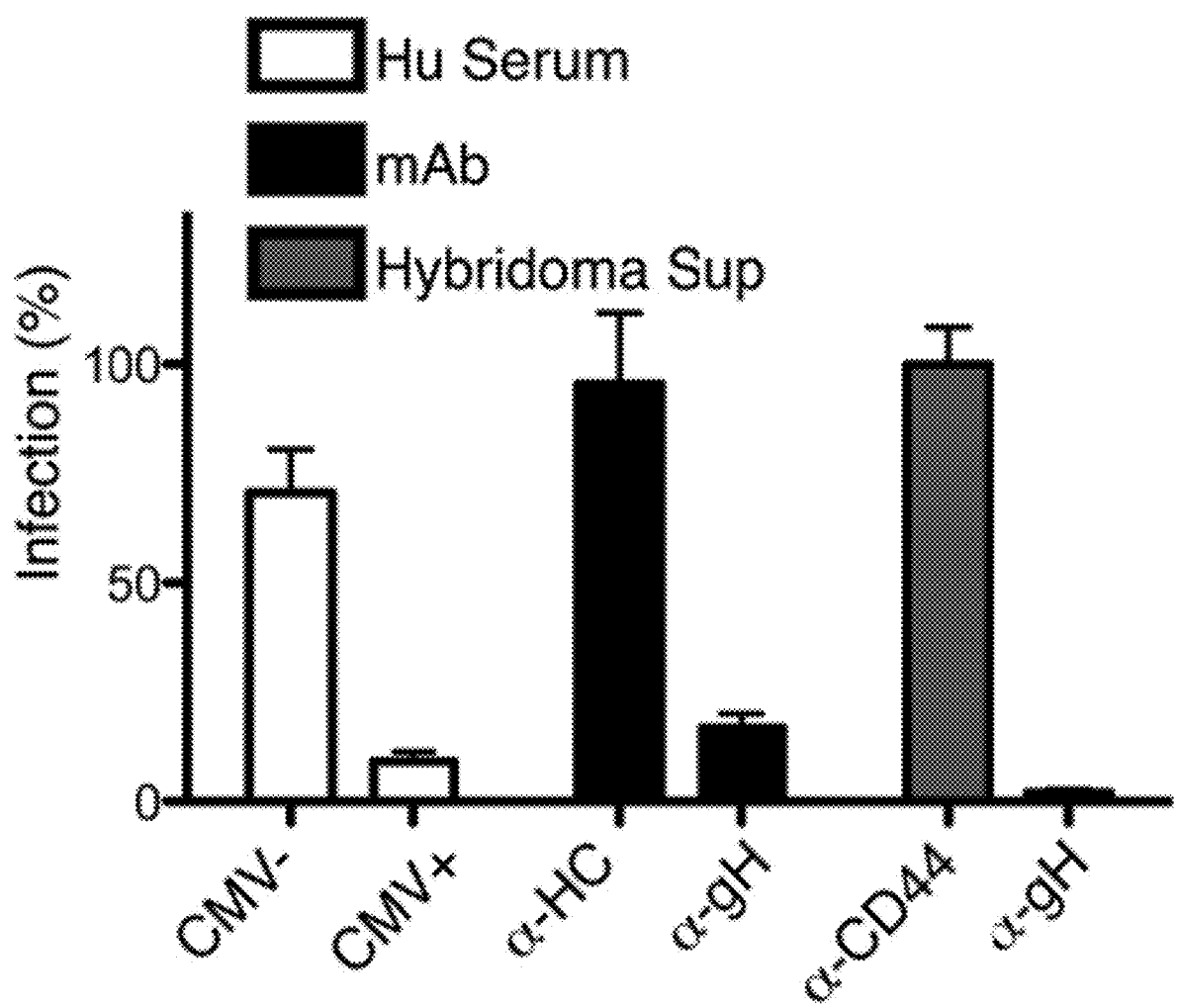

23 Claims, 38 Drawing Sheets
Specification includes a Sequence Listing.

(56) References Cited

OTHER PUBLICATIONS

Collis AV, Brouwer AP, Martin AC. Analysis of the antigen combining site: correlations between length and sequence composition of the hypervariable loops and the nature of the antigen. J Mol Biol. Jan. 10, 2003;325(2):337-54. (Year: 2003).*

Dondelinger M, Filee P, Sauvage E, Quinting B, Muyldermans S, Galleni M, Vandevenne MS. Understanding the Significance and Implications of Antibody Numbering and Antigen-Binding Surface/Residue Definition. Front Immunol. Oct. 16, 2018;9:2278. (Year: 2018).*

Ishibashi K, Tokumoto T, Tanabe K, Shirakawa H, Hashimoto K, Kushida N, Yanagida T, Inoue N, Yamaguchi O, Toma H, Suzutani T. 2007. Association of the outcome of renal transplantation with antibody response to cytomegalovirus strain-specific glycoprotein H epitopes. Clin Infect Dis 45:60-67. (Year: 2007).*

Fouts AE, Comps-Agrar L, Stengel KF, Ellerman D, Schoeffler aj, Warming S, Eaton DL, Feierbach B. 2014. Mechanism for neutralizing activity by the anti-CMV gH/gL monoclonal antibody MSL-109. Proc Natl Acad Sci U S A 111:8209-8214. (Year: 2014).*

Gardner TJ, Tortorella D. Virion Glycoprotein-Mediated Immune Evasion by Human Cytomegalovirus: a Sticky Virus Makes a Slick Getaway. Microbiol Mol Biol Rev. Jun. 15, 2016;80(3):663-77. (Year: 2016).*

Schultz et al., "Scanning Mutagenesis of Human Cytomegalovirus Glycoprotein gH/gL", Journal of Virology, vol. 90, No. 5, Mar. 2016, pp. 2294-2305.

Simpson et al., "Neutralizing monoclonal antibodies that distinguish three antigenic sites on human cytomegalovirus glycoprotein H have conformationally distinct binding sites", Journal of Virology, Jan. 1993, pp. 489-496.

Nejatollahi et al., "Neutralising human recombinant antibodies to human cytomegalovirus glycoproteins gB and gH", Fems Immunology and Medical Microbiology, Elsevier Science B.V., vol. 34, No. 3, Nov. 2002, pp. 237-244.

Ohta et al., "Recombinant human monoclonal antibodies to human cytomegalovirus glycoprotein B neutralize virus in a complement-dependent manner", Microbes and Infection, Elsevier, vol. 11, No. 13, Nov. 2009, pp. 1029-1036.

Gerna et al., "Human cytomegalovirus serum neutralizing antibodies block virus infection of endothelial/epithelial cells, but not fibroblasts, early during primary infection", Journal of General Virology, Society for General Microbiology, vol. 89, Jan. 2008, pp. 853-865.

Gardner et al., "Development of a High-Throughput Assay to Measure the Meutralization Capability of Anti-Cytomegalovirus Antibodies", Clinical and Diagnostic Laboratory Immunology, vol. 20, No. 4, Apr. 2013, pp. 540-550.

Gardner et al., "Human cytomegalovirus gH stability and trafficking are regulated by ER-associated degradation and transmembrane architecture", Scientific Reports, vol. 6, No. 1, Mar. 2016.

Gardner et al., "Functional screening for anti-CMV biologics identifies a broadly neutralizing epitope of an essential envelope protein", Nature Communications, vol. 7, No. 1, Dec. 2016.

Foroogh et al., "Neutralising human recombinant antibodies to human cytomegalovirus glycoproteins gB and gH", FEMS Immunology and Medical Microbiology, vol. 34, No. 3, Nov. 2002, pp. 237-244.

Ohta et al., "Recombinant human monoclonal antibodies to human cytomegalovirus glycoprotein B neutralize virus in a complement-dependent manner", Microbes and Infection, vol. 11, No. 13, Nov. 2009, pp. 1029-1036 (Abstract only).

Extended European Search Report dated Mar. 24, 2020 issued in the corresponding European Patent Application No. 17796674.4.

* cited by examiner

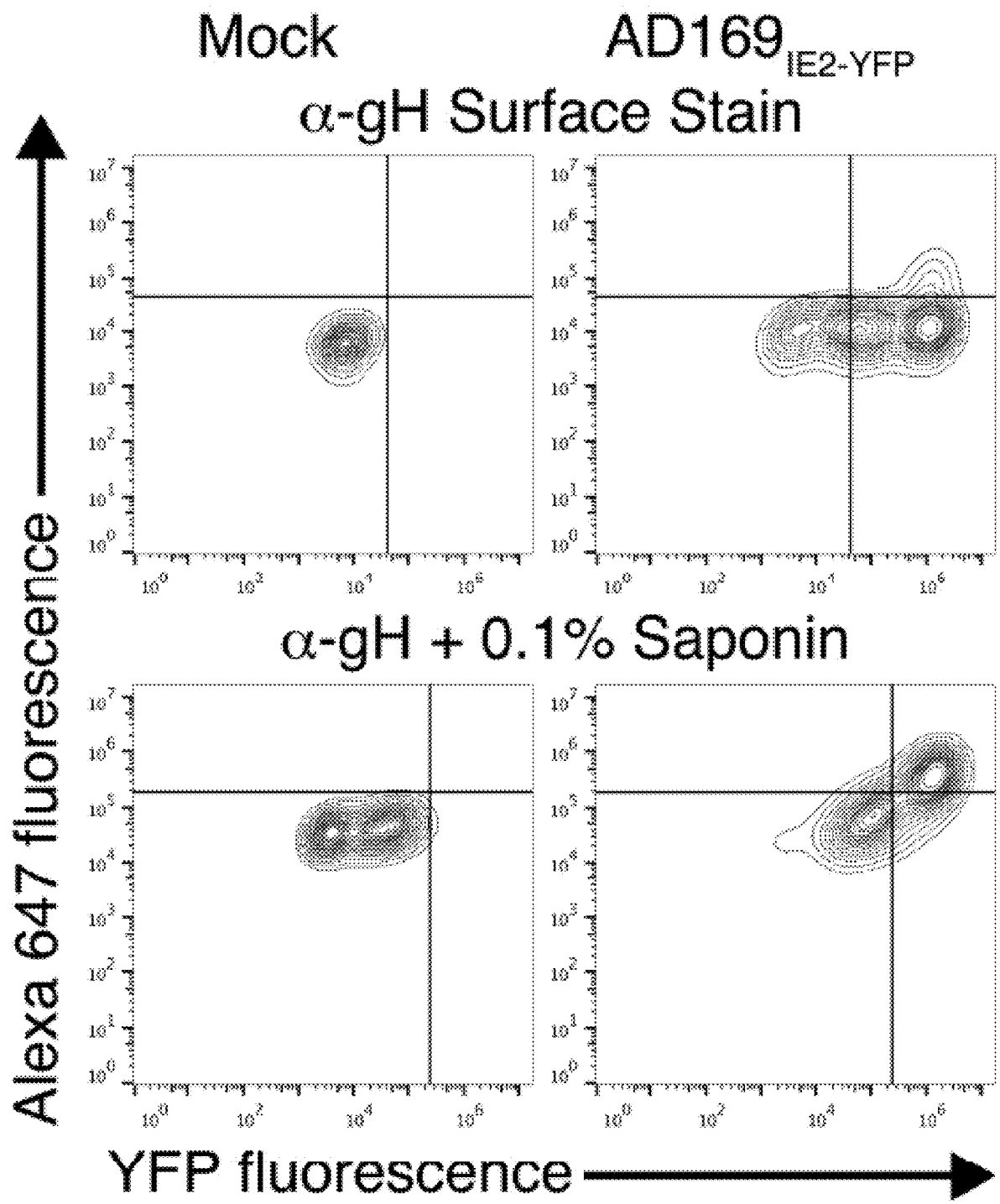

Cytogam

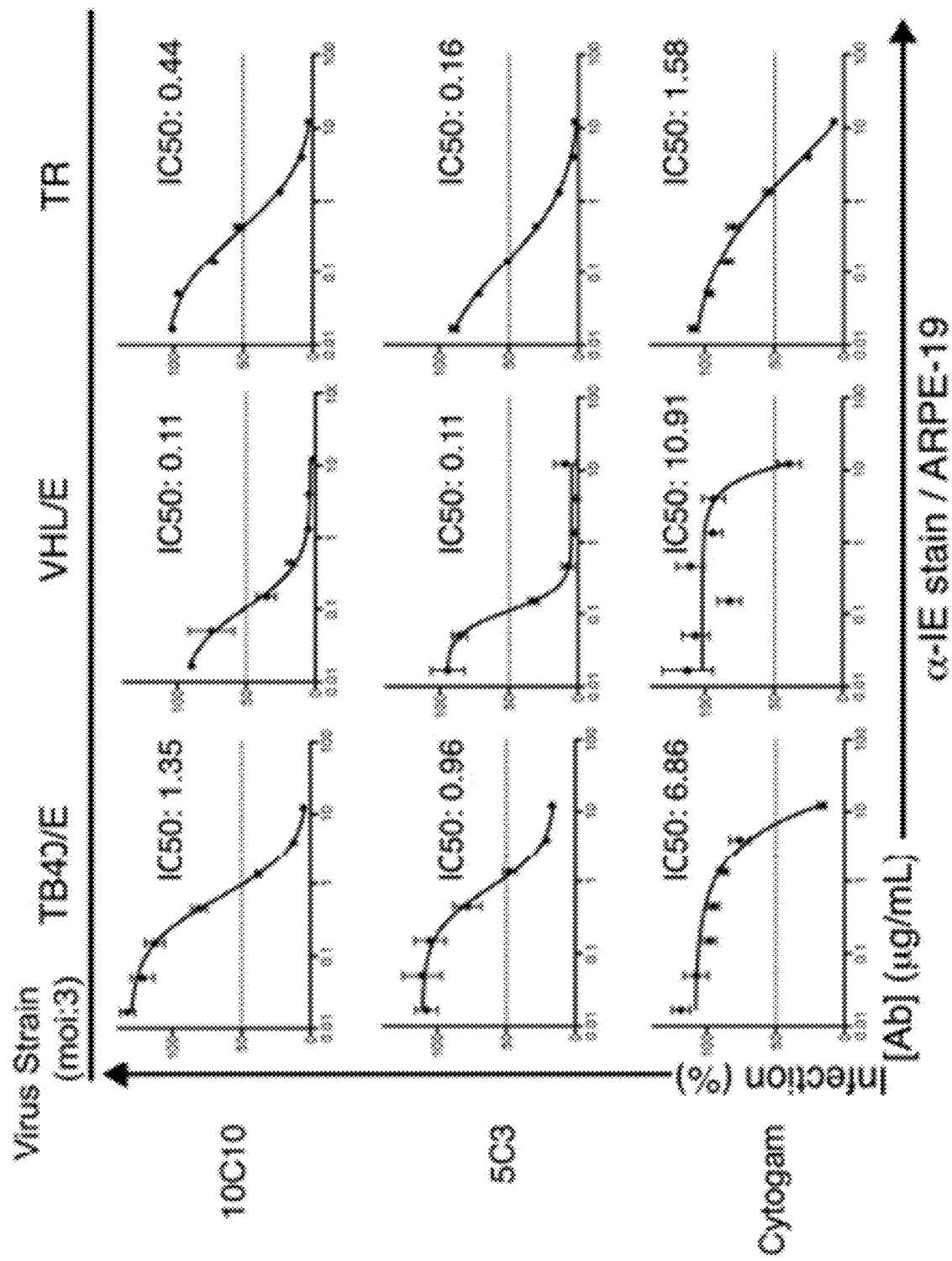

mAb incubation: 12μg/mL

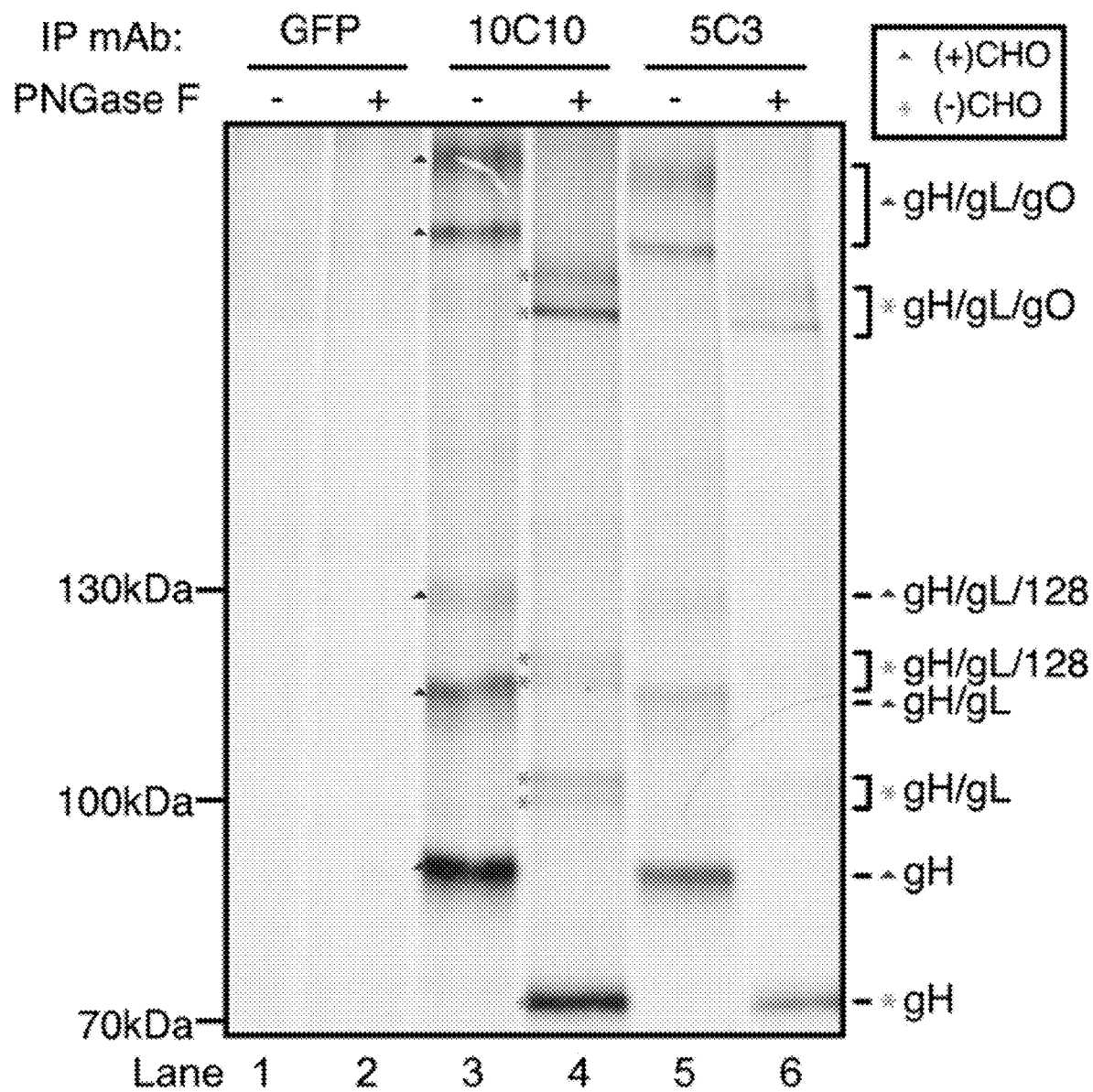

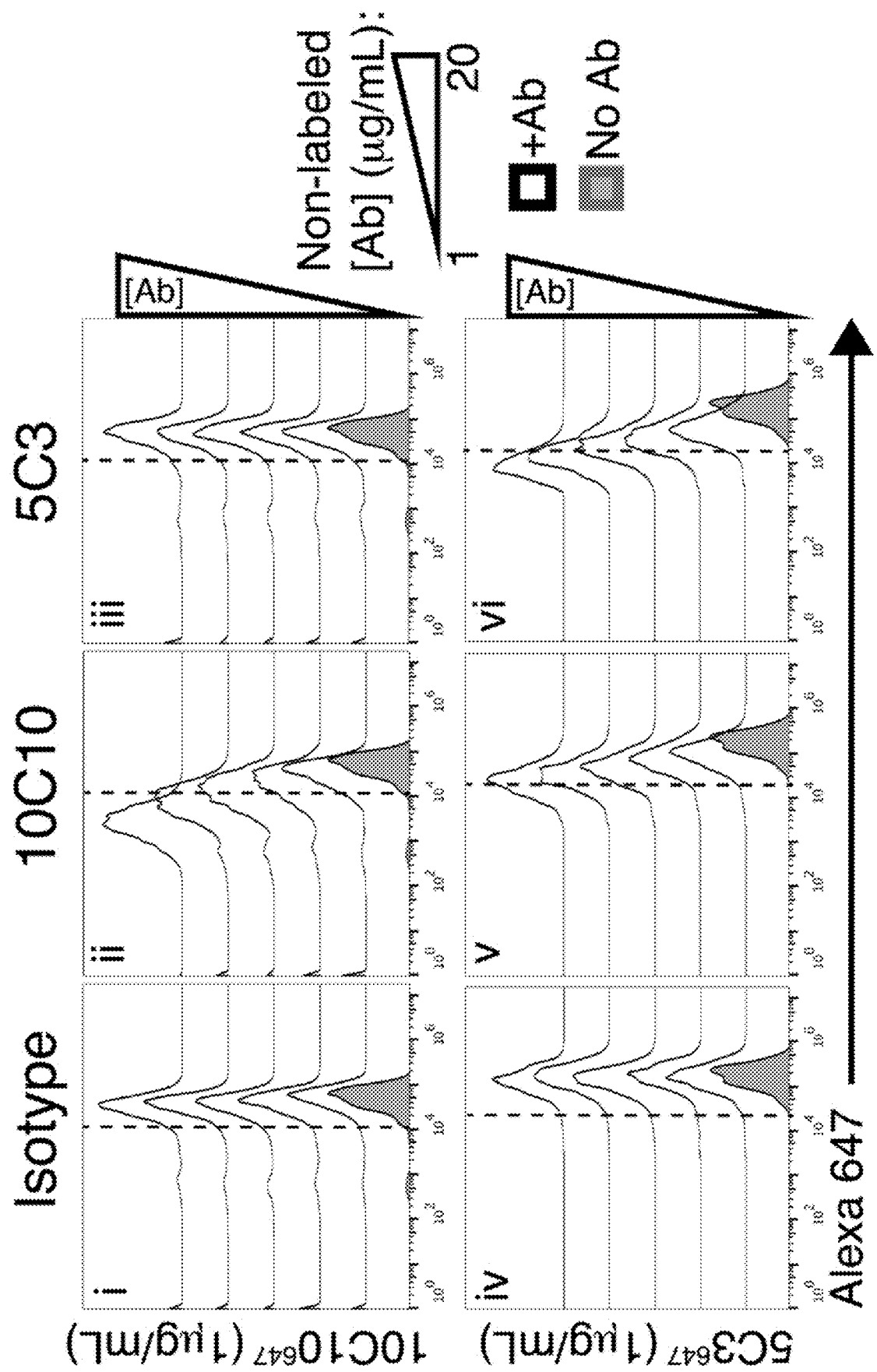

FIGURE 6B
MLVHTTERREIFIVETG
(SEQ ID NO 56)
FIGURE 6C
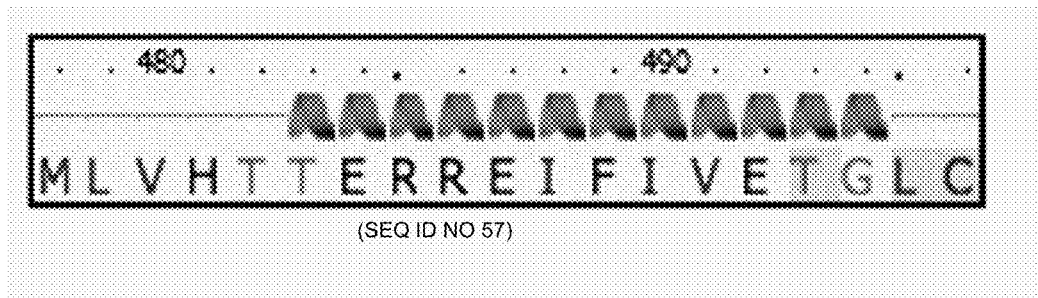
(SEQ ID NO 57)
FIGURE 6D
FIGURE 6E
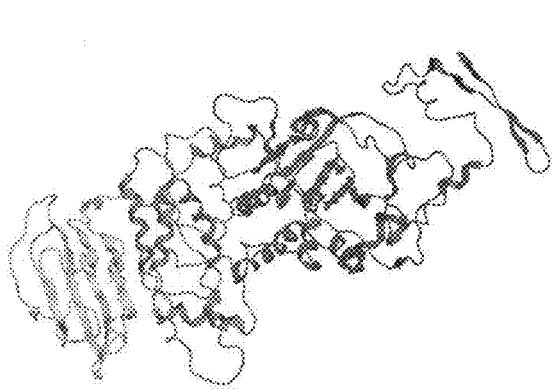 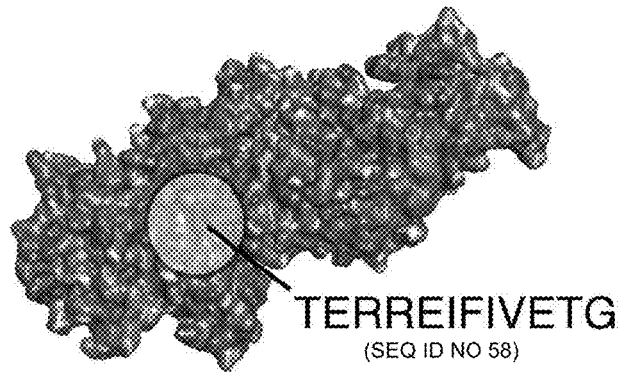
TERREIFIVETG
(SEQ ID NO 58)

FIGURE 6I

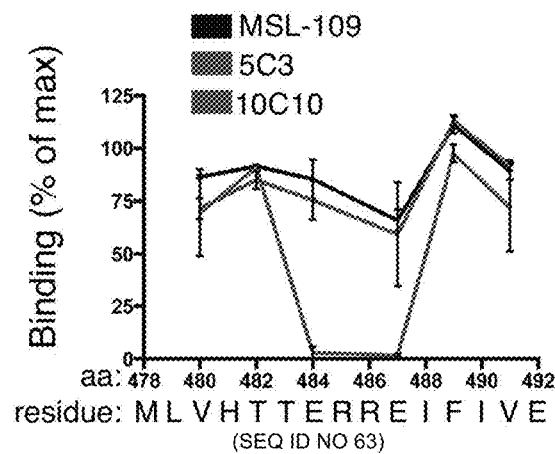

residue: M L V H T T E R R E I F I V E
(SEQ ID NO 63)

FIGURE 6J

| Strain | Origin | gH % Identity | Epitope sequence (SEQ ID NO 64) | |
|---|---|---|---|---|
| TB40/E | Germany | 100.0 | 481 TTERREIFIVETGLCSLAE 500 | |
| 3301 | UK | 97.8 | 480 TTERREIFIVETGLCSLAE 500 | |
| AD169 | USA | 100.0 | 481 TTERREIFIVETGLCSLAE 499 | |
| BE/19/2011 | Belgium | 99.9 | 481 TTERREIFIVETGLCSLAE 500 | |
| CZ/1/2011 | Czech Republic | 98.0 | 480 TTERREIFIVETGLCSLAE 499 | |
| Davis | USA | 98.8 | 481 TTERREIFIVETGLCSLAE 500 | |
| Han | China | 97.7 | 480 TTERREIFIVETGLCSLAE 499 | |
| Han30 | Germany | 97.7 | 480 TTERREIFIVETGLCSLAE 500 | |
| Merlin | UK | 97.7 | 480 TTERREIFIVETGLCSLAE 499 | |
| Pav7 | Italy | 98.0 | 480 TTERREIFIVETGLCSLAE 500 | |
| UKNEQAS2 | USA | 99.7 | 481 TTERREIFIVETGLCSLAE 500 | |
| VR1814 | Italy | 99.7 | 481 TTERREIFIVETGLCSLAE 500 | |

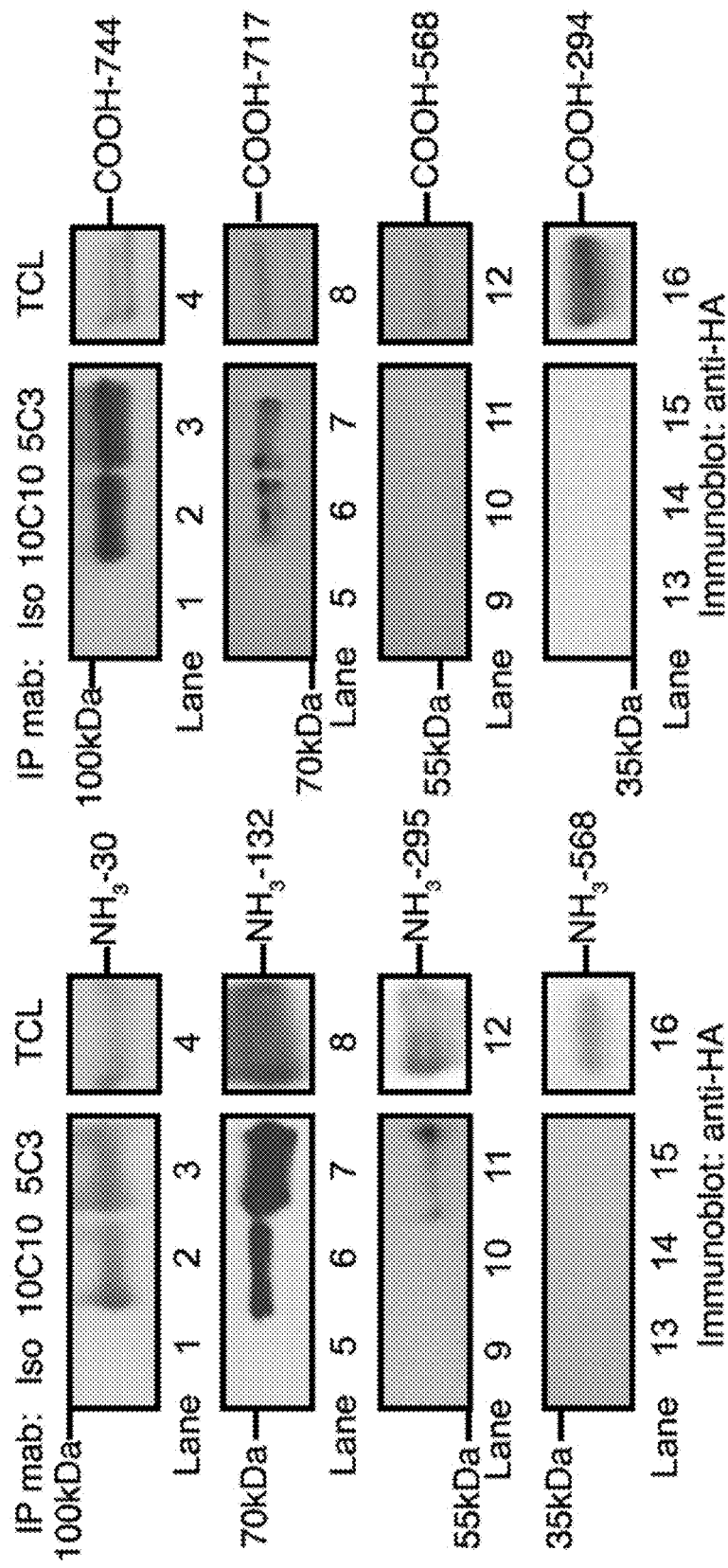

BROADLY NEUTRALIZING ANTI-HUMAN CYTOMEGALOVIRUS (HCMV) ANTIBODIES AND METHODS OF USE THEREOF

I. CROSS-REFERENCE TO RELATED APPLICATIONS

The present application is the U.S. National Phase of International Patent Application Serial No. PCT/US2017/031718, filed May 9, 2017, which claims priority to U.S. Provisional Patent Application Ser. No. 62/333,671, filed May 9, 2016, as well as U.S. Provisional Patent Application Ser. No. 62/334,270, filed May 10, 2016. The disclosures of which are hereby incorporated by reference in their entireties.

II. FIELD OF THE INVENTION

The present disclosure relates to broadly neutralizing anti-human cytomegalovirus (anti-HCMV) antibodies, vaccines, and kits, as well as methods of use, including diagnostic and therapeutic methods.

III. BACKGROUND

Human cytomegalovirus (HCMV) is a betaherpesvirus with a seroprevalance of 60-90% that can cause morbidity and mortality in susceptible individuals, with a near 100% seroprevalence in emerging countries. HCMV establishes life-long persistence within its human host. While benign in healthy individuals, HCMV poses a significant threat to the immune compromised, including transplant recipients and neonates. Primary infection and/or reactivation of this virus in immune-compromised patients may result in uncontrolled virus replication and persistent virus-mediated inflammation. HCMV is the leading cause of birth defects affecting 1-4% of newborns with approximately 40,000 new cases of HCMV infection reported annually in the United States alone. HCMV disease has been estimated to cost the US as much as $4.4 billion/year by a 1999 National Academy of Sciences report.

Existing HCMV drugs exhibit some efficacy against infection, although toxicity, drug-drug interactions, and the development of drug-resistant viral strains are common limitations. Nearly all approved anti-HCMV therapeutic compounds target the viral DNA polymerase, leading to high toxicity due to off-target effects on the host DNA polymerase. Unfortunately this precludes the use of HCMV therapeutic compounds, for example, by pregnant women with an active CMV infection. Accordingly, there is an urgent need for effective treatments and vaccines for HCMV as well as an urgent need for improved diagnostic capabilities.

IV. SUMMARY OF THE INVENTION

In one embodiment, the present disclosure is directed to an antibody or antigen-binding portion thereof that specifically binds to HCMV or an antigenic fragment thereof. In some embodiments, the antibody or antigen-binding portion thereof specifically binds to one or more epitopes on HCMV glycoprotein gH or antigenic fragments thereof. In other embodiments, the antibody or antigen-binding portion thereof specifically binds to one or more epitopes on HCMV glycoprotein gB or antigenic fragments thereof. In some embodiments, the antibody or antigen-binding portion thereof is an isolated antibody. In some embodiments, the antibody or antigen-binding portion thereof is a monoclonal antibody. In some embodiments, the antibody is a recombinant antibody. In some embodiments, the antibody is a chimeric antibody. In some embodiments, the antibody or antigen-binding portion thereof is a humanized antibody. In some embodiments, the antibody or antigen-binding portion thereof specifically binds to one or more epitopes within SEQ ID NO: 1. In some embodiments, SEQ ID NO: 1 has conservative substitutions. In some embodiments, the antibody or antigen-binding portion thereof is capable of broadly neutralizing an HCMV infection. In some embodiments, the antibody or antigen-binding portion thereof is monoclonal antibody 10C10 or an antigen-binding portion thereof. In some embodiments, the antibody or antigen-binding portion thereof is monoclonal antibody 5C3 or antigen-binding portion thereof. In some embodiments, the antibody or antigen-binding portion thereof is monoclonal antibody 8H12 or antigen-binding portion thereof.

In some embodiments, the antibody or antigen-binding portion thereof has a variable heavy chain region comprising SEQ ID NO: 9. In some embodiments, the variable heavy chain region has at least 75% homology with SEQ ID NO: 9. In some embodiments, the variable heavy chain region has at least 80% homology with SEQ ID NO: 9. In some embodiments, the variable heavy chain region has at least 85% homology with SEQ ID NO: 9. In some embodiments, the variable heavy chain region has at least 90% homology with SEQ ID NO: 9. In some embodiments, the variable heavy chain region has at least 95% homology with SEQ ID NO: 9. In some embodiments, the variable heavy chain region has more than 95% homology with SEQ ID NO: 9. In some embodiments, SEQ ID NO: 9 has at least one conservative substitution.

In some embodiments, the antibody or antigen-binding portion thereof has a variable heavy chain region comprising SEQ ID NO: 13. In some embodiments, the variable heavy chain region has at least 75% homology with SEQ ID NO: 13. In some embodiments, the variable heavy chain region has at least 80% homology with SEQ ID NO: 13. In some embodiments, the variable heavy chain region has at least 85% homology with SEQ ID NO: 13. In some embodiments, the variable heavy chain region has at least 90% homology with SEQ ID NO: 13. In some embodiments, the variable heavy chain region has at least 95% homology with SEQ ID NO: 13. In some embodiments, the variable heavy chain region has more than 95% homology with SEQ ID NO: 13. In some embodiments, SEQ ID NO: 13 has at least one conservative substitution.

In some embodiments, the antibody or antigen-binding portion thereof has a variable heavy chain region comprising SEQ ID NO: 11. In some embodiments, the variable heavy chain region has at least 75% homology with SEQ ID NO: 11. In some embodiments, the variable heavy chain region has at least 80% homology with SEQ ID NO: 11. In some embodiments, the variable heavy chain region has at least 85% homology with SEQ ID NO: 11. In some embodiments, the variable heavy chain region has at least 90% homology with SEQ ID NO: 11. In some embodiments, the variable heavy chain region has at least 95% homology with SEQ ID NO: 11. In some embodiments, the variable heavy chain region has more than 95% homology with SEQ ID NO: 11. In some embodiments, SEQ ID NO: 11 has at least one conservative substitution.

In some embodiments, the antibody or antigen-binding portion thereof has a variable light chain region comprising SEQ ID NO: 10. In some embodiments, the variable light chain region has at least 75% homology with SEQ ID NO:

10. In some embodiments, the variable light chain region has at least 80% homology with SEQ ID NO: 10. In some embodiments, the variable light chain region has at least 85% homology with SEQ ID NO: 10. In some embodiments, the variable light chain region has at least 90% homology with SEQ ID NO: 10. In some embodiments, the variable light chain region has at least 95% homology with SEQ ID NO: 10. In some embodiments, the variable light chain region has more than 95% homology with SEQ ID NO: 10. In some embodiments, SEQ ID NO: 10 has at least one conservative substitution.

In some embodiments, the antibody or antigen-binding portion thereof has a variable light chain region comprising SEQ ID NO: 14. In some embodiments, the variable light chain region has at least 75% homology with SEQ ID NO: 14. In some embodiments, the variable light chain region has at least 80% homology with SEQ ID NO: 14. In some embodiments, the variable light chain region has at least 85% homology with SEQ ID NO: 14. In some embodiments, the variable light chain region has at least 90% homology with SEQ ID NO: 14. In some embodiments, the variable light chain region has at least 95% homology with SEQ ID NO: 14. In some embodiments, the variable light chain region has more than 95% homology with SEQ ID NO: 14. In some embodiments, SEQ ID NO: 14 has at least one conservative substitution.

In some embodiments, the antibody or antigen-binding portion thereof has a variable light chain region comprising SEQ ID NO: 12. In some embodiments, the variable light chain region has at least 75% homology with SEQ ID NO: 12. In some embodiments, the variable light chain region has at least 80% homology with SEQ ID NO: 12. In some embodiments, the variable light chain region has at least 85% homology with SEQ ID NO: 12. In some embodiments, the variable light chain region has at least 90% homology with SEQ ID NO: 12. In some embodiments, the variable light chain region has at least 95% homology with SEQ ID NO: 12. In some embodiments, the variable light chain region has more than 95% homology with SEQ ID NO: 12. In some embodiments, SEQ ID NO: 12 has at least one conservative substitution.

In some embodiments, the antibody or antigen-binding portion thereof has one or more complementarity-determining regions (CDRs) of the variable heavy chain region comprising one or more of SEQ ID NO: 15, SEQ ID NO: 16, and SEQ ID NO: 17. In some embodiments, one or more of the CDRs of the variable heavy chain region has at least 75% homology with one or more of SEQ ID NO: 15, SEQ ID NO: 16, and SEQ ID NO: 17. In some embodiments, one or more of the CDRs of the variable heavy chain region has at least 80% homology with one or more of SEQ ID NO: 15, SEQ ID NO: 16, and SEQ ID NO: 17. In some embodiments, one or more of the CDRs of the variable heavy chain region has at least 85% homology with one or more of SEQ ID NO: 15, SEQ ID NO: 16, and SEQ ID NO: 17. In some embodiments, one or more of the CDRs of the variable heavy chain region has at least 90% homology with one or more of SEQ ID NO: 15, SEQ ID NO: 16, and SEQ ID NO: 17. In some embodiments, one or more of the CDRs of the variable heavy chain region has at least 95% homology with one or more of SEQ ID NO: 15, SEQ ID NO: 16, and SEQ ID NO: 17. In some embodiments, one or more of the CDRs of the variable heavy chain region has more than 95% homology one or more of SEQ ID NO: 15, SEQ ID NO: 16, and SEQ ID NO: 17. In some embodiments, one or more of SEQ ID NO: 15, SEQ ID NO: 16, and SEQ ID NO: 17 has at least one conservative substitution.

In some embodiments, the antibody or antigen-binding portion thereof has one or more complementarity-determining regions (CDRs) of the variable heavy chain region comprising one or more of SEQ ID NO: 21, SEQ ID NO: 22, and SEQ ID NO: 23. In some embodiments, one or more of the CDRs of the variable heavy chain region has at least 75% homology with one or more of SEQ ID NO: 21, SEQ ID NO: 22, and SEQ ID NO: 23. In some embodiments, one or more of the CDRs of the variable heavy chain region has at least 80% homology with one or more of SEQ ID NO: 21, SEQ ID NO: 22, and SEQ ID NO: 23. In some embodiments, one or more of the CDRs of the variable heavy chain region has at least 85% homology with one or more of SEQ ID NO: 21, SEQ ID NO: 22, and SEQ ID NO: 23. In some embodiments, one or more of the CDRs of the variable heavy chain region has at least 90% homology one or more of SEQ ID NO: 21, SEQ ID NO: 22, and SEQ ID NO: 23. In some embodiments, one or more of the CDRs of the variable heavy chain region has at least 95% homology with one or more of SEQ ID NO: 21, SEQ ID NO: 22, and SEQ ID NO: 23. In some embodiments, one or more of the CDRs of the variable heavy chain region has more than 95% homology with one or more of SEQ ID NO: 21, SEQ ID NO: 22, and SEQ ID NO: 23. In some embodiments, one or more of SEQ ID NO: 21, SEQ ID NO: 22, and SEQ ID NO: 23 has at least one conservative substitution.

In some embodiments, the antibody or antigen-binding portion thereof has one or more complementarity-determining regions (CDRs) of the variable heavy chain region comprising one or more of SEQ ID NO: 27, SEQ ID NO: 28, and SEQ ID NO: 29. In some embodiments, one or more of the CDRs of the variable heavy chain region has at least 75% homology with one or more of SEQ ID NO: 27, SEQ ID NO: 28, and SEQ ID NO: 29. In some embodiments, one or more of the CDRs of the variable heavy chain region has at least 80% homology with the one or more of SEQ ID NO: 27, SEQ ID NO: 28, and SEQ ID NO: 29. In some embodiments, one or more of the CDRs of the variable heavy chain region has at least 85% homology with one or more of SEQ ID NO: 27, SEQ ID NO: 28, and SEQ ID NO: 29. In some embodiments, one or more of the CDRs of the variable heavy chain region has at least 90% homology with one or more of SEQ ID NO: 27, SEQ ID NO: 28, and SEQ ID NO: 29. In some embodiments, one or more of the CDRs of the variable heavy chain region has at least 95% homology with one or more of SEQ ID NO: 27, SEQ ID NO: 28, and SEQ ID NO: 29. In some embodiments, one or more of the CDRs of the variable heavy chain region has more than 95% homology with one or more of SEQ ID NO: 27, SEQ ID NO: 28, and SEQ ID NO: 29. In some embodiments, one or more of SEQ ID NO: 27, SEQ ID NO: 28, and SEQ ID NO: 29 has at least one conservative substitution.

In some embodiments, the antibody or antigen-binding portion thereof has one or more complementarity-determining regions (CDRs) of the variable light chain region comprising one or more of SEQ ID NO: 18, SEQ ID NO: 19, and SEQ ID NO: 20. In some embodiments, one or more of the CDRs of the variable light chain region has at least 75% homology with one or more of SEQ ID NO: 18, SEQ ID NO: 19, and SEQ ID NO: 20. In some embodiments, one or more of the CDRs of the variable light chain region has at least 80% homology one or more of SEQ ID NO: 18, SEQ ID NO: 19, and SEQ ID NO: 20. In some embodiments, one or more of the CDRs of the variable light chain region has at least 85% homology with one or more of SEQ ID NO: 18, SEQ ID NO: 19, and SEQ ID NO: 20. In some embodiments, one or more of the CDRs of the variable light chain region has at least 90% homology with one or more of SEQ ID NO: 18, SEQ ID NO: 19, and SEQ ID NO: 20. In some embodiments, one or more of the CDRs of the variable light chain region has at least 95% homology with one or more of SEQ ID NO: 18, SEQ ID NO: 19, and SEQ ID NO: 20. In some embodiments, one or more of the CDRs of the variable light chain region has more than 95% homology with one or more of SEQ ID NO: 18, SEQ ID NO: 19, and SEQ ID NO: 20. In some embodiments, one or more of SEQ ID NO: 18, SEQ ID NO: 19, and SEQ ID NO: 20 has at least one conservative substitution.

In some embodiments, the antibody or antigen-binding portion thereof has one or more complementarity-determining regions (CDRs) of the variable light chain region comprising one or more of SEQ ID NO: 24, SEQ ID NO: 25, and SEQ ID NO: 26. In some embodiments, one or more of the CDRs of the variable light chain region has at least 75% homology with one or more of SEQ ID NO: 24, SEQ ID NO: 25, and SEQ ID NO: 26. In some embodiments, one or more of the CDRs of the variable light chain region has at least 80% homology with one or more of SEQ ID NO: 24, SEQ ID NO: 25, and SEQ ID NO: 26. In some embodiments, one or more of the CDRs of the variable light chain region has at least 85% homology with one or more of SEQ ID NO: 24, SEQ ID NO: 25, and SEQ ID NO: 26. In some embodiments, one or more of the CDRs of the variable light chain region has at least 90% homology with one or more of SEQ ID NO: 24, SEQ ID NO: 25, and SEQ ID NO: 26. In some embodiments, one or more of the CDRs of the variable light chain region has at least 95% homology with one or more of SEQ ID NO: 24, SEQ ID NO: 25, and SEQ ID NO: 26. In some embodiments, one or more of the CDRs of the variable light chain region has more than 95% homology with one or more of SEQ ID NO: 24, SEQ ID NO: 25, and SEQ ID NO: 26. In some embodiments, one or more of SEQ ID NO: 24, SEQ ID NO: 25, and SEQ ID NO: 26 has at least one conservative substitution.

In some embodiments, the antibody or antigen-binding portion thereof has one or more complementarity-determining regions (CDRs) of the variable light chain region comprising one or more of SEQ ID NO: 30, SEQ ID NO: 31, and SEQ ID NO: 32. In some embodiments, one or more of the CDRs of the variable light chain region has at least 75% homology with one or more of SEQ ID NO: 30, SEQ ID NO: 31, and SEQ ID NO: 32. In some embodiments, one or more of the CDRs of the variable light chain region has at least 80% homology with one or more of SEQ ID NO: 30, SEQ ID NO: 31, and SEQ ID NO: 32. In some embodiments, one or more of the CDRs of the variable light chain region has at least 85% homology with one or more of SEQ ID NO: 30, SEQ ID NO: 31, and SEQ ID NO: 32. In some embodiments, one or more of the CDRs of the variable light chain region has at least 90% homology with one or more of SEQ ID NO: 30, SEQ ID NO: 31, and SEQ ID NO: 32. In some embodiments, one or more of the CDRs of the variable light chain region have at least 95% homology with one or more of SEQ ID NO: 30, SEQ ID NO: 31, and SEQ ID NO: 32. In some embodiments, one or more of the CDRs of the variable light chain region has more than 95% homology with one or more of SEQ ID NO: 30, SEQ ID NO: 31, and SEQ ID NO: 32. In some embodiments, one or more of SEQ ID NO: 30, SEQ ID NO: 31, and SEQ ID NO: 32 has at least one conservative substitution.

In some embodiments, the antibody or antigen-binding portion thereof has at least one complementarity determining region (CDR) having a sequence selected from the group consisting of SEQ ID NOs: 15-32, or a sequence consisting essentially of one of SEQ ID NOs: 15-32 but having at least one conservative substitution. In some embodiments, the antibody or antigen-binding portion thereof has a heavy chain variable region that comprises CDRH1, CDRH2, and CDRH3, wherein the CDRH1, CDRH2, and CDRH3 comprise the respective sequences of a CDRH set selected from the group consisting of SEQ ID NOs: 15-17, 21-23, and 27-29 and sequences consisting essentially of SEQ ID NOs: 15-17, 21-23, and 27-29 but having at least one conservative substitution. In some embodiments, the antibody or antigen-binding portion thereof has a light chain variable region that comprises CDRL1, CDRL2, and CDRL3, wherein the CDRL1, CDRL2 and CDRL3 comprise the respective sequences of a CDRL set selected from the group consisting of SEQ ID NOs: 18-20, 24-26, and 30-32 and sequences consisting essentially of SEQ ID NOs: 18-20, 24-26, and 30-32 but having at least one conservative substitution. In some embodiments, the antibody or antigen-binding portion thereof has a heavy chain variable region that comprises CDRH1, CDRH2, and CDRH3, and a light chain variable region that comprises CDRL1, CDRL2, and CDRL3, wherein the CDRH1, CDRH2, CDRH3, CDRL1, CDRL2 and CDRL3 comprise the respective sequences of a CDR set selected from the group consisting of SEQ ID NOs: 15-20, 21-26, and 27-32, and sequences consisting essentially of SEQ ID NOs: 15-20, 21-26, and 27-32 but having at least one conservative substitution. In some embodiments, the antibody or antigen-binding portion thereof comprises one or both of (i) a heavy chain comprising a sequence selected from the group consisting of SEQ ID NOs: 9, 11 and 13, or a sequence consisting essentially of SEQ ID NOs: of 9, 11, and 13 but having at least one conservative substitution, and (ii) a light chain comprising a sequence selected from the group consisting of SEQ ID NOs: 10, 12, and 14, or a sequence consisting essentially of SEQ ID NOs: of 10, 12, and 14 but having at least one conservative substitution. In some embodiments, the heavy chain and the light chain comprise the respective sequences of SEQ ID NOs: 9-10; SEQ ID NOs: 11-12; and SEQ ID NOs: 13-14, or sequences consisting essentially of SEQ ID NOs: 9-10, SEQ ID NOs: 11-12, and SEQ ID NOs: 13-14, but having at least one conservative substitution.

In another embodiment, the present disclosure is directed to kits containing a first antibody or antigen-binding portion thereof that specifically binds to HCMV or an antigenic fragment thereof. In some embodiments, the kits contain a second antibody. In some embodiments, the second antibody or antigen-binding portion thereof specifically binds to HCMV or an antigenic fragment thereof. In other embodiments, the second antibody or antigen-binding portion thereof specifically binds to the first antibody or antigen-binding portion thereof. In some embodiments, the first antibody or antigen-binding portion thereof specifically binds to HCMV glycoprotein gH or antigenic fragments thereof. In some embodiments, the first antibody or antigen-binding portion thereof specifically binds to one or more epitopes within SEQ ID NO: 1. In some embodiments, the second antibody or antigen-binding portion thereof specifically binds to one or more epitopes within SEQ ID NO: 1. In some embodiments, SEQ ID NO: 1 has conservative substitutions. In some embodiments, the second antibody or antigen-binding portion thereof specifically binds to HCMV glycoprotein gB or antigenic fragments thereof. In other embodiments, the first antibody or antigen-binding portion thereof specifically binds to HCMV glycoprotein gB or antigenic fragments thereof. In some embodiments, at least one of the first anti-HCMV antibody or antigen-binding portion thereof and the second HCMV antibody or antigen-binding portion thereof specifically bind to anti-HCMV glycoprotein gH. In some embodiments, at least one of the first anti-HCMV antibody or antigen-binding portion thereof and the second anti-HCMV antibody or antigen-binding portion thereof specifically bind to HCMV glycoprotein gB or antigenic fragments thereof. In some embodiments, at least one of the first anti-HCMV antibody or antigen-binding portion thereof and the second anti-HCMV antibody or antigen-binding portion thereof specifically binds to HCMV glycoprotein gL or antigenic fragments thereof. In some embodiments, at least one of the first anti-HCMV antibody or antigen-binding portion thereof and the second anti-HCMV antibody or antigen-binding portion thereof specifically binds to HCMV glycoprotein gO or antigenic fragments thereof. In some embodiments, at least one of the first anti-HCMV antibody or antigen-binding portion thereof and the second anti-HCMV antibody or antigen-binding portion thereof specifically binds to UL128 or antigenic fragments thereof. In some embodiments, at least one of the first anti-HCMV antibody or antigen-binding portion thereof and the second anti-HCMV antibody or antigen-binding portion thereof specifically binds to UL130 or antigenic fragments thereof. In some embodiments, at least one of the first anti-HCMV antibody or antigen-binding portion thereof and the second anti-HCMV antibody or antigen-binding portion thereof specifically binds to UL131a or antigenic fragments thereof. In some embodiments, at least one of the first anti-HCMV antibody or antigen-binding portion thereof and the second anti-HCMV antibody or antigen-binding portion thereof specifically binds to one of HCMV glycoprotein gB or antigenic fragments thereof, HCMV glycoprotein gH or antigenic fragments thereof, HCMV glycoprotein gL or antigenic fragments thereof, HCMV glycoprotein gO or antigenic fragments thereof, UL128 or antigenic fragments thereof, UL130 or antigenic fragments thereof, and/or UL131a or antigenic fragments thereof. In some embodiments, at least one of the first anti-HCMV antibody or antigen-binding portion thereof and the second anti-HCMV antibody or antigen-binding portion thereof specifically binds to one or more epitopes within SEQ ID NO: 1. In some embodiments, the first antibody or antigen-binding portion thereof is a monoclonal antibody. In some embodiments, the second antibody or antigen-binding portion thereof is a monoclonal antibody. In some embodiments, at least one of the first antibody or antigen-binding portion thereof and the second antibody or antigen-binding portion thereof are monoclonal antibodies. In some embodiments, neither of the first antibody or antigen-binding portion thereof and the second antibody or antigen-binding portion thereof are monoclonal antibodies. In some embodiments, at least one of the first antibody or antigen-binding portion thereof and the second antibody or antigen-binding portion thereof are recombinant antibodies. In some embodiments, at least one of the first antibody or antigen-binding portion thereof and the second antibody or antigen-binding portion thereof are chimeric antibodies. In some embodiments, at least one of the first antibody or antigen-binding portion thereof and the second antibody or antigen-binding portion thereof are humanized antibodies. In some embodiments, the first antibody or antigen-binding portion thereof is bound to a substrate. In some embodiments, the second antibody or antigen-binding portion thereof is bound to a substrate. In some embodiments, the first antibody or antigen-binding portion thereof is detectably labeled. In some embodiments, the second antibody or antigen-binding portion thereof is detectably labeled. In some embodiments, at least one of the first antibody or antigen-binding portion thereof and the second antibody or antigen-binding portion thereof is detectably labeled. In some embodiments, the detectable label is a reporter molecule. In some embodiments, the reporter molecule is a fluorescent molecule. In some embodiments, the reporter is a radiolabel. In other embodiments, the detectable label is an enzyme. In some embodiments, the kits include a substrate for the enzyme. In some embodiments, adding a substrate to the enzyme leads to the production of a detectable signal. In some embodiments, the detectable signal is a colored soluble product. In some embodiments, the radiolabel is I-125. In some embodiments, the enzyme is horseradish peroxidase. In some embodiments, the substrate for the enzyme is TMB. In some embodiments, the kits are capable of quantifying the amount of HCMV or antigenic fragments thereof present in a sample. In some embodiments, the kits are capable of quantifying the amount of HCMV glycoprotein gH or an antigenic fragment thereof present in a sample. In some embodiments, the anti-HCMV antibody or antigen-binding portion thereof specifically binds to one or more epitopes within SEQ ID NO: 1. In some embodiments, SEQ ID NO: 1 has at least one conservative substitution. In some embodiments, the kits are capable of quantifying the amount of HCMV glycoprotein gB or antigenic fragments thereof present in a sample. In some embodiments, the kits have instructions for use.

In another embodiment, the present disclosure is directed to a method of detecting HCMV or an antigenic fragment thereof present in a sample. In some embodiments, the method includes the steps of i) obtaining a sample containing HCMV or an antigenic fragment thereof, ii) contacting the sample with an anti-HCMV antibody or antigen-binding portion thereof, iii) detecting the presence of specific binding of the anti-HCMV antibody or antigen-binding portion thereof to HCMV or the antigenic fragment thereof. In further embodiments, the method includes iv) quantifying the amount of HCMV or antigenic fragments thereof present in the sample. In some embodiments, the sample is a biological sample. In some embodiments, the anti-HCMV antibody or antigen-binding portion thereof specifically binds to HCMV glycoprotein gH or an antigenic fragment thereof. In some embodiments, the anti-HCMV antibody or antigen-binding portion thereof specifically binds to one or more epitopes within SEQ ID NO: 1. In some embodiments, SEQ ID NO: 1 has conservative substitutions. In other embodiments, the anti-HCMV antibody or antigen-binding portion thereof specifically binds to HCMV glycoprotein gB or an antigenic fragment thereof. In some embodiments, the anti-HCMV antibody or antigen-binding portion thereof is a monoclonal antibody. In some embodiments, the anti-HCMV antibody or antigen-binding portion thereof is a recombinant antibody. In some embodiments, the anti-HCMV antibody or antigen-binding portion thereof is a humanized antibody. In some embodiments, detecting the presence of specific binding is accomplished by an immunoassay. In some embodiments, detecting the presence of specific binding is accomplished by a competitive immunoassay.

In another embodiment, the present disclosure is directed to a method of diagnosing an individual as having an HCMV infection. In some embodiments, the method includes the steps of i) identifying an individual having, or suspected of having, an HCMV infection; ii) obtaining from the individual a sample containing HCMV or an antigenic fragment thereof, iii) contacting the sample with an anti-HCMV antibody or antigen-binding portion thereof, iv) detecting the presence of specific binding of the anti-HCMV antibody or antigen-binding portion thereof to HCMV or the antigenic fragment thereof, and v) diagnosing the individual as having an HCMV infection. In some embodiments, the sample is a biological sample. In some embodiments, the anti-HCMV antibody or antigen-binding portion thereof specifically binds to HCMV glycoprotein gH or an antigenic fragment thereof. In some embodiments, the anti-HCMV antibody or antigen-binding portion thereof specifically binds to one or more epitopes within SEQ ID NO: 1. In some embodiments, SEQ ID NO: 1 has at least one conservative substitution. In other embodiments, the anti-HCMV antibody or antigen-binding portion thereof specifically binds to HCMV glycoprotein gB or an antigenic fragment thereof. In some embodiments, the anti-HCMV antibody or antigen-binding portion thereof is a monoclonal antibody. In some embodiments, the anti-HCMV antibody or antigen-binding portion thereof is a recombinant antibody. In some embodiments, the anti-HCMV antibody or antigen binding portion thereof is a chimeric antibody. In some embodiments, the anti-HCMV antibody or antigen-binding portion thereof is a humanized antibody. In some embodiments, detecting the presence of specific binding is accomplished by an immunoassay. In some embodiments, detecting the presence of specific binding is accomplished by a competitive immunoassay.

In another embodiment, the present disclosure is directed to a method of treating an HCMV infection in an individual in need thereof. In some embodiments, the method of treating an HCMV infection includes administering to an individual having, or suspected of having, an HCMV infection at least one anti-HCMV antibody or antigen-binding portion thereof. In some embodiments, the method further includes the step of identifying an individual as having an HCMV infection prior to the administering step. In some embodiments, the anti-HCMV antibody or antigen-binding portion thereof specifically binds to glycoprotein gH or an antigenic fragment thereof. In some embodiments, the anti-HCMV antibody or antigen-binding portion thereof specifically binds to one or more epitopes within SEQ ID NO: 1. In some embodiments, SEQ ID NO: 1 has at least one conservative substitution. In some embodiments, the anti-HCMV antibody or antigen-binding portion thereof is capable of broadly neutralizing an HCMV infection. In some embodiments, the anti-HCMV antibody or antigen-binding portion thereof is a monoclonal antibody. In some embodiments, the anti-HCMV antibody is a recombinant antibody. In some embodiments, the anti-HCMV antibody or antigen-binding portion thereof is a chimeric antibody. In some embodiments, the anti-HCMV antibody or antigen-binding portion thereof is a humanized antibody. In some embodiments, the method further includes administration of at least one additional anti-HCMV antibody or antigen-binding portion thereof. In some embodiments, the additional anti-HCMV antibody or antigen-binding portion thereof specifically binds to HCMV glycoprotein gB or an antigenic fragment thereof. In some embodiments, the additional anti-HCMV antibody or antigen-binding portion thereof specifically binds to HCMV glycoprotein gL or an antigenic fragment thereof. In some embodiments, the additional anti-HCMV or antigen-binding portion thereof antibody specifically binds to HCMV glycoprotein gO or an antigenic fragment thereof. In some embodiments, the additional anti-HCMV antibody or antigen-binding portion thereof specifically binds to UL128 or an antigenic fragment thereof. In some embodiments, the additional anti-HCMV antibody or antigen-binding portion thereof specifically binds to UL130 or an antigenic fragment thereof. In some embodiments, the additional anti-HCMV antibody or antigen-binding portion thereof specifically binds to UL131a or an antigenic fragment thereof. In some embodiments, the additional anti-HCMV antibody or antigen-binding portion thereof specifically binds to one of HCMV glycoprotein gB or an antigenic fragment thereof, HCMV glycoprotein gH or an antigenic fragment thereof, HCMV glycoprotein gL or an antigenic fragment thereof, HCMV glycoprotein gO or an antigenic fragment thereof, UL128 or an antigenic fragment thereof, UL130 or an antigenic fragment thereof, and/or UL131a or an antigenic fragment thereof. In some embodiments, the additional anti-HCMV antibody or antigen-binding portion thereof specifically binds to glycoprotein gH or an antigenic fragment thereof. In some embodiments, the additional anti-HCMV antibody or antigen-binding portion thereof specifically binds to one or more epitopes within SEQ ID NO: 1. In some embodiments, SEQ ID NO: 1 has at least one conservative substitution. In some embodiments, the additional anti-HCMV antibody or antigen-binding portion thereof is a monoclonal antibody. In some embodiments, the additional anti-HCMV antibody or antigen-binding portion thereof is a recombinant antibody. In some embodiments, the additional anti-HCMV antibody or antigen-binding portion thereof is a chimeric antibody. In some embodiments, the additional anti-HCMV antibody or antigen-binding portion thereof is a humanized antibody. In some embodiments, the additional anti-HCMV antibody or antigen-binding portion thereof is a polyclonal antibody. In some embodiments, the method further includes administration of an antiviral. In some embodiments, the antiviral is ganciclovir. In some embodiments, the antiviral is one of ganciclovir, valganciclovir, forscarnet, cidofovir, and combinations thereof. In some embodiments, the method further includes administration of a pharmaceutically acceptable excipient. In some embodiments, the additional anti-HCMV antibody or antigen-binding portion thereof may be co-administered with the anti-HCMV antibody or antibodies or antigen-binding portion(s) thereof and/or antiviral or antivirals. In other embodiments, the anti-HCMV antibody or antigen-binding portion thereof is administered prior to the additional anti-HCMV antibody or antibodies or antigen-binding portion(s) thereof and/or antiviral or antivirals. In yet other embodiments, the anti-HCMV antibody or antigen-binding portion thereof is administered after the additional anti-HCMV antibody or antibodies or antigen-binding portion(s) thereof and/or antiviral or antivirals. And in yet even other embodiments, the anti-HCMV antibody or antigen-binding portion thereof may be administered in between additional anti-HCMV antibodies or antigen-binding portion(s) thereof and/or antiviral or antivirals.

In another embodiment, the present disclosure is directed to a passive vaccine. In some embodiments, the vaccine includes at least one anti-HCMV antibody or antigen-binding portion thereof. In some embodiments, the anti-HCMV antibody specifically binds to glycoprotein gH or an antigenic fragment thereof. In some embodiments, the anti-HCMV antibody or antigen-binding portion thereof specifically binds to one or more epitopes within SEQ ID NO: 1. In some embodiments, SEQ ID NO: 1 has conservative substitutions. In some embodiments, the anti-HCMV or antigen-binding portion thereof antibody is capable of broadly neutralizing an HCMV infection. In some embodiments, the anti-HCMV antibody or antigen-binding portion thereof is a monoclonal antibody. In some embodiments, the anti-HCMV antibody or antigen-binding portion thereof is a recombinant antibody. In some embodiments, the anti-HCMV antibody or antigen-binding portion thereof is a chimeric antibody. In some embodiments, the anti-HCMV antibody or antigen-binding portion thereof is a humanized antibody. In some embodiments, the passive vaccine further includes an adjuvant. In some embodiments, the passive vaccine further includes a pharmaceutically acceptable excipient.

In another embodiment, the present disclosure is directed to a method of preventing an HCMV infection in an individual in need thereof. In some embodiments, the method includes administering to an individual a passive vaccine composition containing least one anti-HCMV antibody or antigen-binding portion thereof. In some embodiments, the anti-HCMV antibody or antigen-binding portion thereof specifically binds to glycoprotein gH or an antigenic fragment thereof. In some embodiments, the anti-HCMV antibody or antigen-binding portion thereof specifically binds to one or more epitopes within SEQ ID NO: 1. In some embodiments, SEQ ID NO: 1 has at least one conservative substitution. In some embodiments, the anti-HCMV antibody or antigen-binding portion thereof is capable of broadly neutralizing an HCMV infection. In some embodiments, the anti-HCMV antibody or antigen-binding portion thereof is a monoclonal antibody. In some embodiments, the anti-HCMV antibody or antigen-binding portion thereof is a recombinant antibody. In some embodiments, the anti-HCMV antibody or antigen-binding portion thereof is a chimeric antibody. In some embodiments, the anti-HCMV antibody or antigen-binding portion thereof is a humanized antibody. In some embodiments, the passive vaccine further includes an adjuvant. In some embodiments, the passive vaccine further includes a pharmaceutically acceptable excipient.

In another embodiment, the present disclosure is directed to a method of stimulating a host immune response. In some embodiments, the method includes administering to an individual a composition containing HCMV or an antigenic fragment thereof in order to stimulate host antibody production. In some embodiments, the HCMV is attenuated. In other embodiments, the HCMV is heat-killed. In some embodiments, the antigenic fragment contains glycoprotein gH. In other embodiments, the antigenic fragment contains SEQ ID NO: 1. In some embodiments, SEQ ID NO: 1 has at least one conservative substitution. In some embodiments, the method further includes administration of an adjuvant. In some embodiments, the method further includes administration of a pharmaceutically acceptable excipient.

In another embodiment, the present disclosure is directed to nucleic acid sequences encoding the heavy and/or light chains of one or more anti-HCMV antibodies of the present disclosure. In some embodiments, the nucleic acids have conservative substitutions. In some embodiments, the nucleic acids are codon optimized.

In some embodiments, the nucleic acid sequence comprises SEQ ID NO: 3. In some embodiments, the nucleic acid sequence has at least 75% homology with SEQ ID NO: 3. In some embodiments, the nucleic acid sequence has at least 80% homology with SEQ ID NO: 3. In some embodiments, the nucleic acid sequence has at least 85% homology with SEQ ID NO: 3. In some embodiments, the nucleic acid sequence has at least 90% homology with SEQ ID NO: 3. In some embodiments, the nucleic acid sequence has at least 95% homology with SEQ ID NO: 3. In some embodiments, the nucleic acid sequence has more than 95% homology with SEQ ID NO: 3. In some embodiments, SEQ ID NO: 3 has at least one conservative substitution. In some embodiments, SEQ ID NO: 3 is codon optimized.

In some embodiments, the nucleic acid sequence comprises SEQ ID NO: 4. In some embodiments, the nucleic acid sequence has at least 75% homology with SEQ ID NO: 4. In some embodiments, the nucleic acid sequence has at least 80% homology with SEQ ID NO: 4. In some embodiments, the nucleic acid sequence has at least 85% homology with SEQ ID NO: 4. In some embodiments, the nucleic acid sequence has at least 90% homology with SEQ ID NO: 4. In some embodiments, the nucleic acid sequence has at least 95% homology with SEQ ID NO: 4. In some embodiments, the nucleic acid sequence has more than 95% homology with SEQ ID NO: 4. In some embodiments, SEQ ID NO: 4 has at least one conservative substitution. In some embodiments, SEQ ID NO: 4 is codon optimized.

In some embodiments, the nucleic acid sequence comprises SEQ ID NO: 5. In some embodiments, the nucleic acid sequence has at least 75% homology with SEQ ID NO: 5. In some embodiments, the nucleic acid sequence has at least 80% homology with SEQ ID NO: 5. In some embodiments, the nucleic acid sequence has at least 85% homology with SEQ ID NO: 5. In some embodiments, the nucleic acid sequence has at least 90% homology with SEQ ID NO: 5. In some embodiments, the nucleic acid sequence has at least 95% homology with SEQ ID NO: 5. In some embodiments, the nucleic acid sequence has more than 95% homology with SEQ ID NO: 5. In some embodiments, SEQ ID NO: 5 has at least one conservative substitution. In some embodiments, SEQ ID NO: 5 is codon optimized.

In some embodiments, the nucleic acid sequence comprises SEQ ID NO: 6. In some embodiments, the nucleic acid sequence has at least 75% homology with SEQ ID NO: 6. In some embodiments, the nucleic acid sequence has at least 80% homology with SEQ ID NO: 6. In some embodiments, the nucleic acid sequence has at least 85% homology with SEQ ID NO: 6. In some embodiments, the nucleic acid sequence has at least 90% homology with SEQ ID NO: 6. In some embodiments, the nucleic acid sequence has at least 95% homology with SEQ ID NO: 6. In some embodiments, the nucleic acid sequence has more than 95% homology with SEQ ID NO: 6. In some embodiments, SEQ ID NO: 6 has at least one conservative substitution. In some embodiments, SEQ ID NO: 6 is codon optimized.

In another embodiment, the present disclosure is directed to a vector or system of vectors containing one or more nucleic acid sequences encoding the heavy and/or light chains of one or more of the anti-HCMV antibodies of the present disclosure. In some embodiments, the vector or vector system comprises SEQ ID NO: 3. In some embodiments, the vector or vector system comprises a nucleic acid sequence has at least 75% homology with SEQ ID NO: 3. In some embodiments, the the vector or vector system comprises a nucleic acid sequence has at least 80% homology with SEQ ID NO: 3. In some embodiments, the vector or vector system comprises a nucleic acid sequence has at least 85% homology with SEQ ID NO: 3. In some embodiments, the vector or vector system comprises a nucleic acid sequence has at least 90% homology with SEQ ID NO: 3. In some embodiments, the vector or vector system comprises a nucleic acid sequence has at least 95% homology with SEQ ID NO: 3. In some embodiments, the vector or vector system comprises a nucleic acid sequence has more than 95% homology with SEQ ID NO: 3. In some embodiments, SEQ ID NO: 3 has at least one conservative substitution. In some embodiments, SEQ ID NO: 3 is codon optimized.

In some embodiments, the vector or vector system comprises SEQ ID NO: 4. In some embodiments, the vector or vector system comprises a nucleic acid sequence has at least 75% homology with SEQ ID NO: 4. In some embodiments, the the vector or vector system comprises a nucleic acid sequence has at least 80% homology with SEQ ID NO: 4. In some embodiments, the vector or vector system comprises a nucleic acid sequence has at least 85% homology with SEQ ID NO: 4. In some embodiments, the vector or vector system comprises a nucleic acid sequence has at least 90% homology with SEQ ID NO: 4. In some embodiments, the vector or vector system comprises a nucleic acid sequence has at least 95% homology with SEQ ID NO: 4. In some embodiments, the vector or vector system comprises a nucleic acid sequence has more than 95% homology with SEQ ID NO: 4. In some embodiments, SEQ ID NO: 4 has at least one conservative substitution. In some embodiments, SEQ ID NO: 4 is codon optimized.

In some embodiments, the vector or vector system comprises SEQ ID NO: 5. In some embodiments, the vector or vector system comprises a nucleic acid sequence has at least 75% homology with SEQ ID NO: 5. In some embodiments, the the vector or vector system comprises a nucleic acid sequence has at least 80% homology with SEQ ID NO: 5. In some embodiments, the vector or vector system comprises a nucleic acid sequence has at least 85% homology with SEQ ID NO: 5. In some embodiments, the vector or vector system comprises a nucleic acid sequence has at least 90% homology with SEQ ID NO: 5. In some embodiments, the vector or vector system comprises a nucleic acid sequence has at least 95% homology with SEQ ID NO: 5. In some embodiments, the vector or vector system comprises a nucleic acid sequence has more than 95% homology with SEQ ID NO: 5. In some embodiments, SEQ ID NO: 5 has at least one conservative substitution. In some embodiments, SEQ ID NO: 5 is codon optimized.

In some embodiments, the vector or vector system comprises SEQ ID NO: 6. In some embodiments, the vector or vector system comprises a nucleic acid sequence has at least 75% homology with SEQ ID NO: 6. In some embodiments, the the vector or vector system comprises a nucleic acid sequence has at least 80% homology with SEQ ID NO: 6. In some embodiments, the vector or vector system comprises a nucleic acid sequence has at least 85% homology with SEQ ID NO: 6. In some embodiments, the vector or vector system comprises a nucleic acid sequence has at least 90% homology with SEQ ID NO: 6. In some embodiments, the vector or vector system comprises a nucleic acid sequence has at least 95% homology with SEQ ID NO: 6. In some embodiments, the vector or vector system comprises a nucleic acid sequence has more than 95% homology with SEQ ID NO: 6. In some embodiments, SEQ ID NO: 6 has at least one conservative substitution. In some embodiments, SEQ ID NO: 6 is codon optimized.

In some embodiments, the vector or vector system comprises a nucleic acid sequence coding for a variable heavy chain region and a nucleic acid sequence coding for a variable light chain region. In some embodiments, a nucleic acid sequence coding for a heavy chain is on the same vector as a nucleic acid sequence coding for a light chain. In some embodiments, a nucleic acid sequence coding for a variable heavy chain region is on a different vector than a nucleic acid sequence coding for a variable light chain region. In some embodiments, the vector or system of vectors is a plasmid or plasmids. In some embodiments, the vector or a system of vectors is a phage vector or vectors. In some embodiments, the phage vector is a γ phage. In some embodiments, the vector or vectors is a cosmid or cosmids. In some embodiments, the vector or system of vectors is a recombinant chromosome or recombinant chromosomes. In some embodiments, the vector system is a combination of different vectors. In some embodiments, expression of the different nucleic acid sequences may be concomitant. In other embodiments, expression of the different nucleic acid sequences may be separately inducible. In another embodiment, the present disclosure is directed to a vector or system of vectors containing one or more nucleic acid sequences encoding one or more complementarity determining regions (CDRs) of one or more heavy and/or light chains of one or more of the anti-HCMV antibodies of the present disclosure. In some embodiments, the present invention is directed to a cell transformed with a vector or vector system of the present disclosure. In some embodiments, the cell is a bacterial cell, a yeast cell, a plant cell, or a mammalian cell. In some embodiments, the mammalian cell is one of a chinese hamster ovary (CHO) cell, including DUXB11, DG44 and CHOK1 lineages, a NS0 murine myeloma cell, a PER.C6 cell, and a human embryonic kidney (HEK) cell, including HEK293 lineages.

In another embodiment, the present disclosure is directed to a method of making a recombinant antibody or antigen-binding portion thereof. In some embodiments, the recombinant antibody is a chimeric antibody. In some embodiments, the recombinant antibody is a humanized antibody. In some embodiments, the method includes the steps of i. transforming a host cell with at least one vector containing at least nucleic acid sequence encoding at least one of 1) a heavy chain and a light chain of one or more anti-HCMV antibodies or 2) at least one or more complementarity determining regions (CDRs) of one or more heavy and/or light chains of one or more of the anti-HCMV antibodies, ii. expressing the at least one nucleic acid sequence to create a recombinant antibody (or antigen-binding portion thereof), and iii. recovering the recombinant antibody or antigen-binding portion thereof.

In another embodiment, the present disclosure is directed to an anti-HCMV antibody or antigen-binding portion thereof for use in medicine. In some embodiments, the anti-HCMV antibody or antigen-binding portion thereof is any anti-HCMV antibody or antigen-binding portion thereof of the present disclosure.

In another embodiment, the present disclosure is directed to an anti-HCMV antibody or antigen-binding portion thereof for use in treatment of an HCMV infection. In some embodiments, the anti-HCMV antibody or antigen-binding portion thereof is any anti-HCMV antibody or antigen-binding portion thereof of the present disclosure.

In another embodiment, the present disclosure is directed to an anti-HCMV antibody or antigen-binding portion thereof for use as a medicament. In some embodiments, the anti-HCMV antibody or antigen-binding portion thereof is any anti-HCMV antibody or antigen-binding portion thereof of the present disclosure.

In another embodiment, the present disclosure is directed to use of an anti-HCMV antibody or antigen-binding portion thereof for the manufacture of a medicament for use in the treatment of an HCMV infection. In some embodiments, the anti-HCMV antibody or antigen-binding portion thereof is any anti-HCMV antibody or antigen-binding portion thereof of the present disclosure.

V. BRIEF DESCRIPTION OF THE DRAWINGS

Figure 1B:
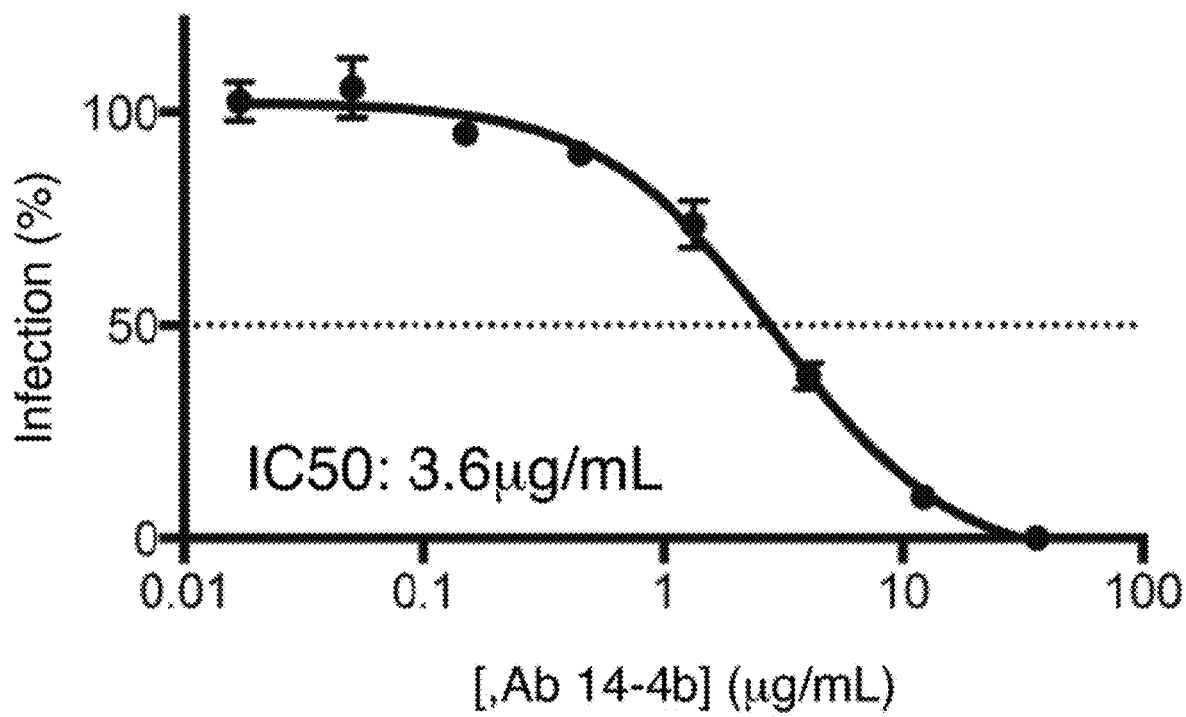
Figure 1C:
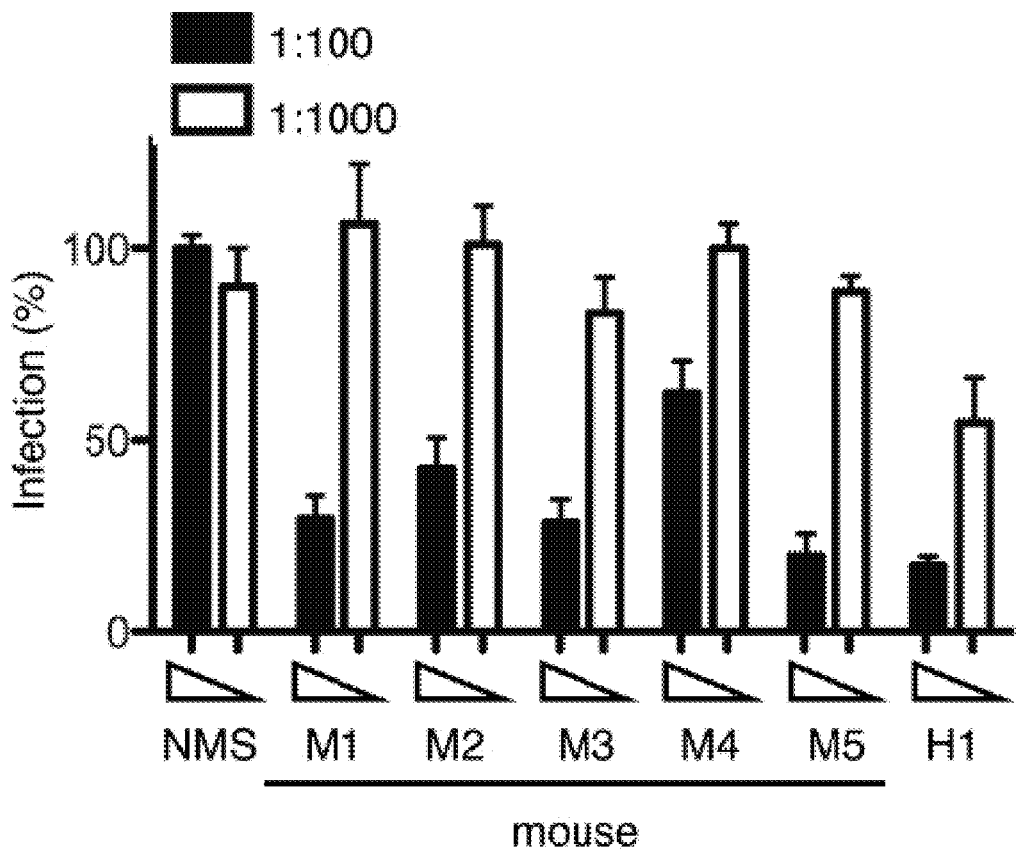
Figure 1D:
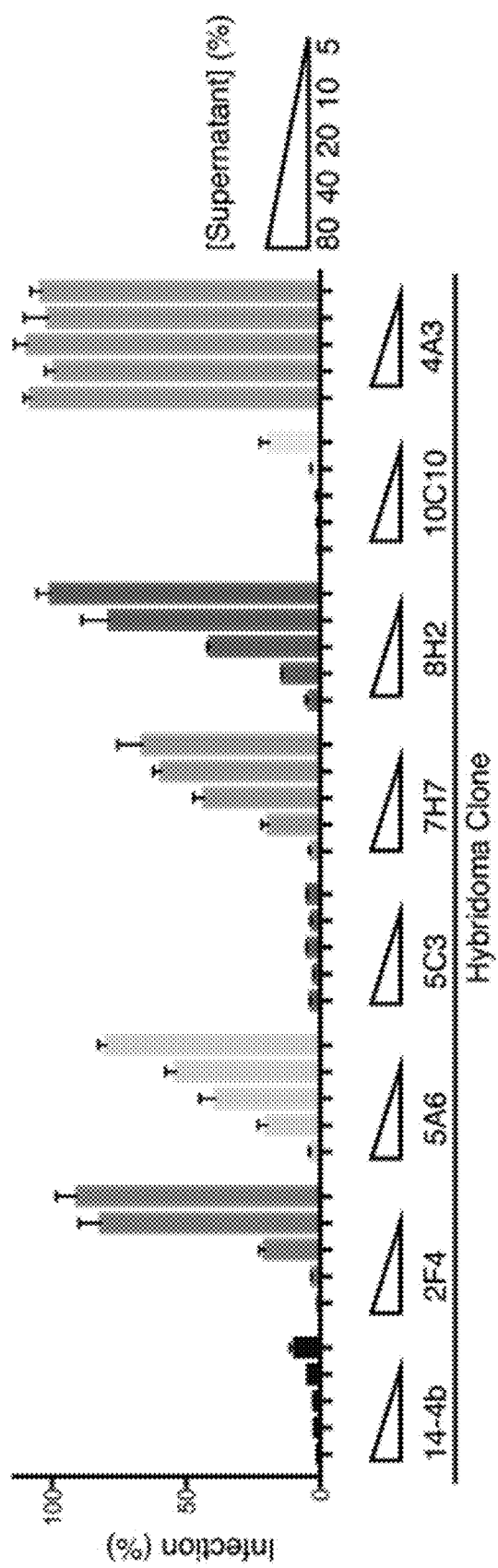
Figure 1F:
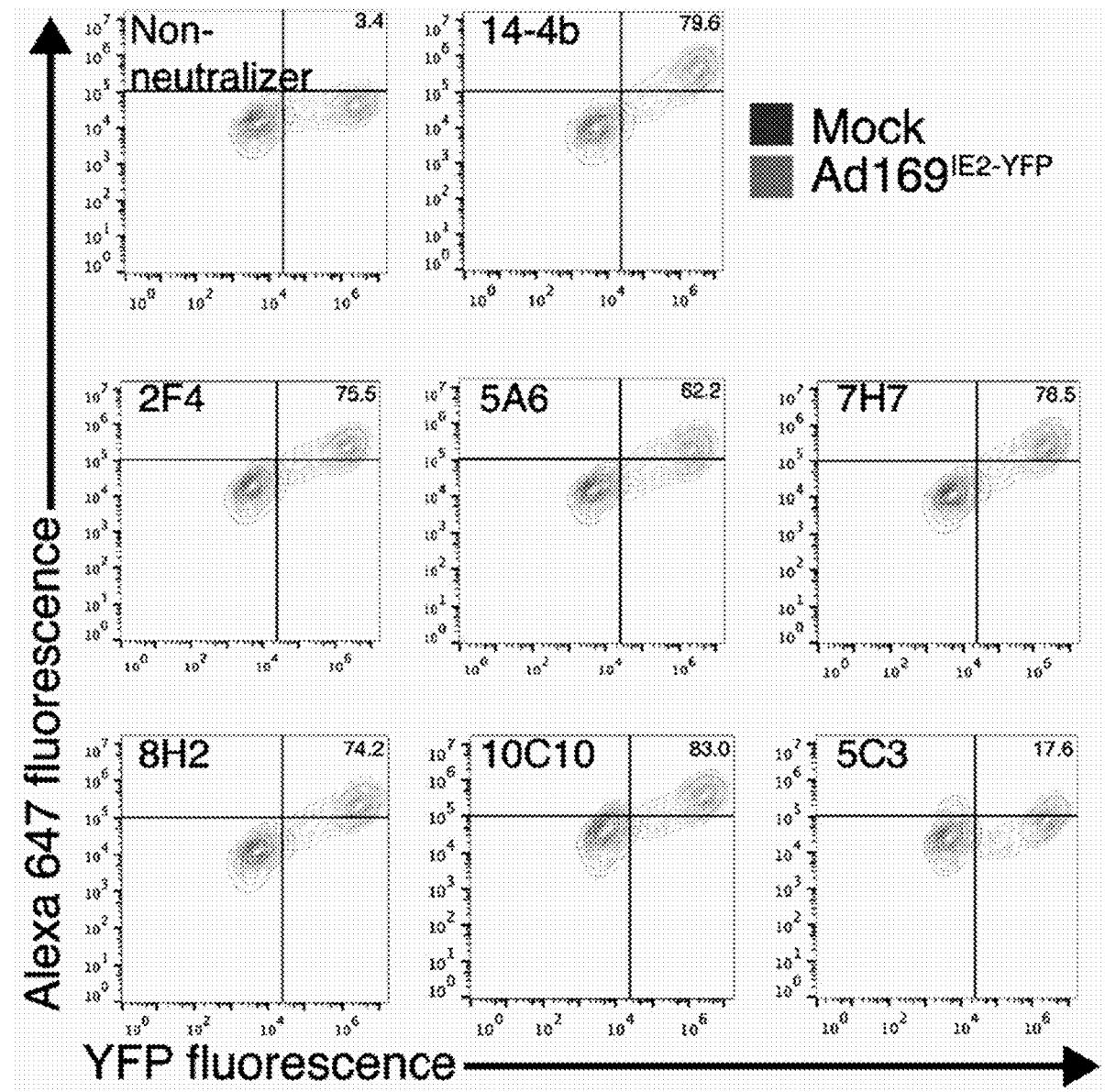

FIGS. 1A through 1E represent identification of HCMV-neutralizing mAbs using a high-throughput neutralization assay. FIG. 1A: Human serum, purified mAb, and Hybridoma supernatant were tested in a high-throughput neutralization (HTN) assay for their ability to block infection of fibroblasts by AD169$_{IE2\text{-}YFP}$. FIG. 1B: Neutralization activity using the AD169IIE2-YFP neutralization assay. FIG. 1C: Serum from mice inoculated with AD169 was tested for its ability to neutralize AD169$_{IE2\text{-}YFP}$ infection at 1:100 (black bars) or 1:000 (white bars). Normal mouse serum (NMS) or HCMV+ human serum (H1) were used as controls. FIG. 1D: Hybridoma supernatant from 6 HCMV-neutralizing clones was tested in 5-point dilutions (5-80%) for their ability to inhibit AD169$_{IE2\text{-}YFP}$ infection. Supernatant from the neutralizing anti-gH mAb 14-4b and supernatant from the non-neutralizing hybridoma clone 4A3 were utilized as controls. FIG. 1E: MRC5 cells infected with AD169$_{IE2\text{-}YFP}$ were exposed to anti-gH flow cytometry staining without (top row) or with (bottom row) permeabilization with saponin. FIG. 1F: Mock-infected MRC5 cells or infected with AD169$_{IE2\text{-}YFP}$ were permeabilized and then exposed to hybridoma supernatant from the HCMV-neutralizing clones followed by detection with flow cytometry.

Figure 2A:
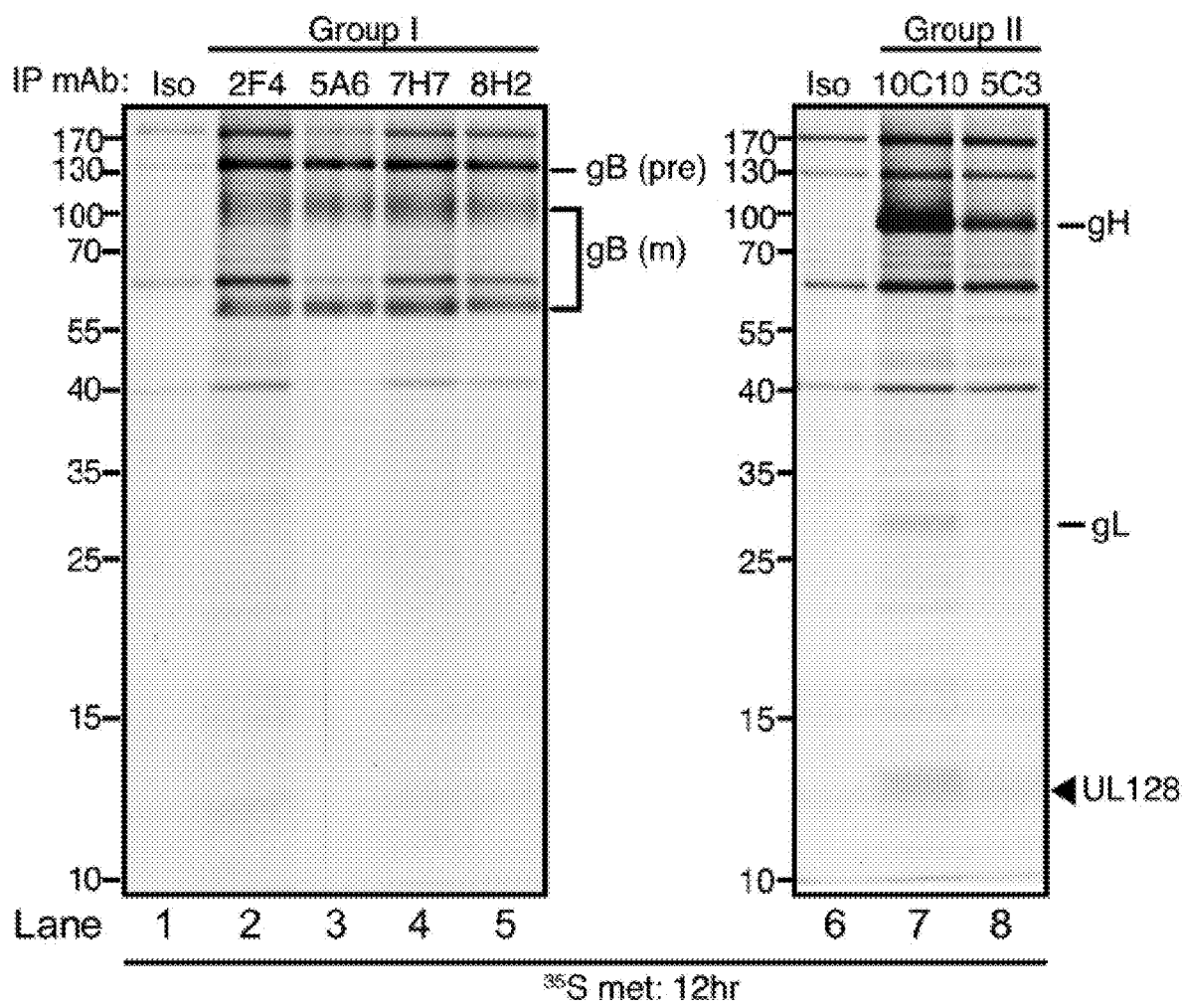
Figure 2B:
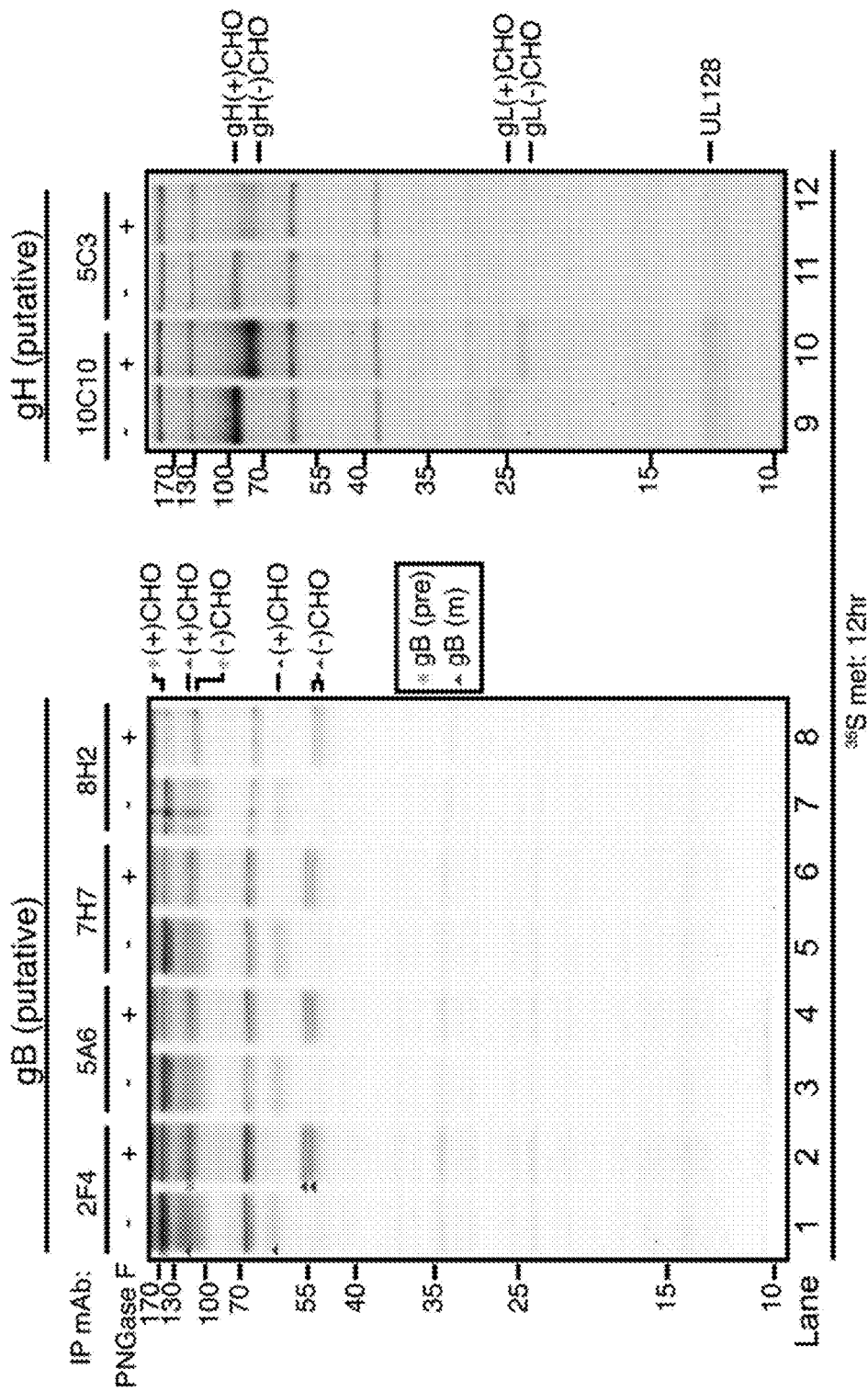
Figure 2C:
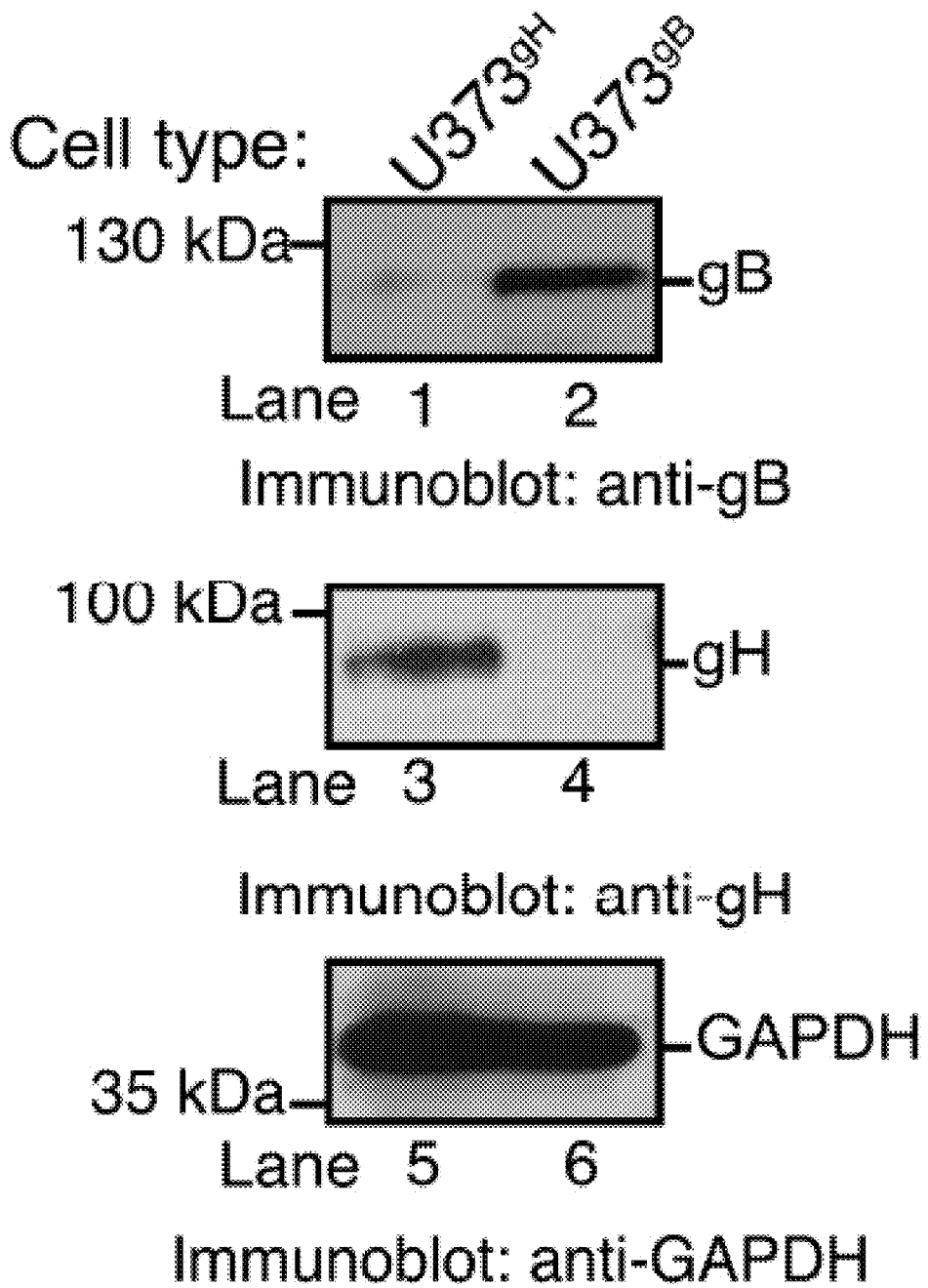
Figure 2D:
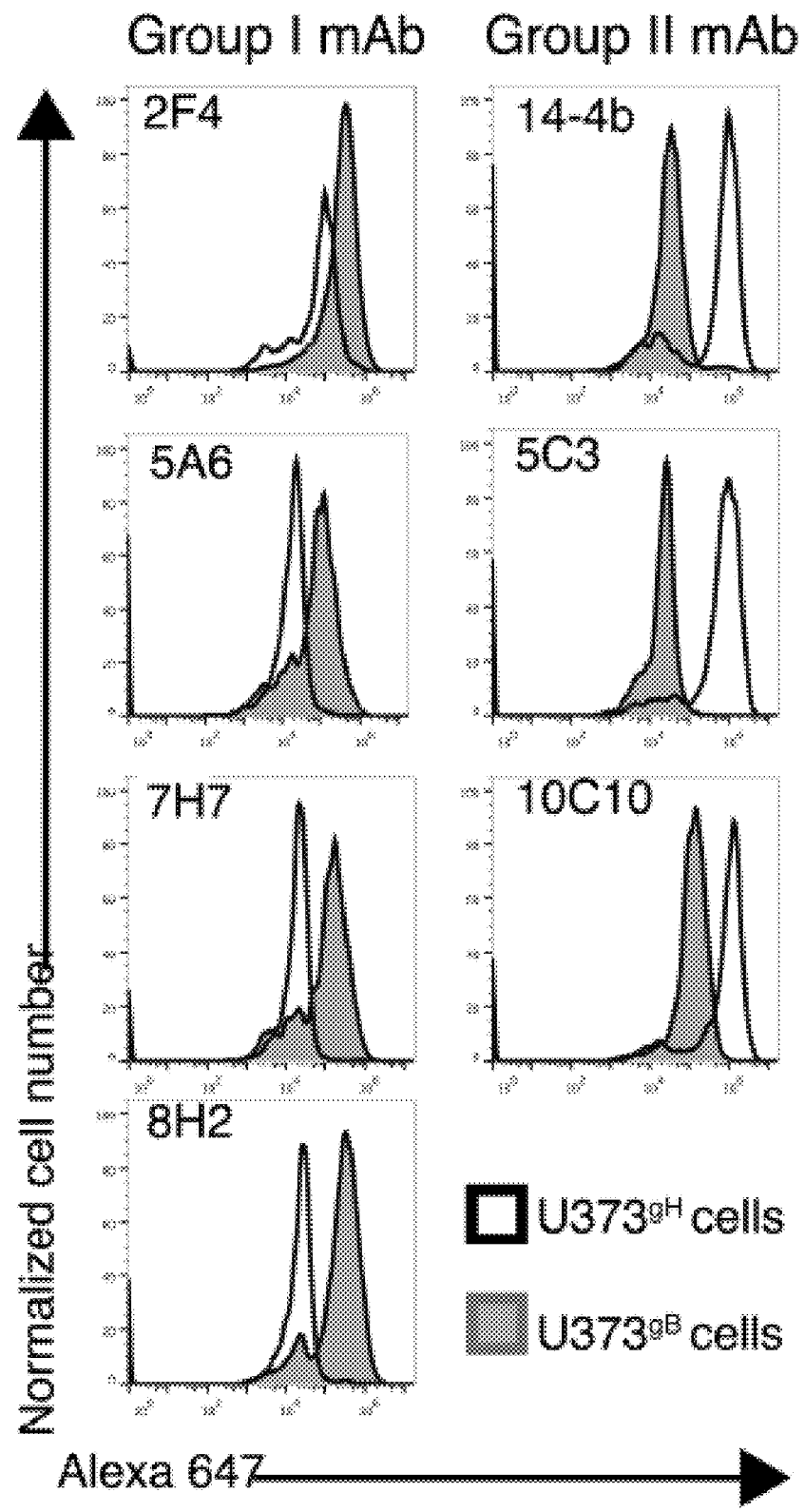
Figure 2E:
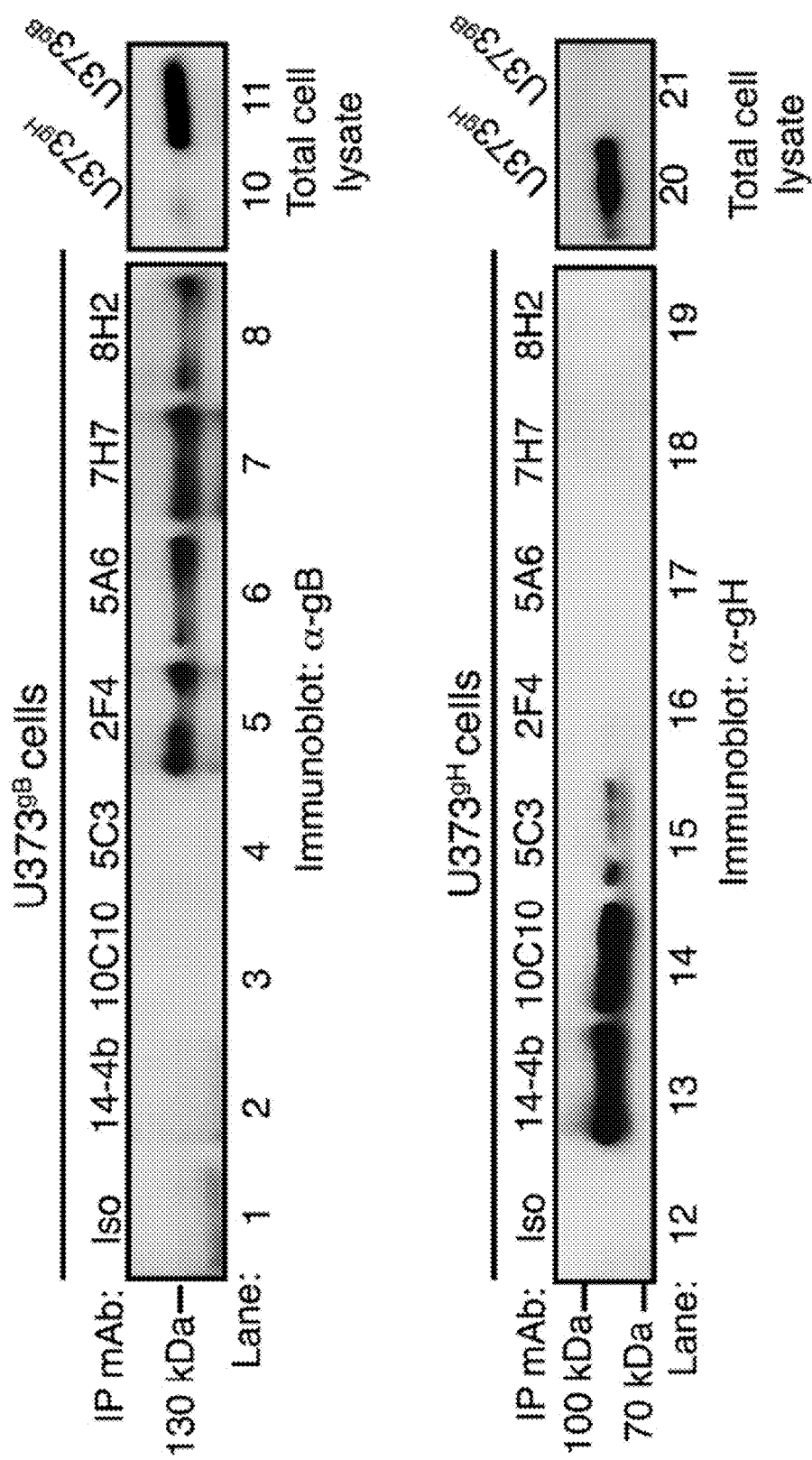

FIGS. 2A through 2E represent identification of HCMV-neutralizing mAb targets. FIG. 2A: Lysates from metabolically-labeled AD169$_{IE2\text{-}YFP}$-infected MRC5 cells were exposed to the HCMV-neutralizing mAbs and recovered immune complexes were resolved by SDS-PAGE. Arrows denote the suspected peptide identity. FIG. 2B: Immune complexes recovered from the metabolically-labeled cell lysates were exposed to Peptide-N-Glycosidase F (PNGase F) treatment and resolved by SDS-PAGE. Arrows denote the suspected peptide identity and glycosylation state. FIG. 2C: Total cell lysates from U373 glioblastoma cells stably expressing gH (U373$^{gH}$) or gB (U373$^{gB}$) were resolved by SDS-PAGE and exposed to immunoblot for gB (lanes 1-2), gH (lanes 3-4), and glyceraldehyde-3-phosphate dehydrogenase (GAPDH) (lanes 5-6) proteins. FIG. 2D: U373$^{gH}$ (white peaks) and U373$^{gB}$ (gray peaks) cells were permeabilized and exposed to the neutralizing CMV mAbs followed by detection with flow cytometry. mAb 14-4b was used as a positive control for labeling of the gH protein. FIG. 2E: Total cell lysates from U373$^{gB}$ (lanes 1-8) and U373$^{gH}$ (lanes 12-19) were exposed to the CMV-neutralizing mAbs. The recovered immune complexes were resolved by SDS-PAGE and exposed to anti-gB (lanes 1-8) or anti-gH (lanes 12-19) antibody. Total cell lysates from U373$^{gB}$ (lanes 10-11) and U373$^{gH}$ (lanes 20-21) validated expression of the respective HCMV protein in each cell type. Relative molecular mass markers are indicated in all relevant figures.

Figure 3A:
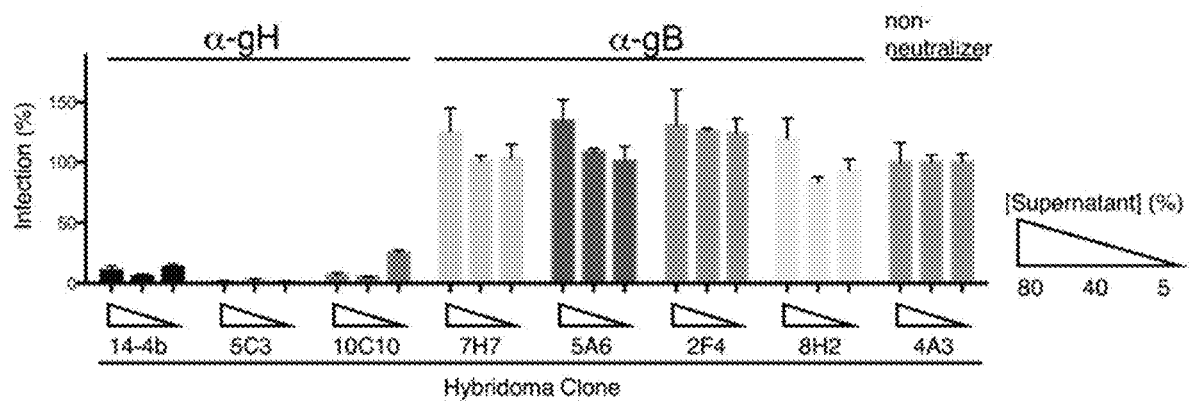
Figure 3B:
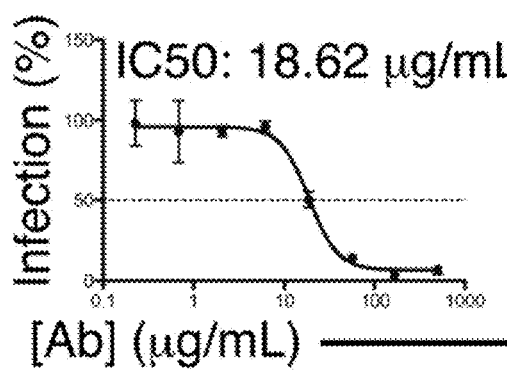
Figure 3B:
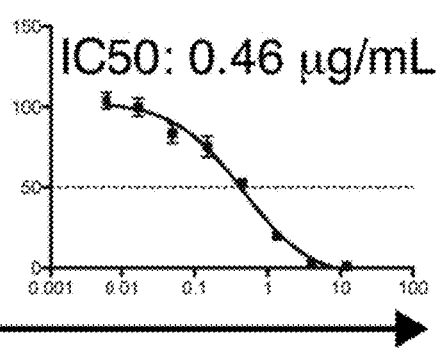
Figure 3C:
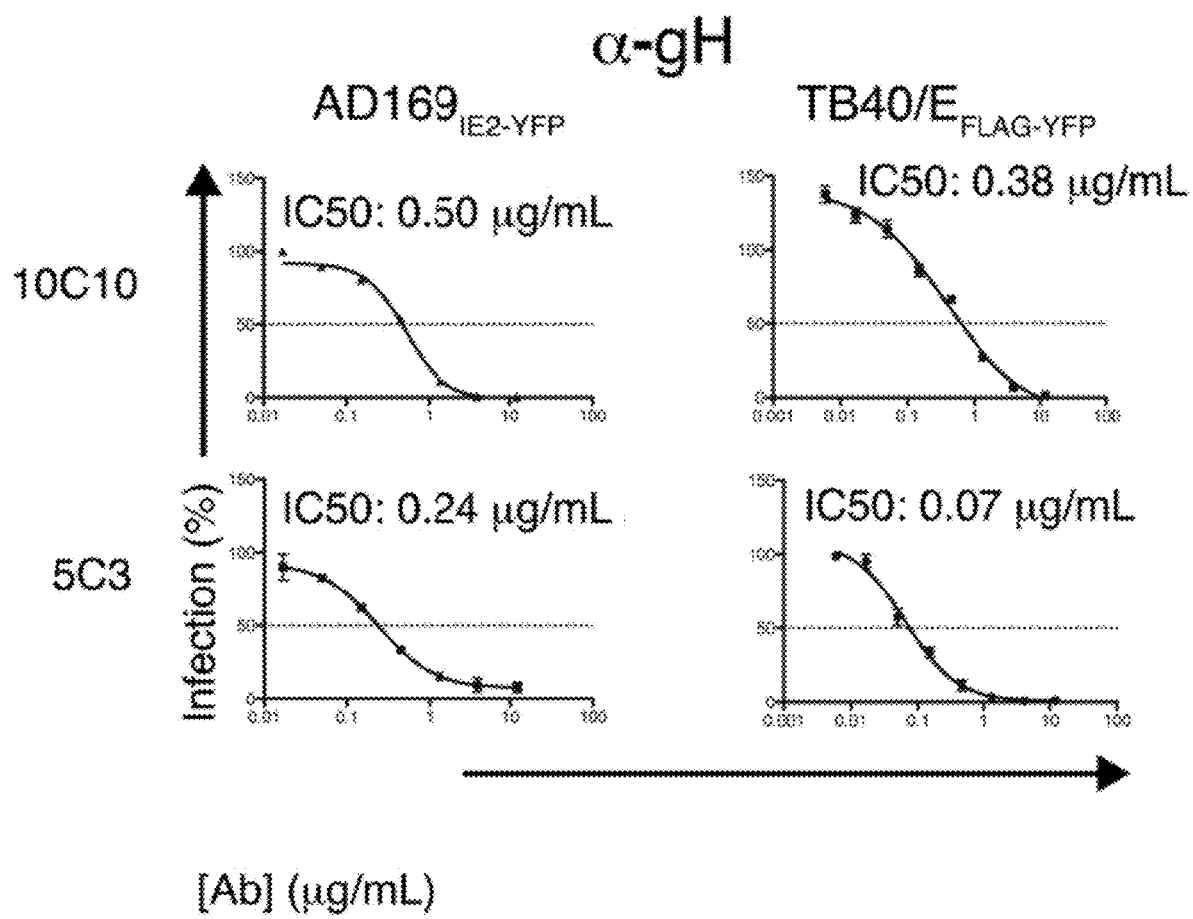
Figure 3D:
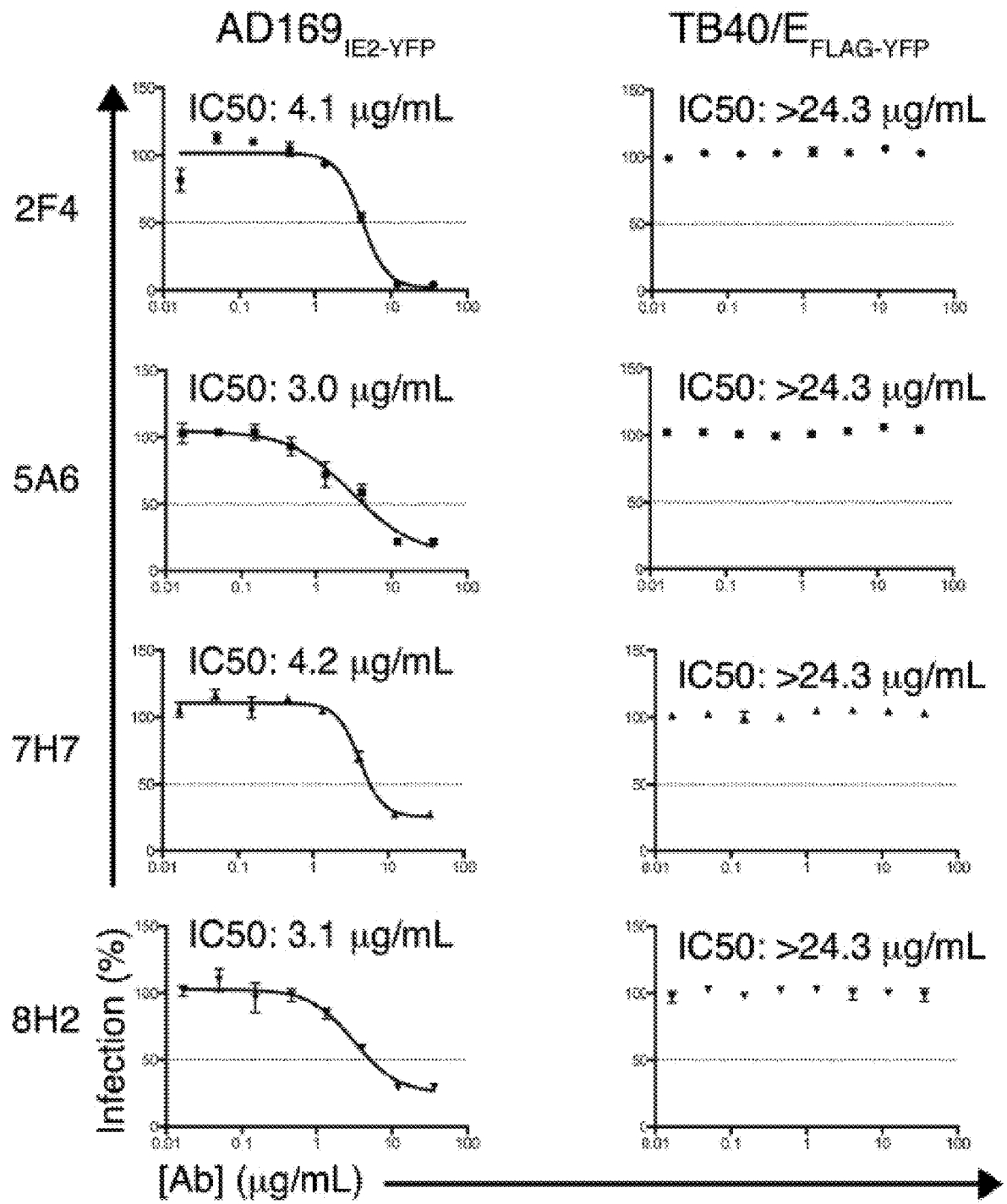
Figure 3E:
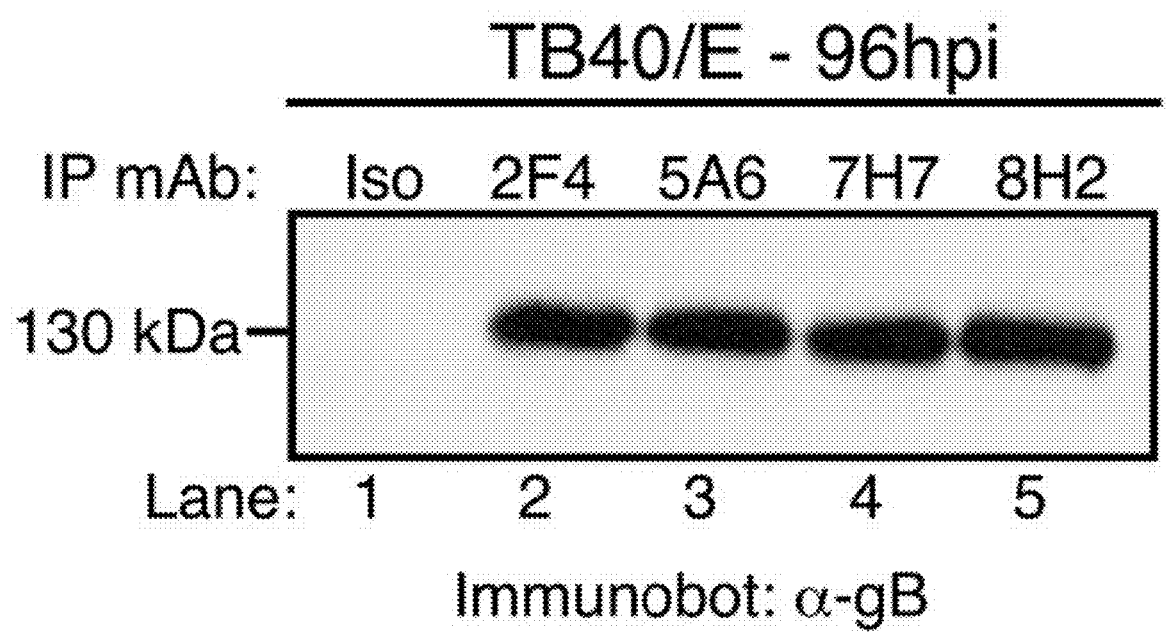

FIGS. 3A through 3E represent an examination of the neutralizing capacity of anti-HCMV mAbs. FIG. 3A: Hybridoma supernatant from the 6 HCMV-neutralizing mAbs was tested at 3 concentrations (5, 40, 80%) for their ability to inhibit TB40/E$_{FLAG\text{-}YFP}$ infection of MRC5 cells. Supernatant from the neutralizing anti-gH mAb 14-4b and supernatant from the non-neutralizing hybridoma clone 4A3 were utilized as controls. FIG. 3B: Cytogam® was pre-incubated with AD169$_{IE2\text{-}YFP}$ (left panel) and TB40/E$_{FLAG\text{-}YFP}$ (right panel) at 8 concentrations (0.01-12 µg/mL) and infection levels of MRC5 cells was subsequently measured. FIG. 3C: Anti-gH mAbs 10C10 and 5C3 were pre-incubated with AD169$_{IE2\text{-}YFP}$ (left panel) and TB40/E$_{FLAG\text{-}YFP}$ (right panel) at 8 concentrations (0.01-12 µg/mL) and infection levels of MRC5 cells was subsequently measured. FIG. 3D: Anti-gB mAbs 2F4, 5A6, 7H7 and 8H2 were pre-incubated with AD169$_{IE2\text{-}YFP}$ (left panel) and TB40/E$_{FLAG\text{-}YFP}$ (right panel) at 8 concentrations (0.01-12 µg/mL) and infection levels of MRC5 cells was subsequently measured. Non-linear regression analysis was performed and the half maximal inhibitory concentration (IC50) was calculated for all antibodies. FIG. 3E: MRC5 cells infected with TB40/E were harvested at 96 hpi and total cell lysates were exposed to the anti-gB antibodies. Recovered immune complexes were resolved by SDS-PAGE and exposed to anti-gB immunoblot (Lanes 1-5). Relative molecular mass markers are indicated.

Figure 4A:
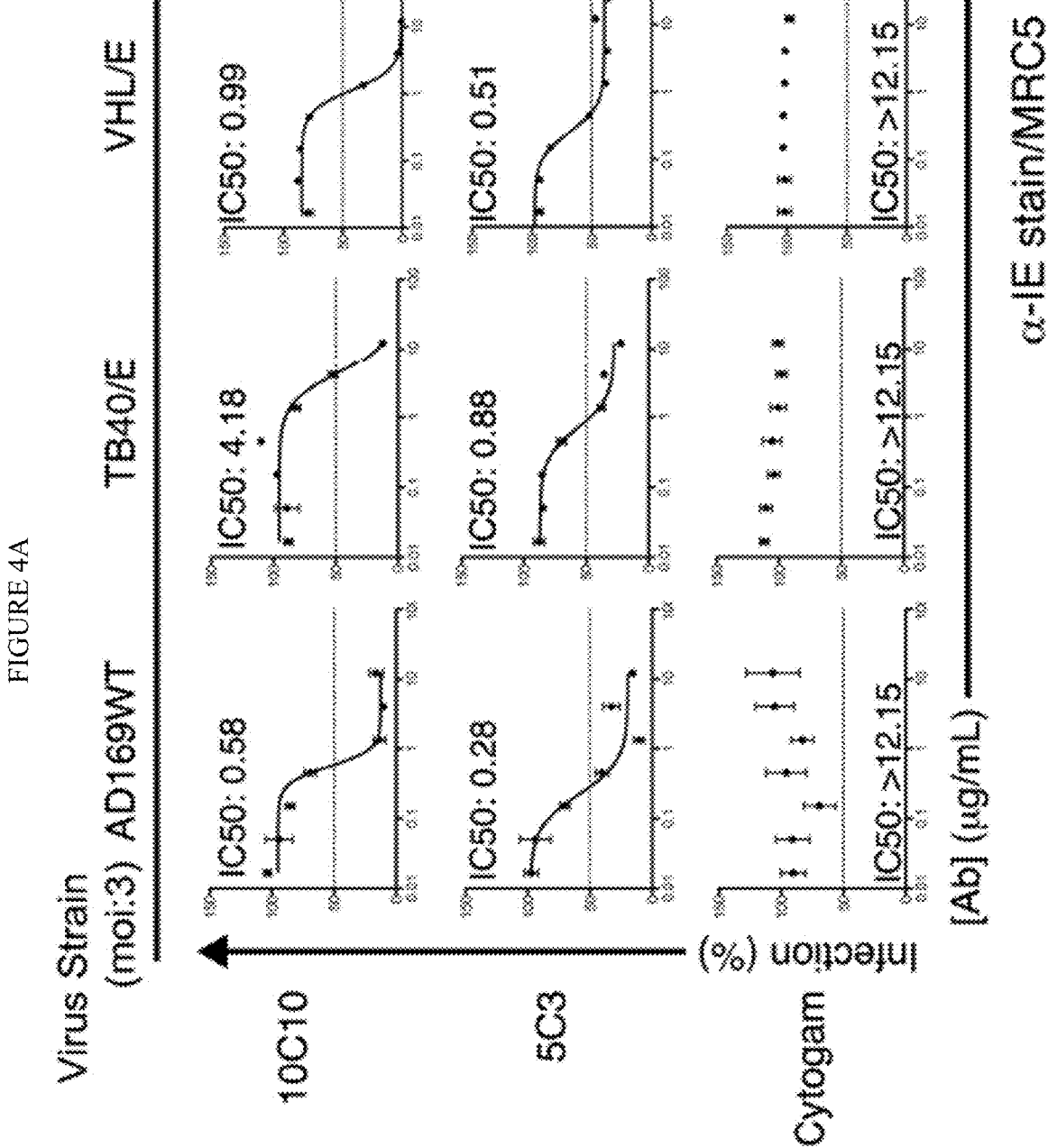
Figure 4B:
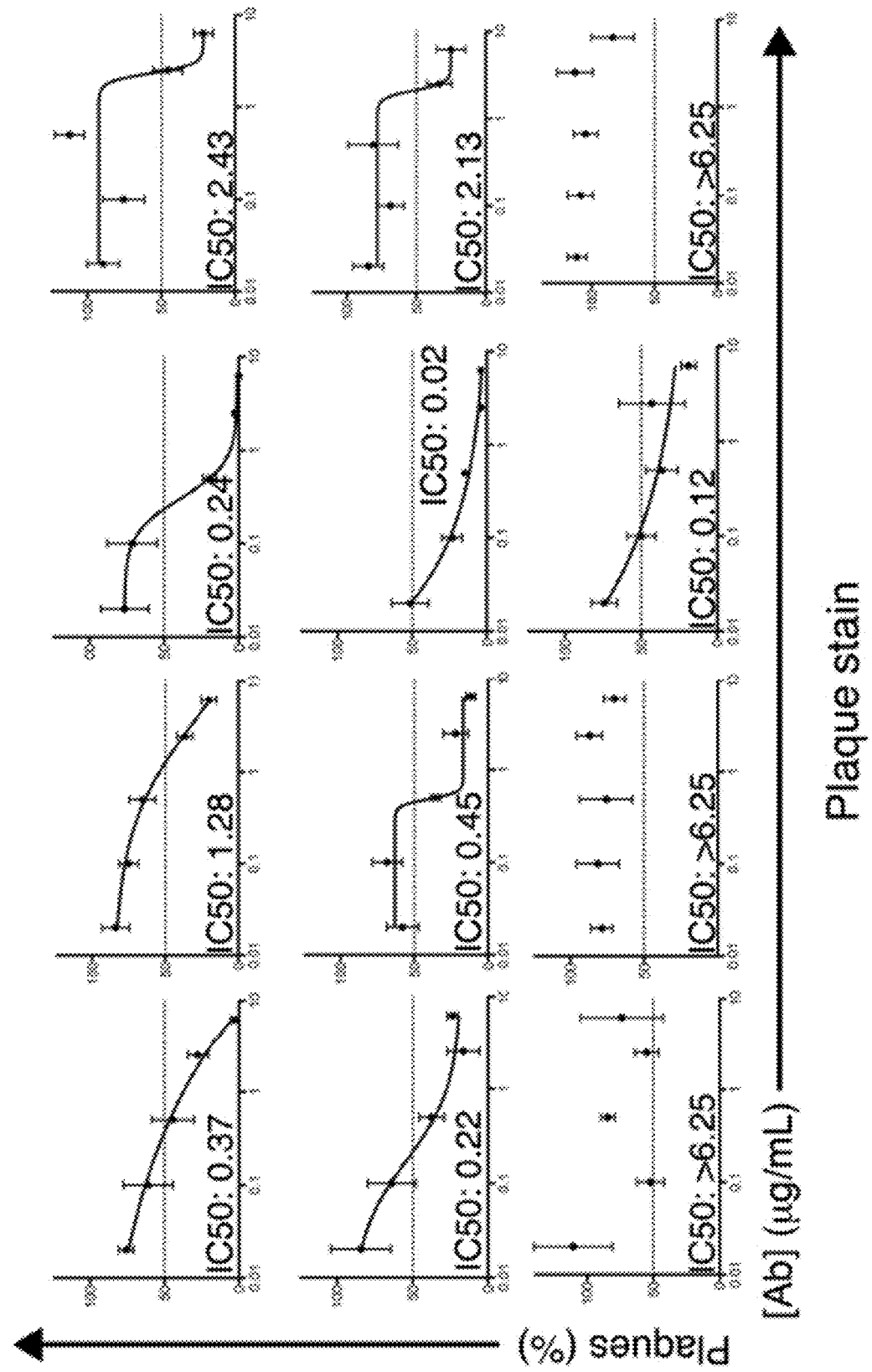
Figure 4D:
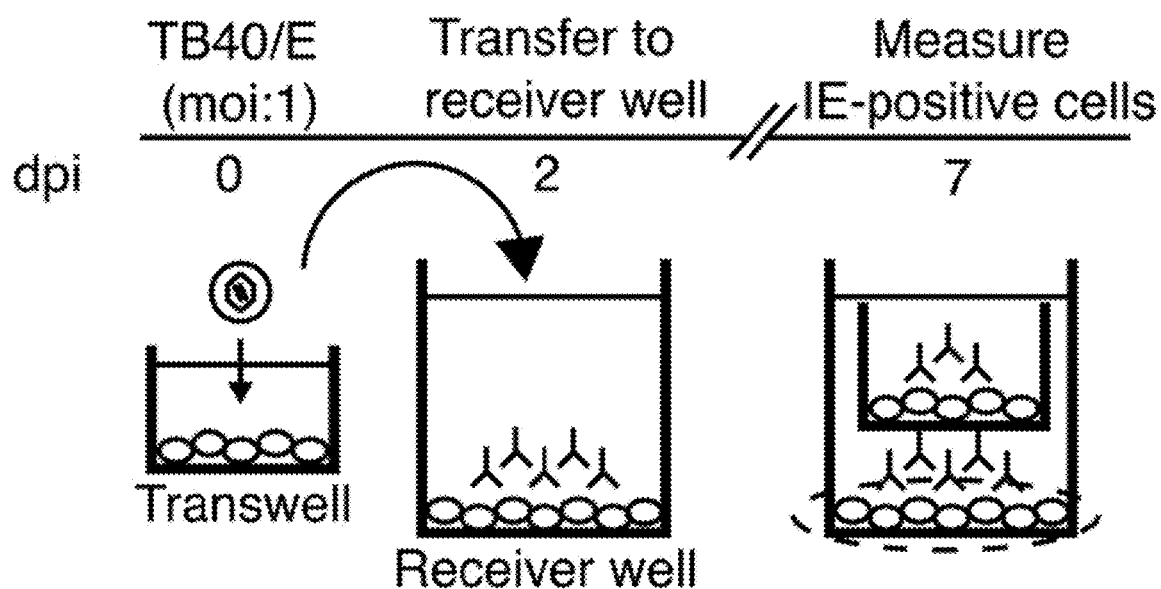
Figure 4E:
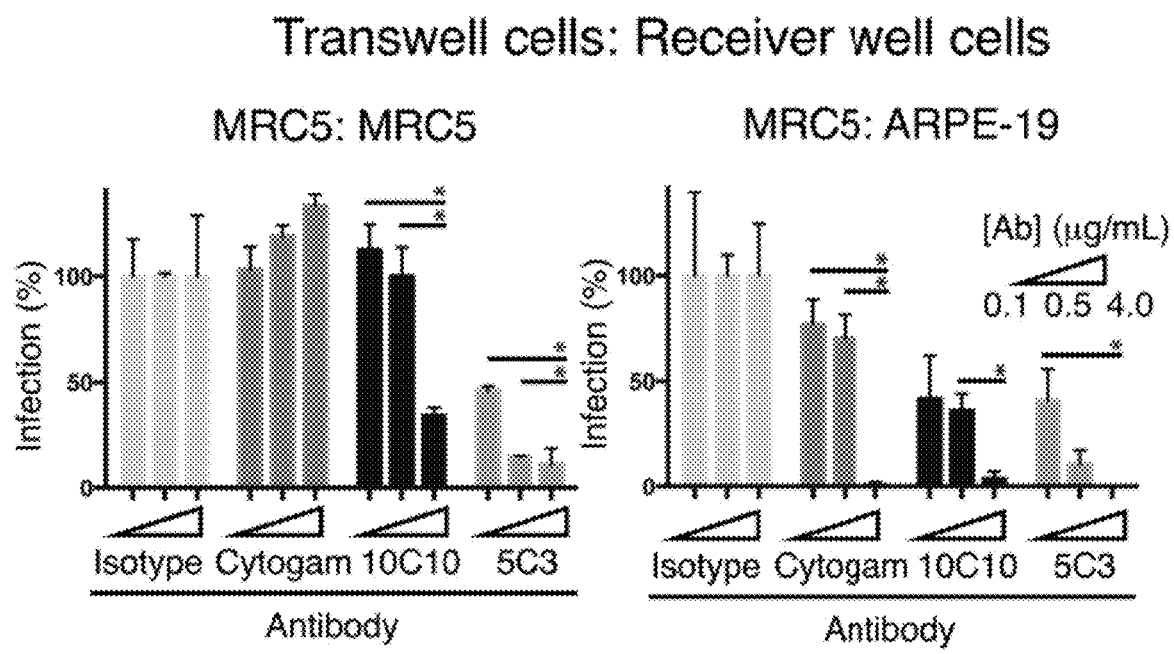
Figure 4F:
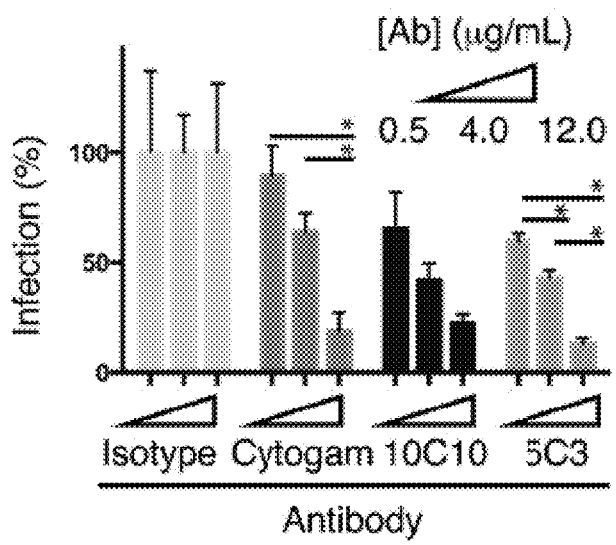
Figure 4G:
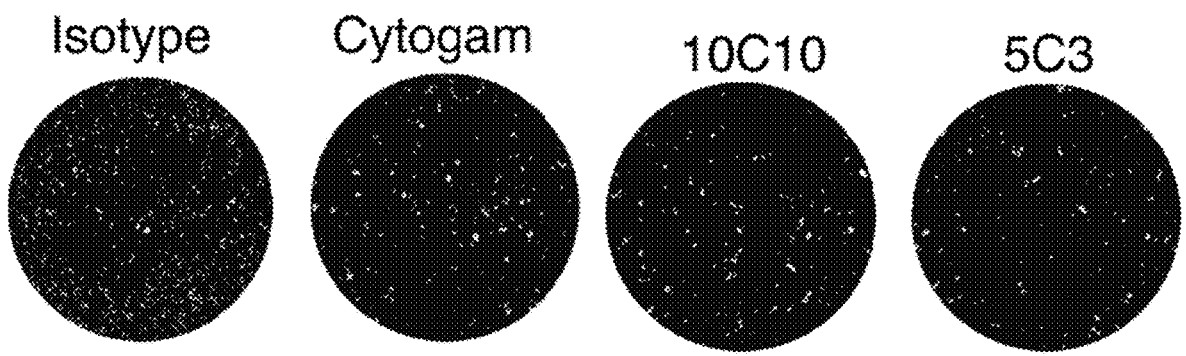

FIGS. 4A through 4G represent an examination of the potency and versatility of anti-gH mAbs in epithelial cells. FIG. 4A: Cytogam® and mAbs 10C10 and 5C3 were pre-incubated with HCMV strains AD169, TB40/E, VHL/E and TR (0.01-12 µg/mL), and subsequent infection levels of MRC5 cells was analyzed by immunostaining with anti-Immediate Early (IE) gene product ($\alpha$-IE$^{FITC}$) antibody. FIG. 4B: Cytogam® and mAbs 10C10 and 5C3 were pre-incubated with CMV strains DAVIS, TB40/E, VHL/E and TR (0.025-6.25 µg/mL), and subsequent infection levels of MRC5 cells was analyzed by plaque assay. FIG. 4C: Cytogam® and mAbs 10C10 and 5C3 were pre-incubated with HCMV strains TB40/E, VHL/E and TR (0.01-12 µg/mL), and subsequent infection levels of human retinal pigment epithelial cells (ARPE-19) was measured by anti-IE staining. Non-linear regression analysis was performed and the half maximal inhibitory concentration (IC50) was calculated for all antibodies under all conditions. FIG. 4D: MRC5 cells were seeded on a transwell insert with 3 µm pore and infected (moi: 1) with TB40/E. At 2 days post infection (dpi) the transwell insert was transferred to a receiver well containing an isotype control, Cytogam® or mAbs 10C10 and 5C3 (0.1-4 µg/mL) and at 7 dpi the cells from the receiver layer were analyzed by $\alpha$-IE$^{FITC}$ immunostain. FIG. 4E: MRC5 (left panel) and ARPE-19 (right panel) cells from the transwell infection experiment were analyzed for infection levels by $\alpha$-IE$^{FITC}$ immunostain. FIG. 4F: Infection levels of ARPE-19 cells infected with TB40/E (moi: 0.1) and exposed to an isotype control, Cytogam® or mAbs 10C10 and 5C3 (0.5-12 µg/mL) over a 10 day period were analyzed by $\alpha$-IE$^{FITC}$ immunostain. FIG. 4G: Fluorescent cytometer scanning analysis of ARPE-19 cells from FIG. 4F reveal fluorescent puncta representing IE-positive cells.

Figure 5B:
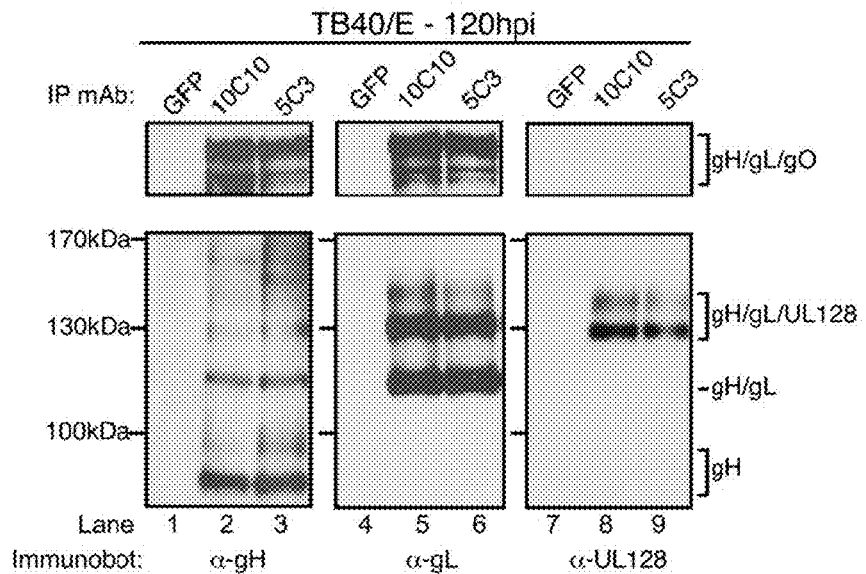
Figure 5C:
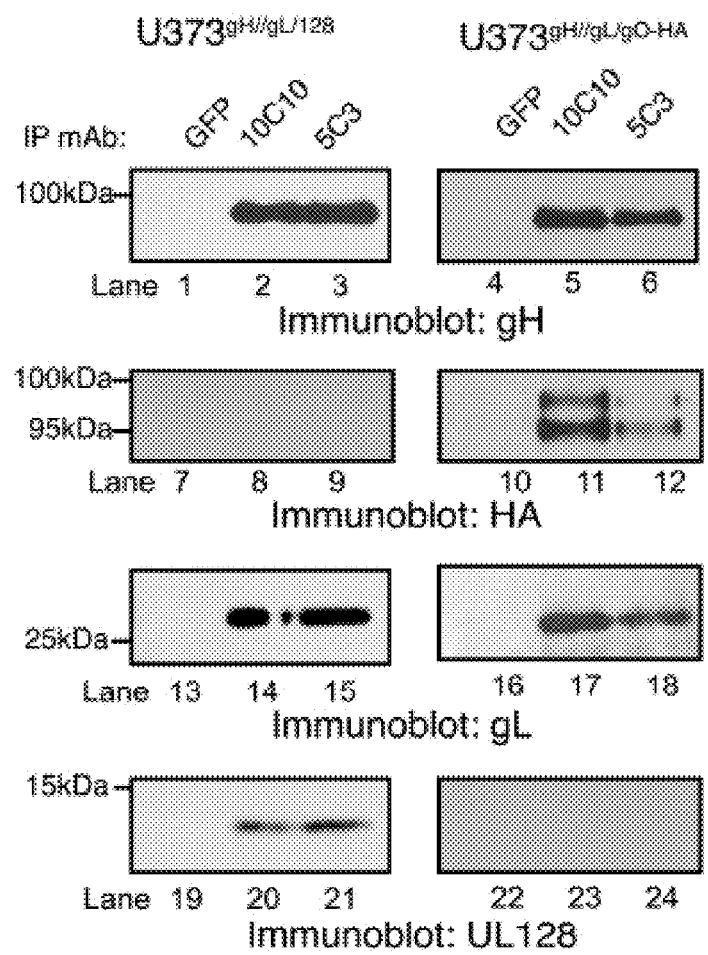
Figure 5D:
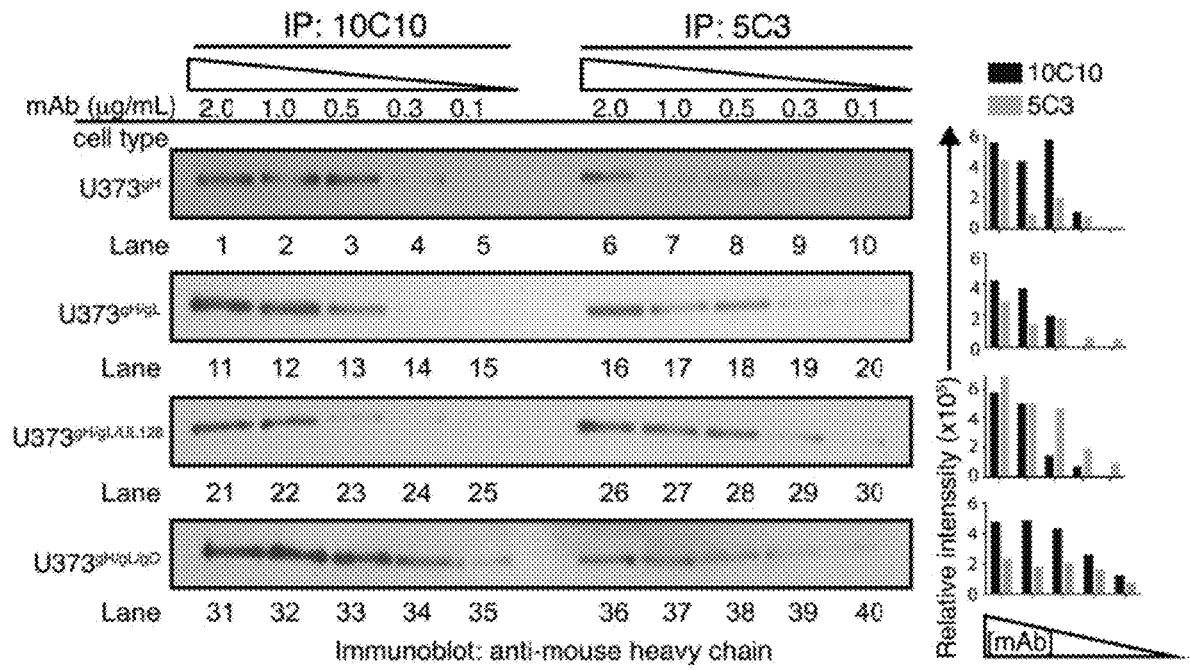
Figure 5E:
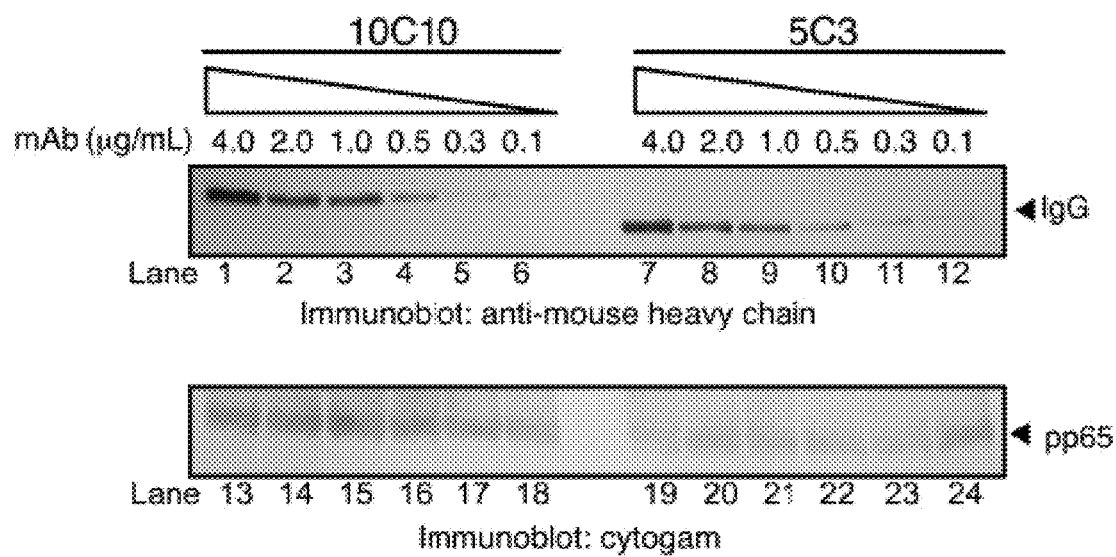
Figure 5G:
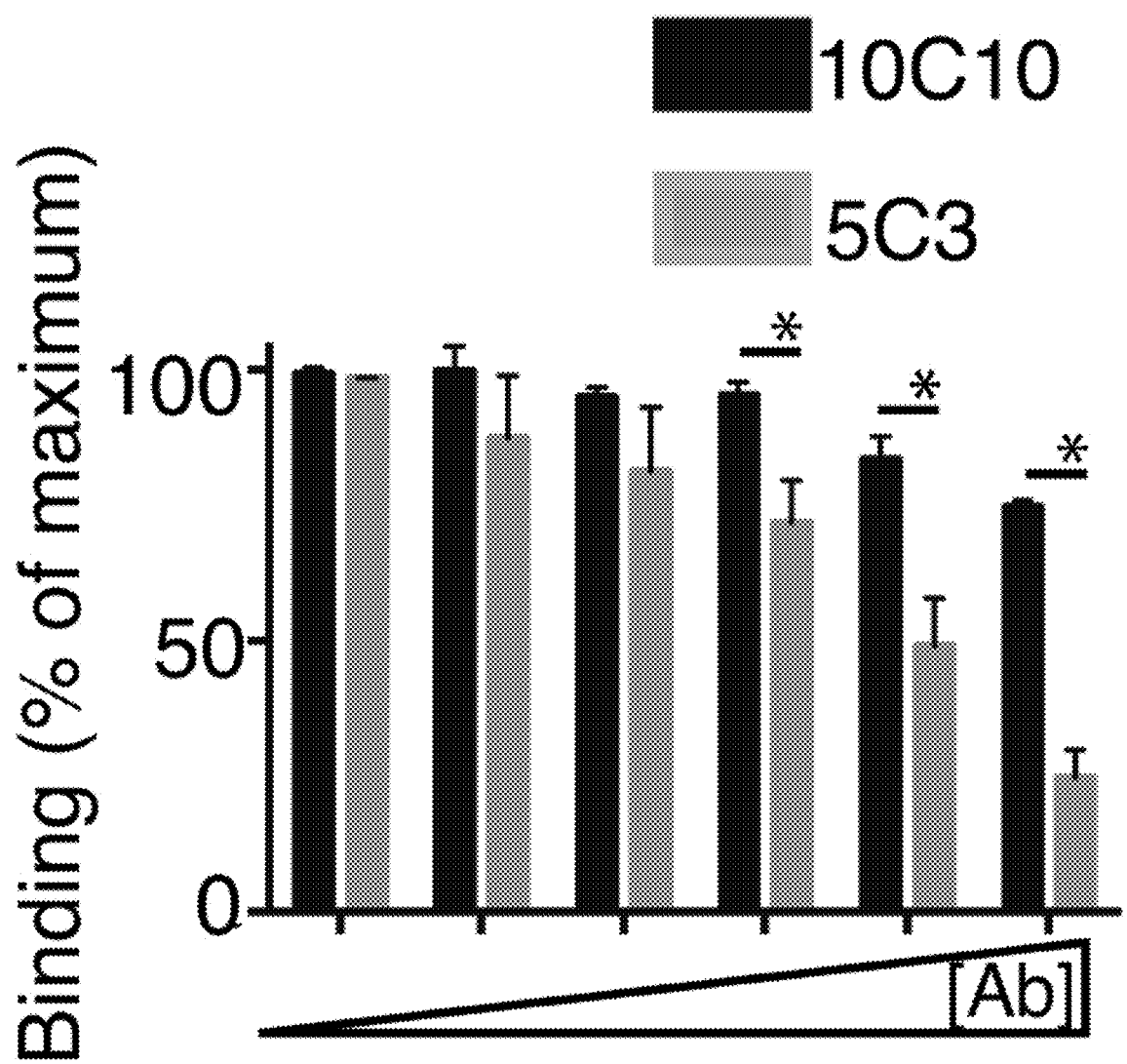

FIGS. 5A through 5G represent $\alpha$-gH mAbs bind to multiple glycoprotein complexes. FIG. 5A: Lysates from metabolically-labeled TB40/E-infected MRC5 cells were exposed to an isotype control mAb recognizing GFP, or mAb 10C10 and 5C3. Recovered immune complexes were split and treated with PNGase F, then resolved by non-reducing SDS-PAGE. Arrows denote the identity of glycosylated protein complexes and asterisks denote the identity of de-glycosylated protein complexes. FIG. 5B: Lysates from TB40/E-infected MRC5 cells were exposed to a GFP mAb, 10C10 or 5C3. Immune complexes were resolved by non-reducing SDS-PAGE followed by immunoblot for gH (Lanes 1-3), gL (Lanes 4-6), and UL128 (Lanes 7-9). Lines denote the glycoprotein complexes. FIG. 5C: Lysates from U373 cells stably expressing gH/gL/UL128 (U373$^{gH/gL/UL128}$) and gH/gL/gO-HA (U373$^{gH/gL/gO\text{-}HA}$) were exposed to GFP, 10C10, or 5C3 mAbs and the recovered immune complexes were resolved by SDS-PAGE and subjected to immunoblot for gH (Lanes 1-6), HA (Lanes 7-12), gL (Lanes 13-18), and UL128 (Lanes 19-24). FIG. 5D: Lysates from U373$^{gH}$ (Lanes 1-10), U373$^{gH/gL}$ (Lanes 11-20), U373$^{gH/gL/UL128}$ (Lanes 21-30), and U373$^{gH/gL/gO\text{-}HA}$ (Lanes 31-40) cells were exposed to 10C10 or 5C3 at various concentrations (0.1-2 µg/mL) and the resolved immune complexes were exposed to gH immunoblot. Densitometry values of the recovered gH are depicted (right column). FIG. 5E: TB40/E virus prep was incubated with varying concentration of mAb 10C10 and 5C3 (0.1-4 µg/mL). Virus/mAb complexes were then recovered by ultracentrifugation and total protein was resolved by SDS-PAGE, followed by immunoblot for anti-mouse heavy and light chain (Lanes 1-12) or Cytogam® (Lanes 13-24). IgG and pp65 are indicated by arrows. Average densitometry values of the pp65:IgG ratio from 3 independent experiments are depicted (right column). FIG. 5F: U373$^{gH/gL}$ cells were left unstained (gray peak) or were labeled with mAbs 10C10 (top row) and 5C3 (bottom row) conjugated to an Alexa647 fluorophore (10C10$^{647}$ and 5C3$^{647}$), together with increasing concentrations of non-conjugated 10C10 or 5C3 (1-20 µg/mL) (white peaks). FIG. 5G: The % of cells stained by 5C3$^{647}$ in the presence of non-labeled 10C10 (black bars) or non-labeled 5C3 (gray bars) is depicted for all concentrations.

Figure 6A:
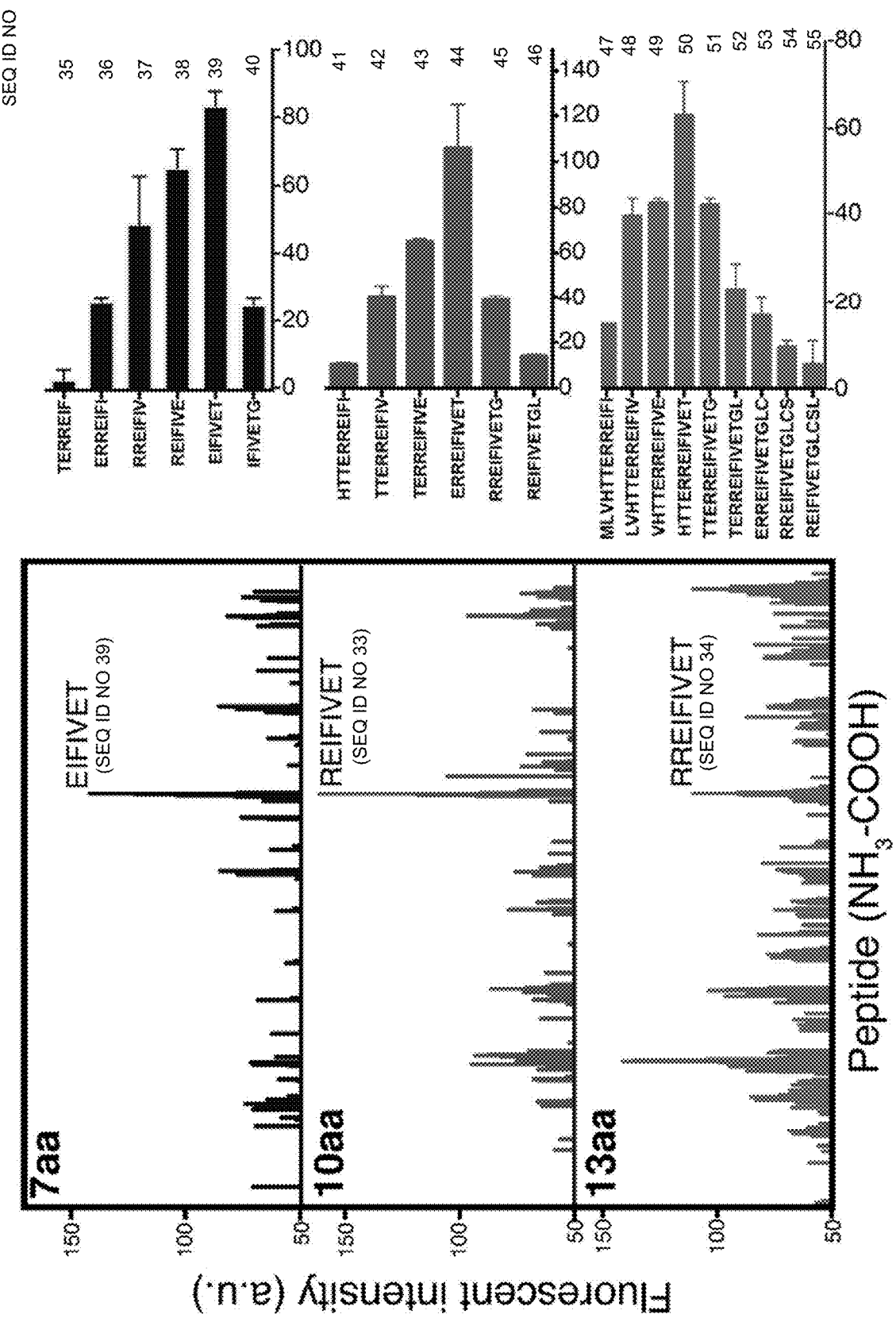
Figure 6F:
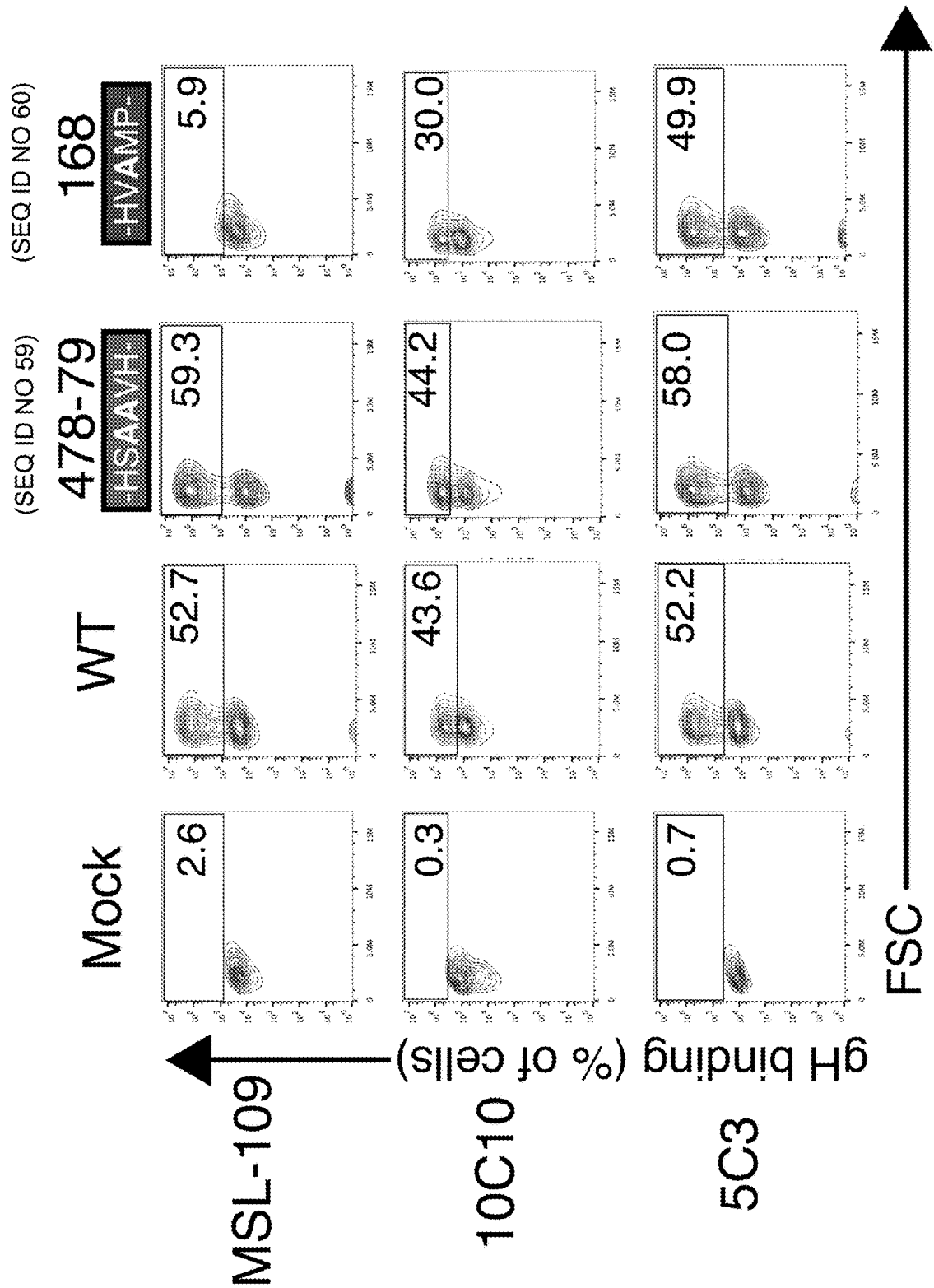
Figures 6G, 6H:
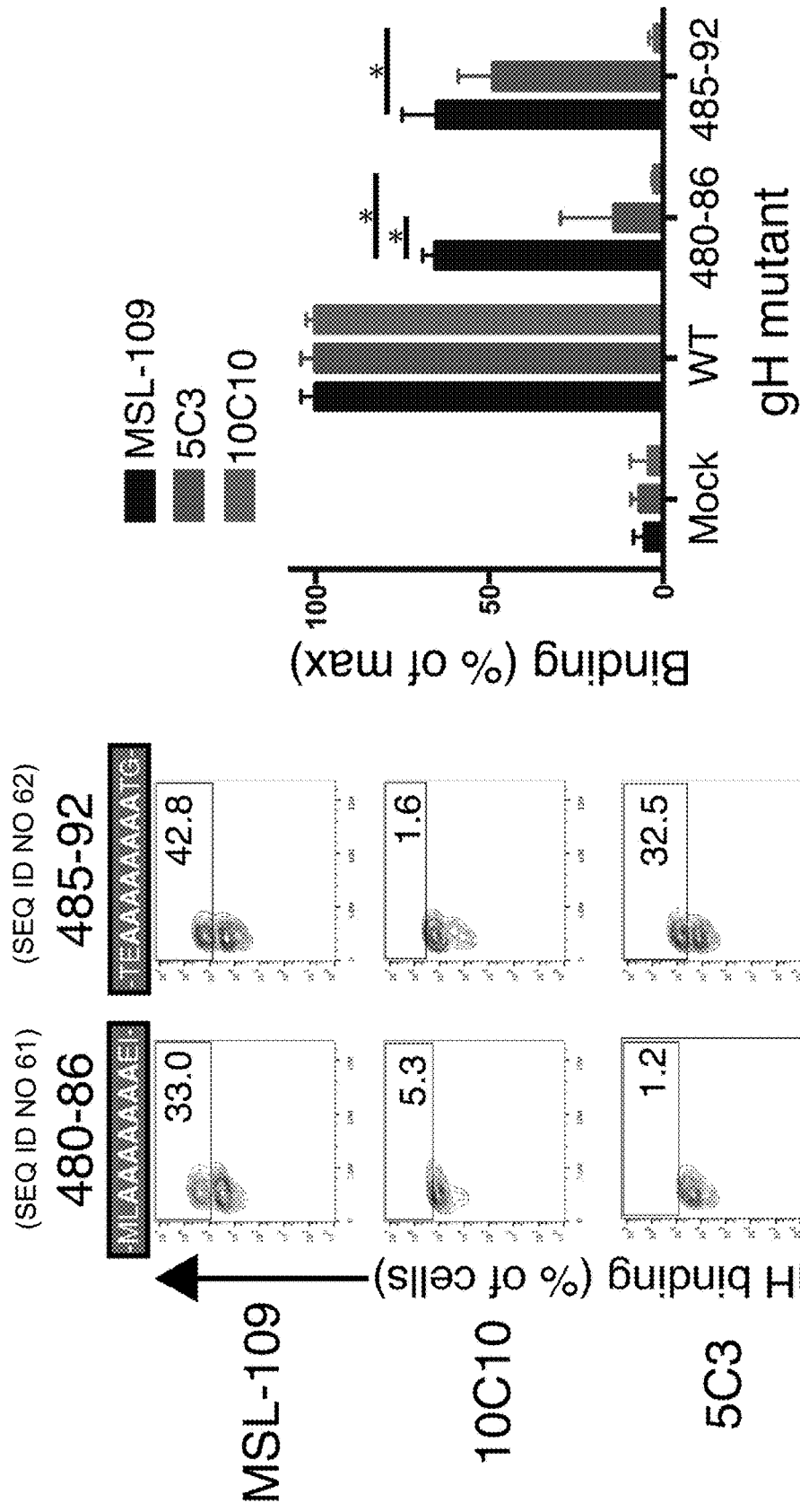

FIGS. 6A through 6J represent the identification of α-gH mAb epitopes. FIG. 6A: Spot intensities were quantified following incubation of mAb 5C3 followed by an anti-mouse Dylight680 mAb with overlapping conformational gH peptide libraries of 7 amino acids (aa), 10aa, and 13aa (Left panel). Reactivity of mAb 5C3 with overlapping peptide series near the region of peak binding are shown for each library (Right panel). FIG. 6B: The region of 5C3 reactivity is located between aa's 481-495 within domain 2 of HCMV gH. The 5C3-reactive region includes a β-sheet and a 10aa long alphahelical region. FIG. 6C: The putative 5C3 epitope amino acid 485-496 region was predicted to exist within an alphahelical region spanning amino acids 485-496 in HCMV-gH. FIG. 6D. Structural modeling of the HCMV-gH protein based on the crystal structure of HSV-1 indicates the location of the putative 5C3 epitope region FIG. 6E: Predicted surface interactions indicate that the 5C3-reactive alpha helical region is exposed on the surface of gH (circle). FIG. 6F: HEK293 cells transfected with gL and a transfection control (first column), wildtype (WT) gH (second column), gH mutant 478-79 (third column), or gH mutant 168 (fourth column) were stained with MSL-109 (top row), 10C10 (middle row), or 5C3 (bottom row). Percent (%) of cells positive for gH are indicated. FIG. 6G: HEK293 cells were transfected with gL and gH mutant 480-86 (first column) or gH mutant 485-92 (second column) and stained with MSL-109 (top row), 10C10 (middle row), or 5C3 (bottom row). Percent (%) of cells positive for gH are indicated. FIG. 6H: The data from FIG. 6G was quantified and normalized compared to WT staining levels. FIG. 6I: Binding of MSL-109, 5C3, and 10C10 to 293 cells transfected with gH containing 2aa alanine substitutions along the length of the epitope region was measured. Percent (%) of gH-positive cells compared to WT transfected cells was calculated and plotted. FIG. 6J: The epitope region from 12 geographically distinct HCMV strains were aligned to the TB40/E sequence.

Figure 7:
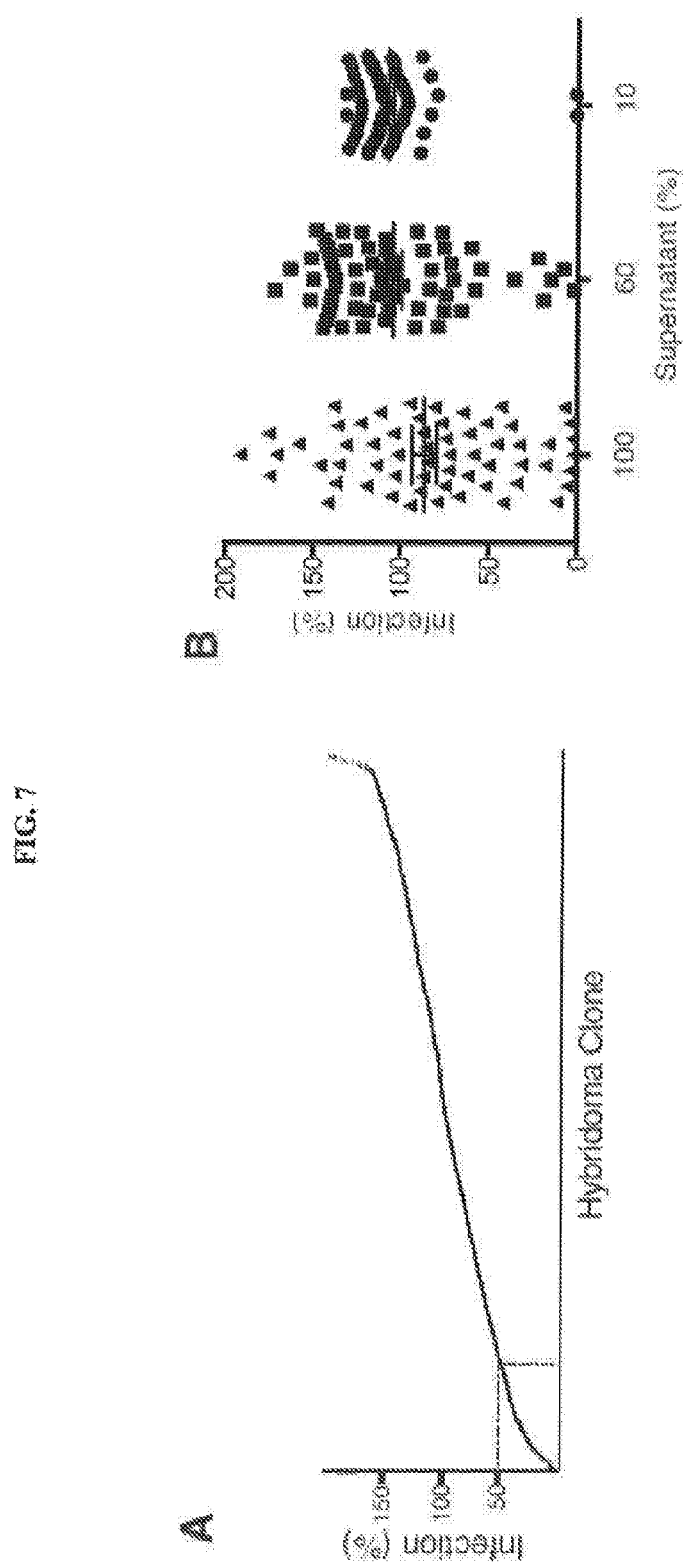

FIGS. 7A and 7B represent identification of HCMV-neutralizing antibodies by hybridoma screening. FIG. 7A: Supernatant from approximately 2000 murine hybridomas were tested for their ability to neutralize HCMV infection of MRC5 fibroblasts with AD1691E2-YFP following pre-incubation with virus. All samples were normalized as percent (%) infection compared to the median value for all samples. Dotted line represents the 50% infection cutoff used to select hybridomas for further screening. FIG. 7B: Hybridoma supernatants from the clones that reduced infection by 50% were screened at 100%, 50%, or 10% hybridoma supernatant concentration and normalized to the median of all samples tested.

Figure 8A:
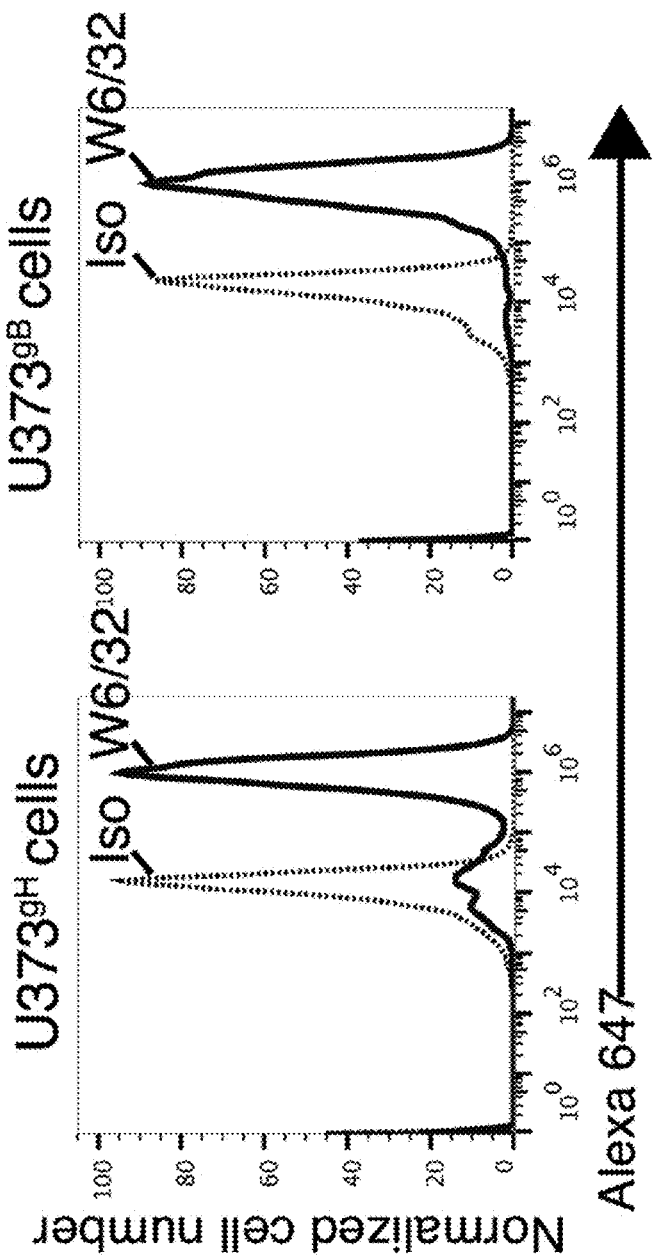
Figure 8B:
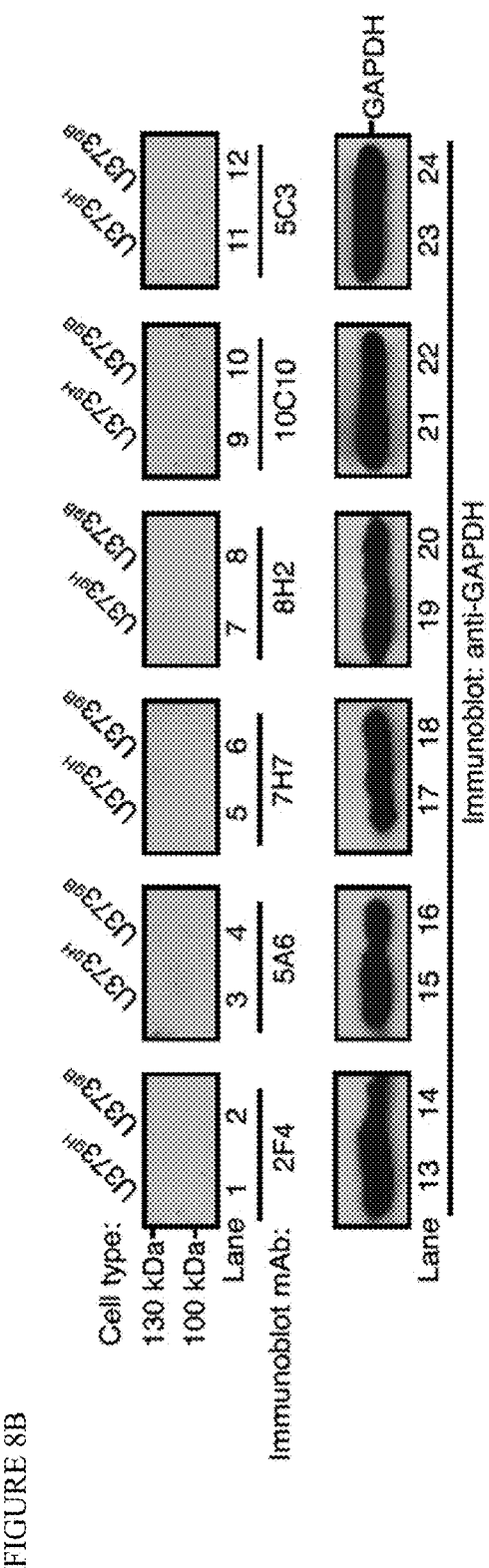

FIGS. 8A and 8B represent examination of HCMV neutralizing mAb targets. FIG. 8A: U373gH (left panel) and U373gB cells (right panel) were permeabilized and stained with an IgG2a isotype control (dotted line) or an antibody recognizing properly folded MEW class I molecules (W6/32) (solid line) followed by flow cytometry analysis. FIG. 8B: Lysates from U373gH or U272gB cells were resolved by SDS-PAGE and exposed to immunoblot with HCMV-neutralizing antibodies (lanes 1-2) or GAPDG (lanes 13-24). Relative molecular mass markers are indicated.

Figure 9A:
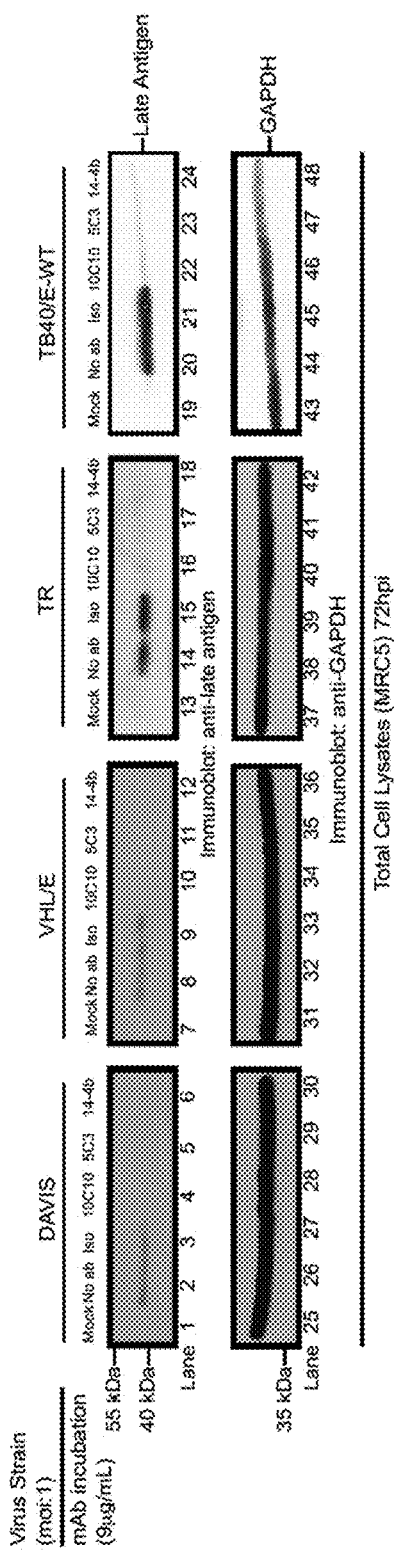
Figure 9B:
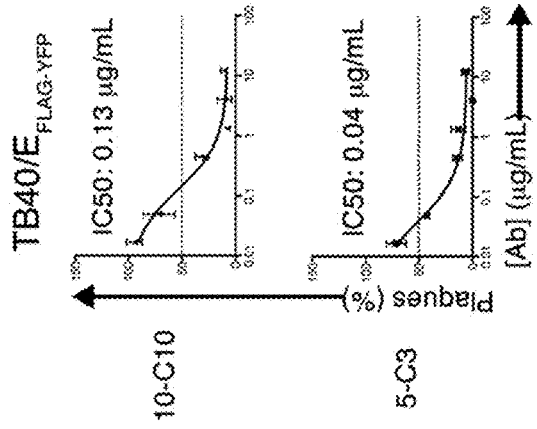

FIGS. 9A and 9B represent neutralization of clinical-like HCMV strains by anti-gH antibodies. FIG. 9A: Total lysates from MRC5 cells infected with HCMV strains DAVIS (first panel), VHL/E (second panel), TR (third panel), or TB40/E (fourth panel) following incubation with or without an isotype control or anti-gH mAbs 10C10 and 5C3 were resolved by SDS-PAGE and exposed to immunoblot for HCMV late antigen (top row) or GAPDH (bottom panel). Relative molecular mass markers are indicated. FIG. 9B: mAbs 10C10 and 5C3 were pre-incubated with TB40/EFLAG-YFP (0.01-12 µg/mL), and subsequent infection levels of ARPE-19 cells were measured by YFP fluorescence levels. IC50 values are indicated.

Figure 10A:
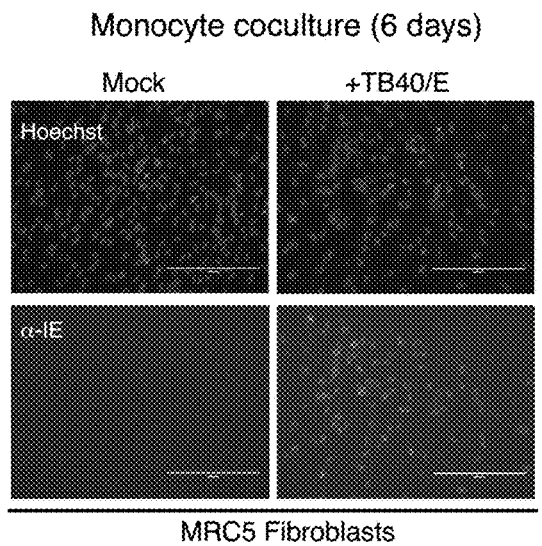
Figure 10B:
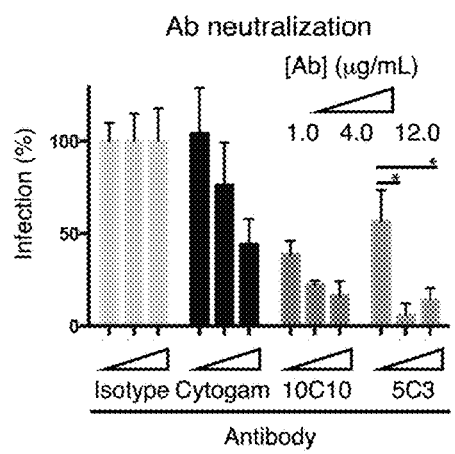

FIGS. 10A and 10B represent that anti-gH antibodies block monocyte-fibroblast dissemination. FIG. 10A: Fibroblasts cocultured for 6 days with CD14+ monocytes that were either mock infected or infected with TB40/E were analyzed by fluorescence microscopy for presence of anti immediate early gene product (α-IEFITC) (bottom row). Hoechst reagent permitted visualization of the nucleus (top row). FIG. 10B: The highest number of α-IEFITC-positive fibroblasts/well following infected monocyte coculture or mock-infected monocyte coculture was quantified by fluorescent cytometer. The number of α-IEFITC-positive fibroblasts/well following coculture with infected or mock-infected monocytes in presence of various concentrations (1-12 µg/mL) of Cytogam® or mAbs 10C10 or 5C3 was quantified by fluorescent cytometer. Error bars represent standard deviation and the data is averaged across three independent experiments.

Figure 11A:
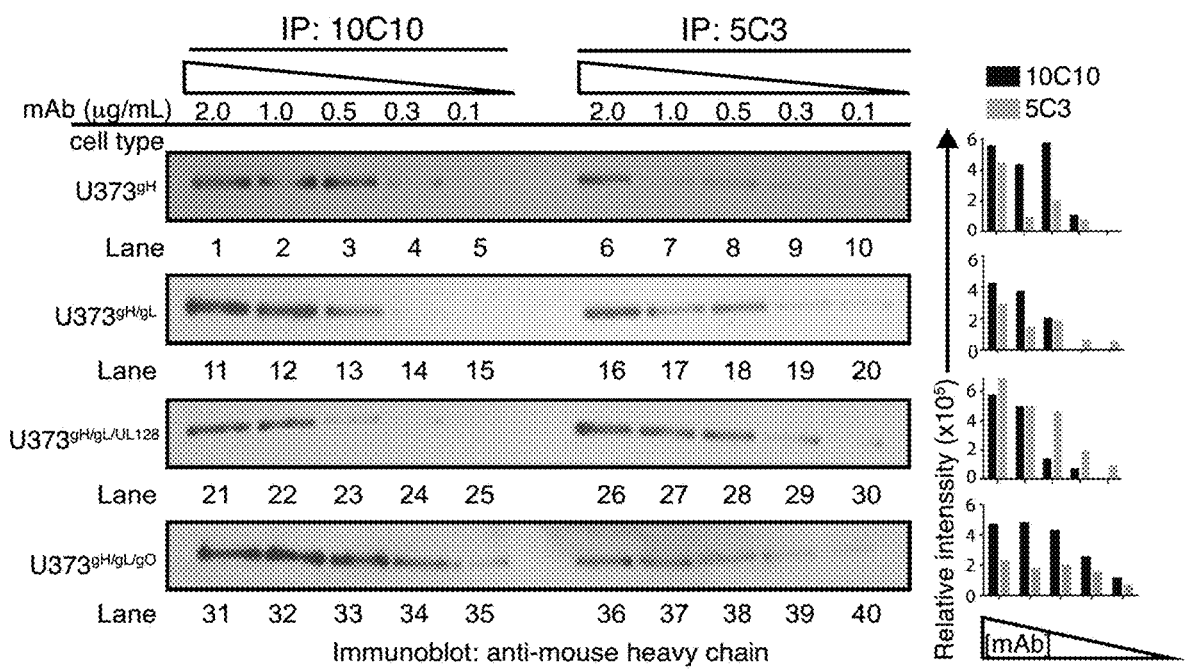
Figure 11B:
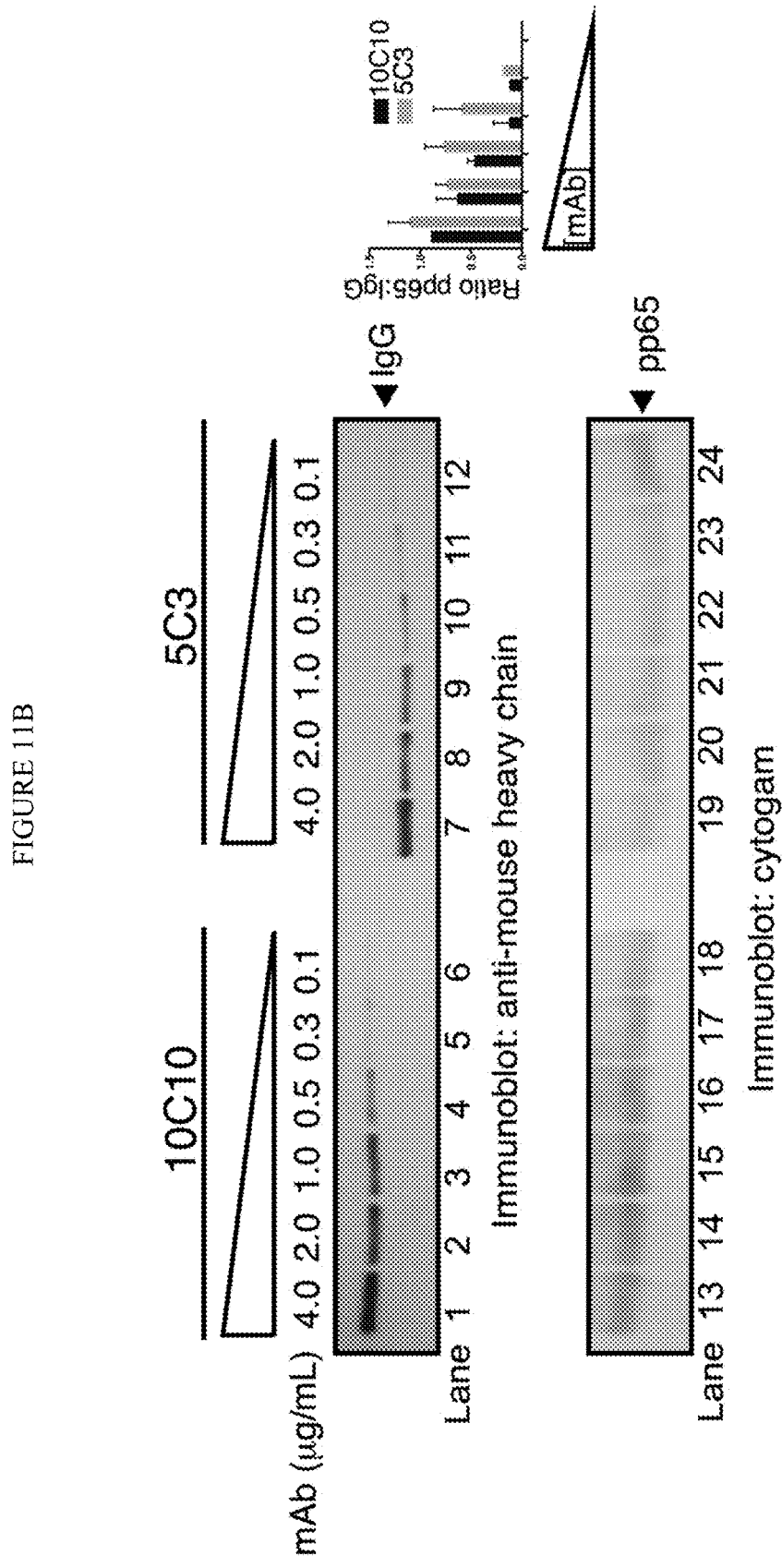

FIGS. 11A and 11B represent that 10C10 and 5C3 display variable preferences for gH protein complexes. FIG. 11A: Lysates from U373gH (lanes 1-10), U373gH/g: (lanes 11-20), U373gH/gL/gO-HA (lanes 31-40) cells were exposed to 10C10 or 5C3 at various concentrations (0.1 to 2 µg/mL) and the resolved immune complexes were exposed to gH immunoblot. Densitometry values of the recovered gH are depicted (right column). FIG. 11B: TB40/E virus prep was incubated with varying concentration of mAb 10C10 and 5C3 (0.1-4 µg/mL). Virus/mAb complexes were then recovered by ultracentrifugation and total protein was resolved by SDS-PAGE, followed by immunoblot for anti-mouse heavy and light chain (lanes 1-12) or Cytogam® (lanes 13-24). IgG and pp65 are indicated by arrows. Average densitometry values of the pp65:IgG ratio from three independent experiments are depicted (right column).

Figures 12A, 12B, 12C:
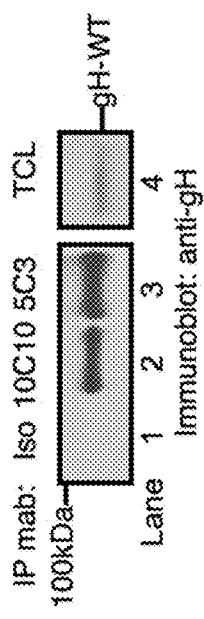

FIGS. 12A through 12E represent binding of truncated gH constructs by 10C10 and 5C3. A series of N-terminal (FIG. 12A) and C-terminal (FIG. 12B) truncation constructs were generated. FIG. 12C: Conditions for optimal gH transfection and immunoprecipitation from 293 cells were established for the WT gH construct. Cell lysates from gH WT-transfected cells were exposed to an isotype control (lane 1) or mAbs 10C10 (lane 2) and 5C3 (lane 3). Recovered immune complexes were immunoblotted with an anti-gH protein. Total cell lysates demonstrated the proper expression of the gH protein (lane 4). FIG. 12D: gH N-terminal constructs and gH C-terminal constructs (FIG. 12E) were transfected into HEK293 cells. Total cell lysates were exposed to immunoprecipitation with an isotype control or mAbs 10C10 and 5C3. Immunoblot was performed with an anti-HA antibody. Total cell lysates demonstrated the proper expression of the gH mutant. Relative molecular mass markers are indicated.

Figure 13:
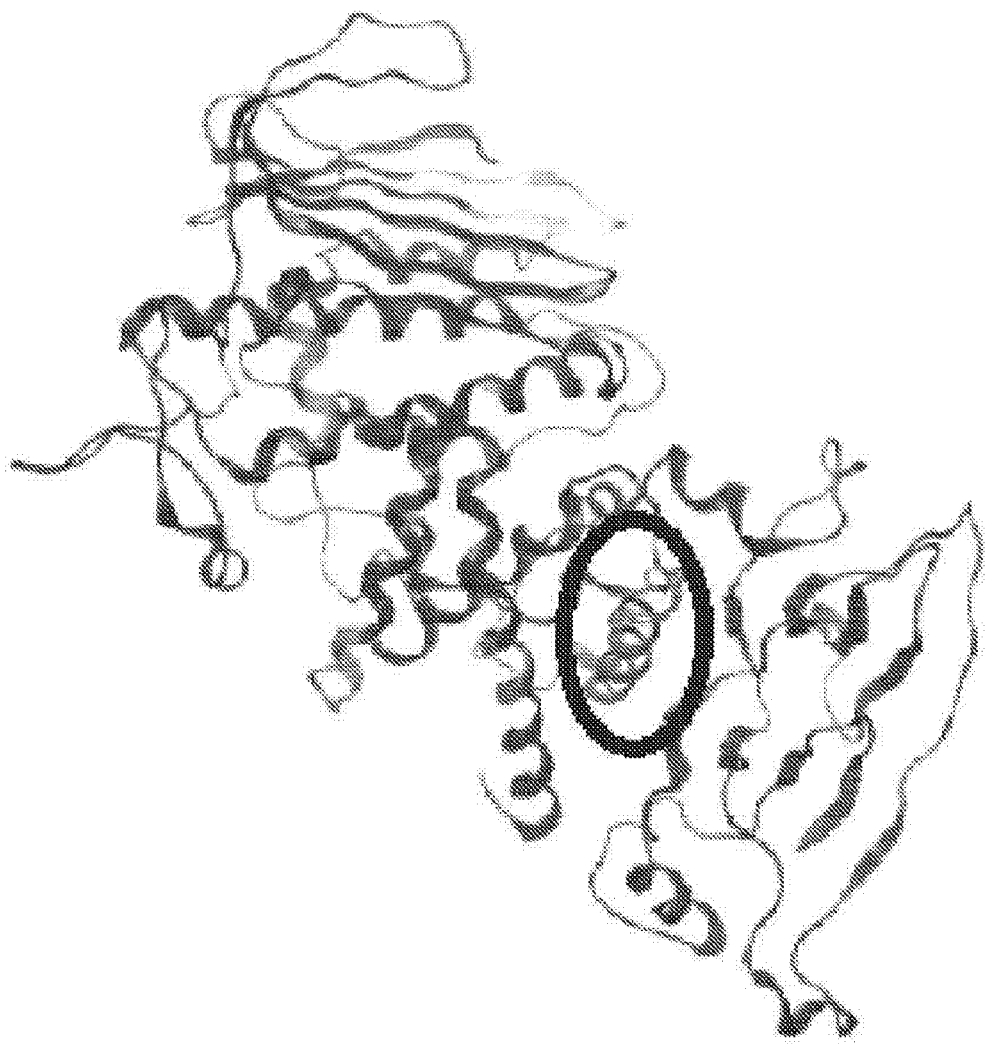

FIG. 13 represents a 3D gH epitope map. A ribbon model of the predicated HCMV-gH structure based on the crystallized HSV-1 gH/gL complex is depicted. The known interaction sites of the anti-gH HCMV-neutralizing antibodies are shown; the epitope region for 10C10 and 5C3 is circled.

Figure 14B:
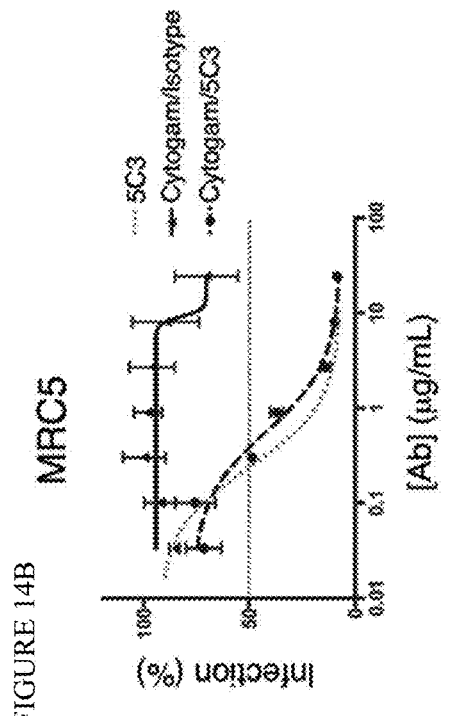
Figure 14C:
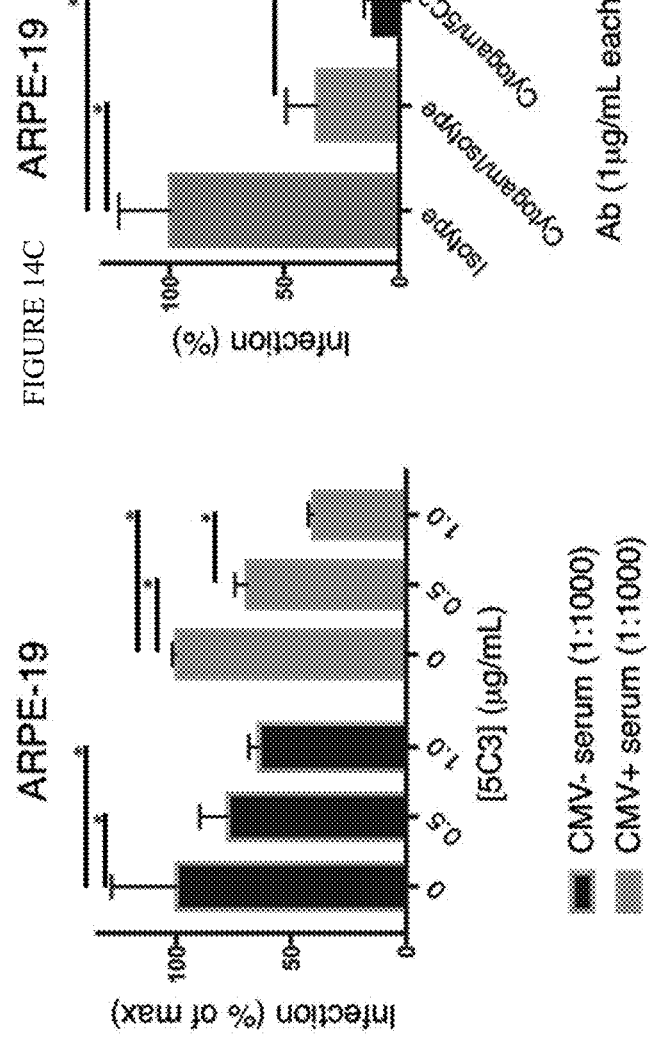
Figure 14A:
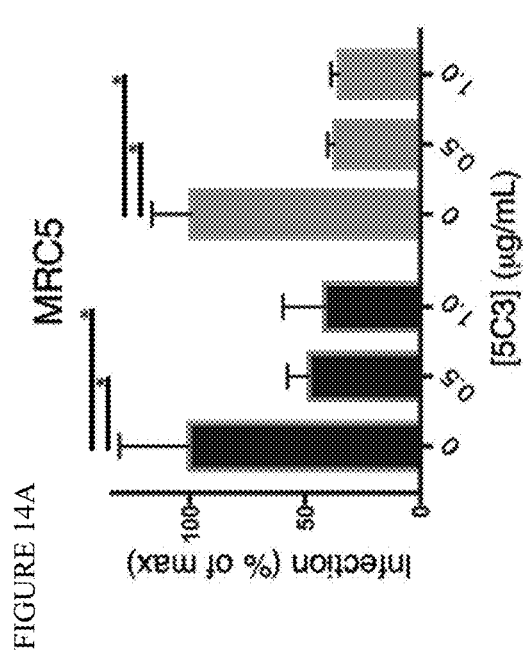

FIGS. 14A through 14C represents that anti-gH mabs supplement pre-existing HCMV immunity. FIG. 14A: Serum from HCMV-negative (black bars) or HCMV-positive (gray bars) pregnant women was tested for its ability to neutralize a TB40/E infection with various concentrations of mAb 5C3 (0-1 µg/mL) or ARPE-19 (bottom panel) cells. FIG. 14B: Cytogam® was combined with an equal concentration of an isotype control (solid line) or mAb 5C3 (dotted line), and pre-incubated with AD169IE2-YFP at multiple concentrations (0.02-12 µg/mL for each respective antibody). FIG. 14C: Antibody cocktails containing 1 µg/mL of Cytogam® with 1 µg/mL of an isotype control, or Cytogam® with mAb 5C3 were tested for their ability to neutralize TB40/FLAG-YFP infection of ARPE-19 cells

VI. DETAILED DESCRIPTION

A. Definitions

Unless otherwise defined, terms and definitions herein shall be accorded their plain meaning as to one of ordinary skill in the art.

An anti-HCMV antibody may take one of numerous forms in the art, as disclosed herein. Antibodies are in part defined by the antigens to which they bind, thus, an "anti-HCMV antibody" is any such antibody which specifically binds at least one epitope found on the viral envelope of human cytomegalovirus (HCMV) as described herein. It is understood in the art that an antibody is a glycoprotein comprising at least two heavy (H) chains and two light (L) chains inter-connected by disulfide bonds, or an antigen binding portion thereof. A heavy chain is comprised of a heavy chain variable region (VH) and a heavy chain constant region (CH1, CH2 and CH3). A light chain is comprised of a light chain variable region (VL) and a light chain constant region (CL). The variable regions of both the heavy and light chains comprise framework regions (FWR) and complementarity determining regions (CDR, e.g. CDRH1, CDRH2, CDRH3, CDRL1, CDRL2, and CDRL3). The four FWR regions are relatively conserved while CDR regions (CDR1, CDR2 and CDR3) represent hypervariable regions and are arranged from $NH_2$ terminus to the COOH terminus as follows: FWR1, CDR1, FWR2, CDR2, FWR3, CDR3, FWR4. The variable regions of the heavy and light chains contain a binding domain that interacts with an antigen while, depending of the isotype, the constant region(s) may mediate the binding of the immunoglobulin to host tissues or factors. It is known in the art that it is possible to manipulate monoclonal and other antibodies and use techniques of recombinant DNA technology to produce other antibodies or chimeric molecules which retain the specificity of the original antibody. Such techniques may evolve introducing DNA encoding the immunoglobulin variable region, or CDRs, of an antibody to the constant regions, or constant regions plus framework regions, of a different immunoglobulin.

The term "antibody" (Ab) as used herein is used in the broadest sense and specifically may include any immunoglobulin, whether natural or partly or wholly synthetically produced, including but not limited to monoclonal antibodies, polyclonal antibodies, multispecific antibodies (for example, bispecific antibodies and polyreactive antibodies), and antibody fragments. Thus, the term "antibody" as used in any context within this specification is meant to include, but not be limited to, any specific binding member, immunoglobulin class and/or isotype (e.g., IgG1, IgG2a, IgG2b, IgG3, IgG4, IgM, IgA1, IgA2, IgD, and IgE) and biologically relevant fragment or specific binding member thereof, including but not limited to Fab, F(ab')$_2$, scFv (single chain or related entity), and (scFv)$_2$.

The term "antibody fragments" as used herein may include those antibody fragments obtained using techniques readily known and available to those of ordinary skill in the art, as reviewed herein. Therefore, in addition to the definition for "antibody" presented supra, the term "antibody" may further encompass any polypeptide or protein comprising a portion of an intact antibody, such as the antigen binding or variable region of the intact antibody. These can be derived from natural sources, or they may be partly or wholly synthetically produced. Examples of antibody fragments include, but are not limited to, Fab, Fab', F(ab')2, and Fv fragments; diabodies, linear antibodies, and single-domain antibodies (sdAb).

The term "monoclonal antibody" or "mAb" as used herein may refer to an antibody obtained from a population of substantially homogeneous antibodies, i.e., the individual antibodies comprising the population are identical except for possible naturally occurring mutations that may be present in minor amounts.

The term "core binding region" as used herein refers to the peptide sequence VHTTERREIFIVETG (SEQ ID NO: 1), which is located on the full-length consensus sequence of HCMV glycoprotein gH, reproduced as SEQ ID NO: 2 herein. Several embodiments of the present disclosure are directed to anti-HCMV antibodies that specifically bind to one or more epitopes within SEQ ID NO: 1 and their methods of use thereof, exemplified by, but expressly not limited to, the monoclonal anti-HCMV antibodies 10C10 and 5C3. The anti-HCMV antibodies of the present disclosure may bind to one or more epitopes within the core binding region, and the epitopes need not be the full length of the core binding region, nor do the epitopes need to be fully linear (although they may be); the epitopes, such as is believed to be the case of 10C10 and 5C3, may be conformational and thus non-linear (discontinuous). Furthermore, an anti-HCMV antibody may bind partially within the core binding region and partially outside, especially in the case of a conformational epitope, although in many circumstances it will bind wholly inside the core binding region; in either case, such antibodies are expressly intended to be covered by this invention. Some antibodies, e.g. polyclonal antibodies, in addition to binding within the core binding region, may additionally bind to epitopes entirely outside of the core binding region. So long as they specifically bind within the core binding region, including binding partially within the core binding region and partially outside (again particularly in the case of a conformational epitope), such antibodies are expressly intended to covered by this invention. Furthermore, although the core binding region exhibits a high degree of conservation among different HCMV strains, thus owing partially to its ability to serve as a target for broadly neutralizing antibodies, one of ordinary skill in the art will appreciate that conservative substitutions may be made to SEQ ID NO: 1, and antibodies that bind to one or more epitopes within SEQ ID NO: 1 having conservative substitutions are also expressly intended to be covered by the present disclosure.

The terms "conservative sequence modifications" or "conservative substitutions" as used herein may refer to amino acid modifications to a target epitope of the invention that do not significantly affect or alter the binding characteristics of the anti-HCMV antibodies to the epitope(s). Such conservative modifications include amino acid substitutions, additions and deletions. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within a target epitope that the anti-HCMV antibodies of the invention specifically bind to, e.g. epitopes on the viral envelope of HCMV, can be replaced with other amino acid residues from the same side chain family and the antibodies of the present disclosure can be tested against the target epitope can be tested, for example using functional assays described herein or otherwise known in the art.

The term "biological sample" as used herein may refer to a sample obtained from an organism (e.g., patient) or from components (e.g., cells) of an organism. The sample may be of any biological tissue, cell(s) or fluid. The sample may be a "clinical sample" which is a sample derived from a subject, such as a human patient. Such samples include, but are not limited to, saliva, sputum, blood, blood cells (e.g., white cells), bodily fluids, lavages, pancreatic juices, gastric juices, discharges, CSF, lymph amniotic fluid, plasma, semen, bone marrow, and tissue or fine needle biopsy samples, urine, stool, peritoneal fluid, and pleural fluid, or cells therefrom, and any combinations thereof. Biological samples may also include sections of tissues such as frozen sections taken for histological purposes. A biological sample may also be referred to as a "patient sample." A biological sample may also include a substantially purified or isolated protein, membrane preparation, or cell culture.

The terms "effective amount" or "therapeutically effective amount" as used herein may refer to an amount of the compound or agent that is capable of producing a medically desirable result in a treated subject. The treatment method can be performed in vivo or ex vivo, alone or in conjunction with other drugs or therapy. A therapeutically effective amount can be administered in one or more administrations, applications or dosages and is not intended to be limited to a particular formulation or administration route.

The terms "antigen binding portion", "antigen binding fragment" or "Fab" as used herein may refer to a region on an antibody that binds to antigens. One of ordinary skill in the art will understand that Fabs are comprised of one constant one variable domain of each of the heavy and light chain of an antibody.

The terms "specific binding," "selective binding," "selectively binds," and "specifically binds," may refer to antibody binding to an epitope on a predetermined antigen but not to other antigens. Typically, the antibody binds with an equilibrium dissociation constant ($K_D$) of approximately less than $10^{-6}$ M, such as approximately less than $10^{-7}$ M, $10^{-8}$ M, $10^{-9}$ M or $10^{-10}$ M or even lower when determined by, e.g., equilibrium dialysis or surface plasmon resonance (SPR) technology in, for example, a BIACORE® 2000 surface plasmon resonance instrument or similar technology using the predetermined antigen, e.g., an epitope on the viral envelope of HCMV, as the analyte and the antibody as the ligand, or Scatchard analysis of binding of the antibody to antigen positive cells, and (ii) binds to the predetermined antigen with an affinity that is at least two-fold greater than its affinity for binding to a non-specific antigen (e.g., BSA, casein) other than the predetermined antigen or a closely-related antigen.

The term "homology" as used herein may refer to the existence of shared structure between two compositions. The term "homology" in the context of proteins may refer to the amount (e.g. expressed in a percentage) of overlap between two or more amino acid and/or peptide sequences. In the context of nucleic acids, the term may refer to the amount (e.g. expressed in a percentage) of overlap between two or more nucleic acid sequences. As used herein, the percent (%) homology between two sequences is equivalent to the percent identity between the two sequences. The percent identity between the two sequences is a function of the number of identical positions shared by the sequences (i.e., % homology=#of identical positions/total #of positions×100), taking into account the number of gaps, and the length of each gap, which need to be introduced for optimal alignment of the two sequences. The comparison of sequences and determination of percent identity between two sequences can be accomplished using a mathematical algorithm. Such homology is well-represented in the art via local alignment tools and/or algorithms, and may include pairwise alignment, multiple sequence alignment methods, structural alignment methods, and/or phylogenetic analysis methods.

The terms "co-administration," "co-administered," and "in combination with" as used herein may refer to the administration of at least two agents or therapies to a subject. In some embodiments, the co-administration of two or more agents/therapies is concurrent. In other embodiments, a first agent/therapy is administered prior to a second agent/therapy. Those of skill in the art understand that the formulations and/or routes of administration of the various agents/therapies used may vary.

The term "carriers" as used herein may include pharmaceutically acceptable carriers, excipients, or stabilizers that are nontoxic to the cell or mammal being exposed thereto at the dosages and concentrations employed. Often the physiologically acceptable carrier is an aqueous pH buffered solution. Examples of physiologically acceptable carriers include, but not limited to, buffers such as phosphate, citrate, and other organic acids; antioxidants including, but not limited to, ascorbic acid; low molecular weight (less than about 10 residues) polypeptide; proteins, such as, but not limited to, serum albumin, gelatin, or immunoglobulins; hydrophilic polymers such as, but not limited to, polyvinylpyrrolidone (PVP); amino acids such as, but not limited to, glycine, glutamine, asparagine, arginine or lysine; monosaccharides, disaccharides, and other carbohydrates including, but not limited to, glucose, mannose, or dextrins; chelating agents such as, but not limited to, EDTA; sugar alcohols such as, but not limited to, mannitol or sorbitol; salt-forming counterions such as, but not limited to, sodium; and/or nonionic surfactants such as, but not limited to, TWEEN; polyethylene glycol (PEG), and PLURONICS.

The term "treating" or "treatment" of a disease as used herein may refer to executing a protocol, which may include administering one or more drugs to a patient (human or otherwise), in an effort to alleviate signs or symptoms of the disease. Alleviation can occur prior to signs or symptoms of the disease appearing as well as after their appearance. Thus, "treating" or "treatment" includes "preventing" or "prevention" of disease. The terms "prevent" or "preventing" refer to prophylactic and/or preventative measures, wherein the object is to prevent or slow down the targeted pathologic condition or disorder. For example, in the case of infection human cytomegalovirus (HCMV), "preventing" or "preventing" may arise in a situation where a course of treatment is advanced in order to prevent or stall infection by HCMV, such as through vaccination. Such "preventing" or "prevention" also arise in the case of latent infection by HCMV, for example in those individuals who are seropositive but are not exhibiting any symptoms, in which the object would be to prevent active infection and/or clear a patient of said latent infection. In addition, "treating" or "treatment" does not require complete alleviation of signs or symptoms, does not require a cure, and specifically includes protocols that have only a marginal effect on the patient.

The term "patient" as used herein may refer to a biological system to which a treatment can be administered. A biological system can include, for example, an individual cell, a set of cells (e.g., a cell culture), an organ, a tissue, or a multi-cellular organism. A "patient" can refer to a human patient or a non-human patient.

The term "epitope" as used herein may refer to the region of an antigen to which an antibody or T cell binds, e.g. a region of the viral envelope of HCMV, including but not limited to a glycoprotein or a region on a glycoprotein. An "antigen" refers to a substance that elicits an immunological reaction or binds to the products of that reaction.

The terms "purified" or "isolated" antibody, peptide, polypeptide, or protein refers to a peptide, polypeptide, or protein, as used herein, may refer to a peptide, polypeptide, or protein that has been separated from other proteins, lipids, and nucleic acids with which it is naturally associated. The polypeptide/protein can constitute at least 10% (i.e., any percentage between 10% and 100%, e.g., 20%, 30%, 40%, 50%, 60%, 70%, 80%, 85%, 90%, 95%, and 99%) by dry weight of the purified preparation. Purity can be measured by any appropriate standard method, for example, by column chromatography, polyacrylamide gel electrophoresis, or HPLC analysis. An isolated polypeptide/protein (e.g., anti-HCMV antibodies) described in the invention can be produced by recombinant DNA techniques.

B. Structure of Human Cytomegalovirus (HCMV)

Human cytomegalovirus (HCMV) is a prototypical beta-herpesvirus, and is a species of the Cytomegalovirus genus of viruses. HCMV is also known as human herpesvirus-5 (HHV-5). Of the herpesviruses, HCMV harbors the most genes dedicated to evading the host immune response, including adaptive immunity, and represents a significant life-long burden of antigenic T-cell surveillance and immune dysfunction. Accordingly, the viral envelope of HCMV contains various protein complexes that enable wide viral tropism, utilizing multiple glycoprotein complexes to attach and fuse with host cell membranes.

Glycoproteins gB, gH, and gL comprise the core fusion machinery and exist in various protein complexes on the virion surface. Glycoprotein gB catalyzes membrane fusion during viral entry, and gH and gL likely serve as factors which activate gB to permit pH-independent fusion at the cellular membrane. In addition to the gH/gL heterodimer, gH and gL exist in the trimeric gH/gL/gO complex which is essential for viral entry into fibroblasts. The pentameric complex (PC), which consists of gH/gL and three additional proteins UL128, UL130 and UL131a, is required for viral entry into epithelial, endothelial, and myeloid cells where the virion enters through a low pH-dependent endocytosis mechanism. The glycoprotein complex gH/gL/gO (gH trimer) is required for infection of all cell types, while the gH/gL/UL128/130/131a (gH pentamer) complex imparts specificity in infecting epithelial, endothethial, and myeloid cells. Given that the amount of gH/gL/gO trimer on the viral surface correlates with levels of CMV entry in both epithelial and fibroblast cells, gH may contribute to viral entry primarily through activation of the fusion event, rather than serving a receptor-binding role. Without wishing to be bound by theory, anti-gH antibodies may function by interrupting a fusion-triggering signal to gB. Thus, anti-HCMV antibodies which specifically target gH may possess particular therapeutic applicability as shown in Examples 3 through 6 infra.

C. Anti-HCMV Antibodies and Antigen-Binding Portions Thereof

The antibodies or antigen-binding portions thereof of the present disclosure specifically bind to one or more epitopes found on the viral envelope of human cytomegalovirus (HCMV), e.g. to one or more epitopes on a glycoprotein. While the anti-HCMV antibodies or antigen-binding portions thereof of the present disclosure are capable of binding to multiple glycoproteins, e.g. glycoproteins gB and gH, those that bind to one or more epitopes within SEQ ID NO: 1, found on glycoprotein gH are of particular therapeutic utility as they have been shown, e.g. in Examples 3 through 6 infra, to broadly neutralize HCMV infection. Thus, those anti-HCMV antibodies or antigen-binding portions thereof of the present disclosure which specifically bind to one or more epitopes SEQ ID NO: 1 are suitable for use in vaccines and pharmaceutical compositions/methods of use. Furthermore, anti-HCMV antibodies or antigen-binding portions thereof which specifically bind to one or more epitopes within SEQ ID NO: 1 may be combined with other anti-HCMV antibodies, including (but not limited to) other anti-HCMV antibodies of the present disclosure, and/or in combination with antiviral treatments, discussed herein. While anti-HCMV antibodies or antigen-binding portions thereof that specifically bind to one or more epitopes within SEQ ID NO: 1 may have particular therapeutic use, any anti-HCMV antibodies or antigen-binding portions thereof of the present disclosure that specifically bind to HCMV may be of use, e.g. in an immunoassay, to detect the presence of HCMV or an antigenic fragment thereof in a sample, e.g. a biological sample. Such immunoassays are described infra and may or may not be suitable for diagnostic purposes, e.g. sufficient to diagnose an individual as having an active or latent infection of HCMV.

The anti-HCMV antibodies or antigen-binding portions thereof of the present disclosure are capable of binding to a number of different structures on the surface of HCMV, including glycoprotein gH and glycoprotein gB. As discussed herein, while the anti-HCMV antibodies or antigen-binding portions thereof which target the glycoprotein gB may not be capable of broadly neutralizing HCMV, they are capable of specifically binding to HCMV or an antigenic fragment thereof (e.g., glycoprotein gB). Thus, while not necessarily capable of broadly neutralizing HCMV, they may be able to neutralize at least some strains of HCMV, e.g. as shown in Example 3 infra, exemplary anti-gB antibodies of the present disclosure are capable of neutralizing infection by strain AD169. Those anti-gB antibodies of the present disclosure include, but are expressly not limited to, monoclonal antibody and the antigen binding portions thereof of 8H12 as well as recombinant antibodies (e.g. chimeric and/or humanized antibodies) produced from the variable light (SEQ ID NO: 12) and heavy (SEQ ID NO: 11) chains of 8H12 and/or antibodies and antigen-binding portions thereof containing one or more CDRs within the variable light and/or heavy chains of 8H12, including isotype-switched antibodies and artificial constructs, e.g. scFv constructs. In contrast, those anti-HCMV antibodies or antigen-binding portions thereof which bind to glycoprotein gH, especially those that bind to one or more epitopes within SEQ ID NO: 1, may possess particular therapeutic utility as shown in Example 3 infra, as they are capable of broadly neutralizing HCMV. Without wishing to be bound by theory, antibodies that specifically bind to glycoprotein gH may be capable of broadly neutralizing HCMV because of the role glycoprotein gH plays in viral entry. Glycoprotein gH is part of a heterodimer, as well as a trimeric complex and a pentameric complex, and is required for viral entry, serving as a factor to permit cell surface fusion. Thus, while not wishing to be bound by theory, these anti-HCMV antibodies or antigen-binding portions thereof which target glycoprotein gH are capable of broadly inhibiting HCMV infection because they blocking and/or disrupting viral entry pathways. These anti-HCMV antibodies or antigen-binding portions thereof which target gH include, but are expressly not limited to, monoclonal antibodies and the antigen-binding portions thereof of 10C10 and 5C3, as well as recombinant antibodies (e.g. chimeric and/or humanized antibodies) produced from the variable light (SEQ ID NO: 10 for 5C3 and SEQ ID NO: 14 for 10C10) and heavy (SEQ ID NO: 9 for 5C3 and SEQ ID NO: 13 for 10C10) and/or antibodies and antigen-binding portions thereof containing one or more CDRs within the variable light and/or heavy chains of either 10C10 and 5C3, including but not limited to antibodies generated with CDRs from one or both of 5C3 and 10C10, e.g. isotype-switched antibodies or scFv constructs. 10C10 and 5C3 were generated by injecting mice with the lab strain HCMV AD169 which lacks the pentamer complex due to deletion of UL131a and subsequently generating hybridoma clones, as described in Example 1 infra. This was chosen so as to generate antibodies that specifically bind to glycoprotein gB or gH without targeting the additional proteins in the pentameric complex. 10C10 and 5C3 specifically bind to one or more epitopes within the core binding region (SEQ ID NO: 1), which is found within glycoprotein gH. The full length of glycoprotein gH, generated by consensus sequence, is reproduced below:

```
                                           (SEQ ID NO: 2)
MRPGLPFYLTVFAVYLLSHLPSQRYGADAASEALDPHAFHLLLN

TYGRPIRFLRENTTQCTYNSSLRNSTVVRENAISFNFFQSYNQY

YVFHMPRCLFAGPLAEQFLNQVDLTETLERYQQRLNTYALVSKD

LASYRSFSQQLKAQDSLGQQPTTVPPPIDLSIPHVWMPPQTTPH

DWKGSHTTSGLHRPHFNQTCILFDGHDLLFSTVTPCLHQGFYLM

DELRYVKITLTEDFFVVTVSIDDDTPMLLIFGHLPRVLFKAPYQ
```

-continued
```
RDNFILRQTEKHELLVLVKKTQLNRHSYLKDSDFLDAALDFNYL

DLSALLRNSFHRYAVDVLKSGRCQMLDRRTVEMAFAYALALFAA

ARQEEAGTEISIPRALDRQAALLQIQEFMITCLSQTPPRTTLLL

YPTAVDLAKRALWTPDQITDITSLVRLVYILSKQNQQHLIPQWA

LRQIADFALQLHKTHLASFLSAFARQELYLMGSLVHSMLVHTTE

RREIFIVETGLCSLAELSHFTQLLAHPHHEYLSDLYTPCSSSGR

RDHSLERLTRLFPDATVPATVPAALSILSTMQPSTLETFPDLFC

LPLGESFSALTVSEHVSYVVTNQYLIKGISYPVSTTVVGQSLII

TQTDSQSKCELTRNMHTTHSITAALNISLENCAFCQSALLEYDD

TQGVINIMYMHDSDDVLFALDPYNEVVVSSPRTHYLMLLKNGTV

LEVTDVVVDATDSRLLMMSVYALSAIIGIYLLYRMLKTC.
```

The core binding region recognized by 10C10 and 5C3 (SEQ ID NO: 1) is underlined within SEQ ID NO: 2 above, and is heavily conserved across HCMV strains; analysis of 10 geographically distinct HCMV strains demonstrated identical sequence homology of SEQ ID NO: 1. This is in direct contrast to virion surface glycoproteins, e.g. gO and UL128, which can range considerably in homology. The conservation in SEQ ID NO: 1 across HCMV strains is specifically relevant to the underlying ability of several of the anti-HCMV antibodies or antigen-binding portions thereof of the present disclosure, including but not limited to 10C10 and 5C3, to broadly neutralize HCMV infection. This is because SEQ ID NO: 1 is highly conserved across HCMV species. Thus, antibodies or antigen-binding portions thereof which specifically bind to one or more epitopes within SEQ ID NO: 1 (found on glycoprotein gH) will be able to bind to a broad range of HCMV strains, and because glycoprotein gH is involved in viral entry, antibodies which target gH may prevent viral entry, thus, neutralizing HCMV infection.

While both 10C10 and 5C3 appear to specifically bind to one or more epitopes within SEQ ID NO: 1, the specific epitopes which 10C10 and 5C3 bind to within SEQ ID NO: 1 are distinct, but proximal; see Example 9 infra. Furthermore, while not wishing to be bound by theory, the epitopes for either of 10C10 and 5C3 may be conformational epitopes (e.g. a discontinuous epitope within SEQ ID NO: 1) as suggested by cyclic peptide arrays, and further by how binding of 5C3 to gH was enhanced by co-expression of gL (as part of a heterodimer). The nucleotide sequences for the variable regions (heavy and light) of 10C10 and 5C3 (anti-gH) and 8H12 (anti-gB) is reproduced below in Table 1; corresponding amino acid sequences are reproduced below in Table 2. Example 11 infra discusses the genomic analysis of the anti-HCMV antibodies.

TABLE 1

Nucleotide sequences of select anti-HCMV antibodies

| Antibody | Gene | Nucleotide Sequence |
|---|---|---|
| 5C3 | Heavy chain | CAGGTCCAACTGCAGCAGCCTGGGGCTGA GCTGGTGAGGCCTGGGGCTTCAGTGAAGC TGTCCTGCAAGGCTTCTGGCTACACCTTC ACCACTTACTGGATGAACTGGGTGAAGCA GAGGCCTGGACAAGGCCTTGAATGGATTG GTATGATTGATCCTTCAGACAGTGAAACT |

TABLE 1-continued

Nucleotide sequences of select anti-HCMV antibodies

| Antibody | Gene | Nucleotide Sequence |
|---|---|---|
| | | CACTACAATCAAATGTTCAAGGACAAGGC CACATTGACTGTGGACACATCCTCCAGCA CAGCCTACATGCAACTCAGCAGTCTGACA TCTGAGGATTCTGCGGTCTATTACTGTGC AAGAGGCCGGTCCTGGTTTGTTTATTGGG GCCAAGGGACTCTGGTCACTGTCTCTAGC (SEQ ID NO: 3) |
| | Light chain (kappa) | GACATTGTGCTGACACAGTCTCCTGCTTC CTTAGCTGTTTCTCTGGGGCAGAGGGCCA CCATCTCATGCAGGGCCAGCAAAAGTGTC AGTTCATCTGGCTATAGTTATGTGCACTG GTACCAGCAGAAACCAGGGCAACCACCCA AACTCCTCATCTATCTTGCATCCAACCTA GAATCTGGGGTCCCTGCCAGGTTCAGTGG CAGTGGGTCTGGGACAGACTTCACCCTCA ACATCCATTCTGTGGAGGAGGAGGATGCT GCAACCTATTACTGTCAGCACAATAGGGA GCTTCCGTACACTTTCGGAGGGGGGACCA AGCTGGAAATAAAACGG (SEQ ID NO: 4) |
| 8H12 | Heavy chain | GATGTGCAGCTTCAGGAGTCGGGACCTGG CCTGGTGAAACCTTCTCAGTCTCTGTCCC TCACCTGCACTGTCACTGGCTACTCAATC ACCAGTGATTATGCCTGGAACTGGATCCG GCAGTTTCCAGGAAACAAACTGGAGTGGA TGGGCTACATAAGCTACAGTGGTAGCACT AGCTACAACCCATCTCTCAAAAGTCGAAT CTCTATCACTCGAGACACATCCAAGAACC AGTTCTTCCTGCAGTTGAATTCTGTGACT ACTGAGGACACAGCCACATATTACTGTGC AAGACGGAGGGATTACGGAGAGGACTACT TTGACTACTGGGGCCAAGGCACCACTCTC ACAGTCTCCAGC (SEQ ID NO: 5) |
| | Light chain (kappa) | GACATTGTGATGACACAGTCTCCATCCTC CCTGAGTGTGTCAGCAGGAGAGAAGGTCA CTATGAGCTGCAAGTCCAGTCAGAGTCTG TTAAACAGTGGAAATCAAAGGAACTACTT GGCCTGGTACCAGCAGAAACCAGGGCAGC CTCCTAAACTGTTAATCTACGGGGCATCC ACTAGGGAATCTGGGGTCCCTGATCGCTT CACAGGCAGTGGATCTGGAACCGATTTCA CTCTTACCATCAGCAGTGTGCAGGCTGAA GACCTGGCAGTTTATTATTGTCAGAATGA TTATAGTTATCCATTCACGTTCGGCTCGG GGACAAAGTTGGAAATAAAACGG (SEQ ID NO: 6) |
| 10C10 | Heavy chain | GAGGTCCAGCTTCAGCAGTCAGGACCTGA GCTGGTGAAGCCTGGAGTTTCAATGAGGA TATCCTGCAAGGCTTCTGGTTTCTCATTC ACTGACTACACCATGAACTGGGTGAAACA GAGCCATAGAAAGAACCTTGAGTGGATTG GACTTGTTAATCCTTACAATGGTGGTACT AGCCACAACCCGAACTTCAAGGGCAAGGC CACATTAACTGTAGACAAGTCATCCAGCA CAGCCTACATGGAACTCCTCAGTCTGACA TCTGAGGACTCTGCAGTCTATTACTGTGC AAGAAGGGGCGACGCGACTATGCTTTGG ACTACTGGGGTCAGGGAACCTCAGTCACC GTCTCCAGC (SEQ ID NO: 7) |
| | Light chain (kappa) | GATATTGTGCTAACTCAGTCTCCAGTCAC CCTGTCTGTGACTCCAGGAGATAGCGTCA GTCTTTCCTGCAGGGCCAGCCAAAGTGTT AGTAACAACTACACTGGTATCAACAAAA ATCACATGAGTCTCCAAGGCTTCTCATAA AGTATGCTTCCCAGTCCATCTCTGGGATC CCCTCCAGGTTCAGAGGCAGTGGATCAGG GACAGATTTCACTCTCAGTATCATCAGTG TGGAGACTGAAGATTTTGGAATGTATTTC TGTCAACAGAGTAACATCTGGCCTCACAC GTTCGGTGCTGGGACCAAGCTGGAGCTGA AACGG (SEQ ID NO: 8) |

TABLE 2

Variable heavy/light (kappa) sequences of select anti-HCMV antibodies. CDRs are underlined.

| Antibody | Chain | Peptide Sequence |
|---|---|---|
| 5C3 | Heavy chain | QVQLQQPGAELVRPGASVKLSCKAS<u>GYTF TTYWMN</u>WVKQRPGQGLEWIGM<u>IDPSDSET</u> HYNQMFKDKATLTVDTSSSTAYMQLSSLT SEDSAVYYC<u>ARGRSWFVY</u>WGQGTLVTVSS (SEQ ID NO: 9) |
| | Light chain (kappa) | DIVLTQSPASLAVSLGQRATISCRAS<u>KSV SSSGYSY</u>VHWYQQKPGQPPKLLIY<u>LASNL</u> ESGVPARFSGSGSGTDFTLNIHSVEEEDA ATYYC<u>QHNRELPYT</u>FGGGTKLEIKR (SEQ ID NO: 10) |
| 8H12 | Heavy chain | DVQLQESGPGLVKPSQSLSLTCTVT<u>GYSI TSDYA</u>WNWIRQFPGNKLEWMGY<u>ISYSGST</u> SYNPSLKSRISITRDTSKNQFFLQLNSVT TEDTATYYC<u>ARRRDYGEDYFDY</u>WGQGTTL TVSS (SEQ ID NO: 11) |
| | Light chain (kappa) | DIVMTQSPSSLSVSAGEKVTMSCKSS<u>QSL LNSGNQRNY</u>LAWYQQKPGQPPKLLIY<u>GAS</u> TRESGVPDRFTGSGSGTDFTLTISSVQAE DLAVYYC<u>QNDYSYPFT</u>FGSGTKLEIKR (SEQ ID NO: 12) |
| 10C10 | Heavy chain | EVQLQQSGPELVKPGVSMRISCKAS<u>GFSF TDYTMN</u>WVKQSHRKNLEWIGL<u>VNPYNGGT</u> SHNPNFKGKATLTVDKSSSTAYMELLSLT SEDSAVYYC<u>ARRGRRDYALDY</u>WGQGTSVT VSS (SEQ ID NO: 13) |
| | Light chain (kappa) | DIVLTQSPVTLSVTPGDSVSLSCRAS<u>QSV SNNLH</u>WYQQKSHESPRLLIK<u>YASQ</u>SISGI PSRFRGSGSGTDFTLSIISVETEDFGMYF C<u>QQSNIWPHT</u>FGAGTKLELKR (SEQ ID NO: 14) |

TABLE 3

Complementarity Determining Regions (CDRs) of select anti-HCMV antibodies

| Antibody | Chain | CDR1 | CDR2 | CDR3 |
|---|---|---|---|---|
| 5C3 | Heavy chain | GYTFTTYW (SEQ ID NO: 15) | IDPSDSET (SEQ ID NO: 16) | ARGRS WFVY (SEQ ID NO: 17) |
| | Light chain (kappa) | KSVSSSGYSY (SEQ ID NO: 18) | LAS (SEQ ID NO: 19) | QHNRE LPYT (SEQ ID NO: 20) |
| 8H12 | Heavy chain | GYSITSDYA (SEQ ID NO: 21) | ISYSGST (SEQ ID NO: 22) | ARRRDY GEDYFDY (SEQ ID NO: 23) |
| | Light chain (kappa) | QSLLNSGN QRNY (SEQ ID NO: 24) | GAS (SEQ ID NO: 25) | QNDYS YPFT (SEQ ID NO: 26) |
| 10C10 | Heavy chain | GFSFTDYT (SEQ ID NO: 27) | VNPYNGGT (SEQ ID NO: 28) | ARRGRRD YALDY (SEQ ID NO: 29) |
| | Light chain (kappa) | QSVSNN (SEQ ID NO: 30) | YAS (SEQ ID NO: 31) | QQSNIW PHT (SEQ ID NO: 32) |

One of ordinary skill in the art will appreciate that the complementarity determining regions ("CDRs") of most antibodies, e.g., 10C10, 5C3, and 8H12 largely determine the biological activity of the antibodies by forming the paratope on the antibody. For example, 10C10 and 5C3 recognize one or more epitopes within SEQ ID NO: 1, whereas 8H12 recognizes an epitope on HCMV glycoprotein gB, and this activity is determined largely by the sequences contained in the variable light and heavy chains, particularly the CDRs. Accordingly, some embodiments of the present disclosure are directed to antibodies expressing the CDRs listed in Table 3.

For example, some embodiments of the present disclosure are directed to antibodies or antigen-binding portions thereof having one or more CDRs within the heavy chain comprising one or more of SEQ ID NO: 15, SEQ ID NO: 16, and/or SEQ ID NO: 17, or a certain degree of homology with one or more of SEQ ID NO: 15, SEQ ID NO: 16 and/or SEQ ID NO: 17, e.g. at least 75%, at least 80%, at least 85%, at least 90%, at least 95%, or more than 95%. One or more of SEQ ID NO: 15, SEQ ID NO: 16, and/or SEQ ID NO: 17 may have conservative substitutions. Some embodiments of the present disclosure are directed to antibodies or antigen-binding portions thereof having one or more CDRs within the heavy chain comprising one or more of SEQ ID NO: 21, SEQ ID NO: 22, and/or SEQ ID NO: 23, or a certain degree of homology with one or more of SEQ ID NO: 21, SEQ ID NO: 22 and/or SEQ ID NO: 23, e.g. at least 75%, at least 80%, at least 85%, at least 90%, at least 95%, or more than 95%. One or more of SEQ ID NO: 21, SEQ ID NO: 22, and/or SEQ ID NO: 23 may have conservative substitutions. Some embodiments of the present disclosure are directed to antibodies or antigen-binding portions thereof having one or more CDRs within the heavy chain comprising one or more of SEQ ID NO: 27, SEQ ID NO: 28, and/or SEQ ID NO: 29, or a certain degree of homology with one or more of SEQ ID NO: 27, SEQ ID NO: 28 and/or SEQ ID NO: 29, e.g. at least 75%, at least 80%, at least 85%, at least 90%, at least 95%, or more than 95%. One or more of SEQ ID NO: 27, SEQ ID NO: 28, and/or SEQ ID NO: 29 may have conservative substitutions. Some embodiments of the present disclosure are directed to antibodies or antigen-binding portions thereof having one or more CDRs within the light chain comprising one or more of SEQ ID NO: 18, SEQ ID NO: 19, and/or SEQ ID NO: 20, or a certain degree of homology with one or more of SEQ ID NO: 18, SEQ ID NO: 19 and/or SEQ ID NO: 20, e.g. at least 75%, at least 80%, at least 85%, at least 90%, at least 95%, or more than 95%. One or more of SEQ ID NO: 18, SEQ ID NO: 19, and/or SEQ ID NO: 20 may have conservative substitutions. Some embodiments of the present disclosure are directed to antibodies or antigen-binding portions thereof having one or more CDRs within the light chain comprising one or more of SEQ ID NO: 24, SEQ ID NO: 25, and/or SEQ ID NO: 26, or a certain degree of homology with one or more of SEQ ID NO: 24, SEQ ID NO: 25 and/or SEQ ID NO: 26, e.g. at least 75%, at least 80%, at least 85%, at least 90%, at least 95%, or more than 95%. One or more of SEQ ID NO: 24, SEQ ID NO: 25, and/or SEQ ID NO: 26 may have conservative substitutions. Some embodiments of the present disclosure are directed to antibodies or antigen-binding portions thereof having one or more CDRs within the light chain comprising one or more of SEQ ID NO: 30, SEQ ID NO: 31, and/or SEQ ID NO: 32, or a certain degree of homology with one or more of SEQ ID NO: 30, SEQ ID NO: 31 and/or SEQ ID NO: 32, e.g. at least 75%, at least 80%, at least 85%, at least 90%, at least 95%, or more than 95%. One or more of SEQ ID NO: 30, SEQ ID NO: 31, and/or SEQ ID NO: 32 may have conservative substitutions.

In some embodiments, the anti-HCMV antibodies or antigen-binding portions thereof are humanized antibodies, e.g. a murine humanized antibody. Techniques for humanization of murine antibodies are known to one of ordinary skill in the art and are generally reviewed in Safdari et al., (2013) Biotechnol. Genet. Eng. Rev., 29: 175-86, hereby incorporated by reference in its entirety. Humanization of antibodies generally comprises grafting of CDRs (for example, but not necessarily, one or more of SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, and/or SEQ ID NO: 32, or conservative substituted variants thereof) into an appropriate human variable region framework, for example, as disclosed in Jones et al. (1986) Nature 321, 522-525, hereby incorporated by reference in its entirety. Common methods used include, but are not limited to, framework-homology-based humanization, germline humanization, complementary determining regions (CDR)-homology-based humanization and specificity determining residues (SDR) grafting. Proper orientation of the CDRs in the humanized antibody is typically necessary and can be determined by, for example, evaluating the crystal structure of the humanized antibody. The principal advantage of humanized antibodies comes from significantly reduced immunogenicity when compared to a murine monoclonal antibody, particularly the constant domain (Fc region) of a murine antibody, although humanizing the variable domains also leads to reduced immunogenicity.

Some embodiments of the invention are directed to vectors and vector systems containing nucleotide sequences that code for the variable regions of anti-HCMV antibodies, e.g. 10C10, 5C3, and 8H12, as well as cells transformed with such vectors and/or vector systems. The vector may be, for example but not necessarily, a plasmid; other explicitly non-limiting recombinant vectors are known in the art and may include, e.g. phage vectors such as a λ phage vector, other viral vectors such as non-replicating adenoviral vector, lentiviral vector, pSV, pCMV series of plasmid vectors, vaccinia and retroviral vectors, baculoviral vectors, cosmids, artificial chromosomes. The vector may be a mammalian expression vectors; for example, vectors may be transfected into mammalian cells and the DNA may be integrated into the genome by homologous recombination in the case of stable transfection, or alternatively the cells may be transiently transfected. Common to most engineered vectors are origin of replications, multicloning sites, and selectable markers, so as long as a vector (including systems of vectors, e.g. multiple plasmids) contain such a system they are considered to be covered by the scope of this invention. Common promoters for mammalian expression vectors include CMV and SV40 promoters; nonviral promoters such as EF-1 promoters are also known. In some embodiments, the present disclosure is directed to a vector or system of vectors containing one or more nucleic acid sequences encoding one or more CDRs of one or more heavy and/or light chains of one or more of the anti-HCMV antibodies of the present disclosure, e.g. nucleotide sequence or sequences coding for one or more of SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, and/or SEQ ID NO: 32. These nucleotides coding for CDRs may have conservative substitutions and, independent of such conservative substitutions, may share a certain degree of homology (i.e. at least 75%, at least 80%, at least 85%, at least 90%, at least 95%, or more than 95%) with the nucleotide sequences coding for the CDRs within any one of SEQ ID NO: 3, SEQ ID NO: 4, SEQ ID NO: 5, SEQ ID NO: 6, SEQ ID NO: 7, and/or SEQ ID NO: 8.

The nucleic acid sequences may have conservative substitutions, and may be codon optimized. As used herein, codon optimization refers to an in vitro mutagenesis of a nucleic acid to increase or maximize expression of a gene (e.g. a transgene relative to the unmodified nucleic acid, without changing (or with minimal change) to the amino acid sequence of the synthesized protein, i.e. synonymous mutations. Codon optimization can affect protein expression rates up to 1,000× fold, particularly by favoring efficient soluble protein expression. The codons changed are typically ones not generally used by the host cell translation system. Codon bias/codon usage frequency depends on the host organism, and is described, for example, in U.S. Pat. No. 8,326,547, hereby incorporated by reference in its entirety.

A vector or vector system that codes for one or both variable region(s) of 10C10 may contain one of or both of SEQ ID NO: 7 and SEQ ID NO: 8 or a nucleotide sequence or sequences that shares or share a degree of homology with SEQ ID NO: 7 and/or SEQ ID NO: 8, e.g. at least 75% homology, at least 80% homology, at least 85% homology, at least 90% homology, at least 95%, or more than 95% homology with either or both of SEQ ID NO: 7 and SEQ ID NO: 8. Independent of such homology, SEQ ID NO: 7 and/or SEQ ID NO: 8 may have conservative substitutions and such would be considered to be within the scope of this invention. The nucleotide sequences coding for the variable regions may or may not be on the same vector; for example, SEQ ID NO: 7 may be on a first vector (e.g. a first plasmid) and SEQ ID NO: 8 may be on a second vector (e.g. a second plasmid). Such a system may allow for greater control of expression, for example, by allowing for the expression of the variable light and/or heavy chain to be separately inducible.

A vector or vector system that codes for one or both variable region(s) of 5C3 may contain one of or both of SEQ ID NO: 3 and SEQ ID NO: 4 or a nucleotide sequence or sequences that shares or share a degree of homology with SEQ ID NO: 3 and/or SEQ ID NO: 4, e.g. at least 75% homology up to, at least 80% homology, at least 85% homology at least 90% homology, at least 95%, or more than 95% homology either or both of SEQ ID NO: 3 and SEQ ID NO: 4. Independent of such homology, SEQ ID NO: 3 and/or SEQ ID NO: 4 may have conservative substitutions and such would be considered to be within the scope of this invention. As discussed herein, the nucleotide sequences coding for the variable regions may or may not be on the same vector and expression of such may or may not be separately inducible.

A vector or vector system that codes for one or both variable region(s) of 8H12 may contain one of or both of SEQ ID NO: 5 and SEQ ID NO: 6 or a nucleotide sequence or sequences that shares or share a degree of homology with SEQ ID NO: 5 and/or SEQ ID NO: 6, e.g. at least 75% homology up to, at least 80% homology, at least 85% homology at least 90% homology, at least 95%, or more than 95% homology either or both of SEQ ID NO: 5 and SEQ ID NO: 6. Independent of such homology, SEQ ID NO: 5 and/or SEQ ID NO: 6 may have conservative substitutions and such would be considered to be within the scope of this invention. As discussed herein, the nucleotide sequences coding for the variable regions may or may not be on the same vector and expression of such may or may not be separately inducible.

Some embodiments of the present disclosure are directed to methods of making a recombinant anti-HCMV antibody, e.g. a chimeric anti-HCMV antibody or a humanized anti-HCMV antibody. In the case of a chimeric antibody, a host cell (e.g. a yeast cell or an E. coli cell) is transfected (e.g. by a phage) by a vector, including those discussed supra, containing genes coding for the variable heavy/light regions of one or more anti-HCMV antibodies, e.g. SEQ ID NO: 3 and/or SEQ ID NO:4 in the case of 5C3, SEQ ID NO: 7 and SEQ ID NO: 8 in the case of 10C10, SEQ ID NO: 5 and SEQ ID NO: 6 in the case of 8H12, or, in the case of humanized antibodies, they may be transfected by a vector that contains nucleotides coding for CDRs of the variable heavy/light regions of the anti-HCMV antibodies, e.g. nucleotide sequence or sequences coding for one or more of SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, and/or SEQ ID NO: 32. These nucleotides coding for CDRs may have conservative substitutions and, independent of such conservative substitutions, may share a certain degree of homology (i.e. at least 75%, at least 80%, at least 85%, at least 90%, at least 95%, or more than 95%) with the nucleotide sequences coding for one or more of SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, and/or SEQ ID NO: 32. With either chimeric or humanized antibodies, the Fc region will remain human. The transformed host cell will then be induced to produce the recombinant antibodies, which may assemble the antibodies from heavy/light chains in the host cell and then transport the antibodies out of the cell, or the antibodies may self-assemble outside the host cell and be exported as heavy/light chains. Common host cells may include yeast cells, e.g. *S. cerevisiae, S. pombe* and *P. pastoris*, bacteria, e.g. *E. coli*, and mammalian cells, e.g. Chinese hamster ovary (CHO) cells, including DUXB11, DG44 and CHOK1 lineages, NS0 murine myeloma cells, PER.C6 human cells, and human embryonic kidney (HEK) cells, e.g. HEK293. Other less common host cells, but still included within the scope of the invention, include plant cells, for example, those based on the Ti plasmid of *Agrobacterium tumefaciens*. Cell-free expression systems also exist, for example, based on *E. coli* cell lysate, containing cellular components necessary for transcription/translation. Eukaryotic and mammalian cell-free systems are also known in the art, for example wheat germ cell-free expression system, and those described in Brodel et al. (2015), *Methods Mol Bio*. 1261: 129-40, hereby incorporated by reference in its entirety. Some recombinant antibody production systems express the recombinant antibodies on the surface of the host cell before harvesting, others simply release the antibodies into a medium for collection. Such variations are intended to be within the scope of the present disclosure.

D. Kits and Methods of Use

One embodiment of the present disclosure is directed to kits for detecting HCMV present in a sample. These kits may comprise an anti-HCMV antibody or antigen-binding portion thereof of the present disclosure and various reagents, for example, reagents that aid in detection of binding between the anti-HCMV antibody and an epitope present on HCMV or an antigenic fragment thereof. In some embodiments, the anti-HCMV antibodies or antigen-binding portion thereof specifically bind to one or more epitopes within SEQ ID NO: 1.

The kits may be in vitro assays, such as immunoassays, e.g. enzyme immune assays (EIA), enzyme linked immunosorbent assay (ELISA), ELISPOT (enzyme-linked immunospot), radioimmunoassays (RIAs), immunofluorescence, and other assays known in the art, including but not limited to Western Blot analysis and/or immunoprecipitation methods. The in vitro assays may be competitive, or indirect, such as in a sandwich assay, or may be an antibody capture method. For example in a direct ELISA, a buffered solution of an antigen, e.g. a sample containing HCMV or an antigenic fragment thereof (e.g. a biological sample containing or suspected of containing HCMV), including but not limited to SEQ ID NO: 1, is added to a well of a microtiter plate, e.g. a 96-well plate. A solution of non-reacting protein, e.g. bovine serum albumin or casein is then added to the well. The anti-HCMV antibody or antigen-binding portions thereof conjugated to a reporter molecule enzyme is added, e.g. conjugated to horseradish peroxidase, although that is not necessarily the enzyme, as other common enzymes include alkaline phosphatase, or β-D-galactosidase, although other enzymes are conceivable and considered embodied by the present disclosure. A substrate for the enzyme is then added, which leads to a detectable signal. For example, adding TMB to horseradish peroxidase leads to a colored product, in which case the ELISA is a colorimetric assay. ELISAs may be run in a qualitative or quantitative format. Qualitative results provide a simple positive or negative result (yes or no) for a sample. The cutoff between positive and negative is determined by the analyst and may be statistical. Sandwich ELISAs generally follow the following protocol. Capture anti-HCMV antibody or antigen-binding portions thereof is bound to (i.e. "immobilized") on a substrate, e.g. a microtiter plate. Antigen-containing sample (i.e. sample containing HCMV or an antigenic fragment thereof, including but not limited to SEQ ID NO: 1, is then added to the substrate at which point it is captured by the anti-HCMV antibodies. The substrate is then washed to remove unbound antigen. A second anti-HCMV antibody or antigen-binding portions thereof is added, which binds to a different epitope on HCMV, including but not limited SEQ ID NO: 1. The second anti-HCMV antibody or antigen-binding portions thereof is bound to a reporter molecule, e.g. an enzyme, although the reporter molecule may be any molecule which leads to a detectable signal. The plate may be washed a second time, and in those instances where the reporter molecule is an enzyme, a substrate may be added, e.g. TMB, that results in a detectable signal (also a colorimetric assay). A third type of common ELISA is competitive ELISA. In these embodiments, unlabeled anti-HCMV antibody or antigen-binding portions thereof is incubated in the presence of an antigen-containing sample (i.e. sample containing HCMV or an antigenic fragment thereof, including but not limited to SEQ ID NO: 1), which are then added to an antigen-coated well. The plate is washed so as to remove unbound antibodies. A secondary antibody that is specific to the primary antibody, e.g. a secondary antibody specific to anti-HCMV antibodies. The secondary antibody is bound to a reporter molecule, as described herein, such as an enzyme (or any other molecule that may lead to a detectable signal). Some competitive ELISA utilize labeled antigens rather than labeled antibodies; the less antigen in the sample, the more labeled antigen is retained and the stronger a detectable signal results.

Other forms of common in vitro assays include radioimmunoassays (RIAs). Typically a known quantity of an antigen is linked to a radioactive tracer, e.g. I-125 although others are suitable for use, which is then mixed with a known amount of antibody specific for the antigen, e.g. anti-HCMV antibodies or antigen-binding portions thereof. Then, a sample containing unknown quantity of an antigen is added, (e.g. a biological sample that contains or is suspected of containing HCMV or an antigenic fragment thereof) is added. This is a direct competitive for specific binding; as the concentration of unlabeled antigen is increased, the binding between the anti-HCMV antibodies and the labeled standard is decreased, which is directly measurable by measuring radioactivity. Other assays are known and a person of ordinary skill in the art would readily recognize their applicability.

In some embodiments, the invention is directed to a method of detecting HCMV or an antigenic fragment thereof in a sample, including but not limited to SEQ ID NO:1. Such methods may utilize any of the assays described herein, or others that are known in the art. Several of the assays described herein are capable of quantifying the amount of antigen present in a sample, and so accordingly, in some embodiments, the present disclosure is directed to methods of quantifying the amount of HCMV or antigenic fragments thereof present in a sample, e.g. a biological sample.

The assays containing anti-HCMV antibodies or antigen-binding portions thereof of the present disclosure may or may not be utilized for diagnostic purposes. Accordingly, in some embodiments, the invention is directed to methods of diagnostic use of the anti-HCMV antibodies or antigen-binding portions thereof of the present disclosure. Because of the specificity of the anti-HCMV antibodies or antigen-binding portions thereof of the present disclosure, immunoassays containing anti-HCMV antibodies or antigen-binding portions thereof of the present disclosure may be sufficient to diagnose an individual as having an active or latent infection of HCMV. The antibodies or antigen-binding portions thereof need not be restricted to any particular epitopes, so long as the antibodies or antigen-binding portions thereof used are specific to HCMV. For example, in a sandwich assay, the first anti-HCMV antibody or antigen-binding portions thereof may bind to a first epitope, such as a gH or gB glycoprotein, and the second anti-HCMV antibody or antigen-binding portions thereof (which is bound to a reporter molecule) may bind to a second epitope; for example, but not necessarily, if the first anti-HCMV antibody or antigen-binding portions thereof specifically binds to the glycoprotein gH, the second may bind to glycoprotein gB, and the reverse is true as well. For example, the anti-HCMV antibody 8H12 specifically binds to glycoprotein gB, and the anti-HCMV antibodies 5C3 and 10C10 specifically bind to one or more epitopes within SEQ ID NO: 1, which is located within glycoprotein gH. Accordingly, kits and methods used to detect or quantify the amount of HCMV or an antigenic fragment thereof may contain 8H12 and one of 5C3 and 10C10 and would be considered within the scope of this invention. Or, any of 8H12, 5C3, 10C10, including antigen-binding portions thereof, and any other anti-HCMV antibody, so long as they are suitable for incorporation into such kits/methods. In some embodiments, the first antibody or antigen-binding portions thereof and second antibody or antigen-binding portions thereof may bind to the same antigen/glycoprotein, e.g. both may bind to glycoprotein gH, gB, or in some embodiments may bind to completely different antigens on surface of HCMV viral envelope. For example, but not necessarily limited to, as described in Example 10 supra, human-derived monoclonal antibody MSL-109 specifically binds to an epitope containing amino acid no. 168 of glycoprotein gH, while the monoclonal antibodies 10C10 and 5C3 specifically bind to the one or more epitopes within SEQ ID NO: 1. Because of the distance between binding sites, these antibodies or antigen-binding portions thereof may be suitable for use in those immunoassays, e.g. sandwich assays, in which multiple binding sites on the same target (e.g. HCMV or an antigenic fragment thereof) are necessary. Or, in some embodiments, one may target a totally different antigen, e.g. the first anti-HCMV antibody or antigen-binding portions thereof targets an epitope on glycoprotein gH (e.g. MSL-109, 10C10, and/or 5C3) and the second anti-HCMV antibody targets an epitope elsewhere, for example but not necessarily glycoprotein gB, gH, gL, gO, UL128, UL130, and/or UL131a and the antigenic fragments thereof of the corresponding antigens. One will appreciate that the anti-HCMV antibodies or antigen-binding portions thereof used for purposes of detecting and/or quantifying HCMV present in a sample or even for diagnostic purposes do not necessarily need to be capable of broadly neutralizing HCMV to possess utility for such purposes, accordingly anti-HCMV antibodies such as, for example, 8H12 are suitable for use in such diagnostic methods.

E. Therapeutic Compositions, Methods, and Vaccines

One embodiment of the present disclosure is directed towards pharmaceutical compositions comprising at least one anti-HCMV antibody or antigen-binding portion thereof of the present disclosure, as well as their methods of use in treating a patient in need thereof. The patient may have a latent or active infection by a virulent strain of HCMV. The anti-HCMV antibodies or antigen-binding portions thereof utilized in these compositions and methods may be any anti-HCMV antibody or antigen-binding portion thereof of the present disclosure, but of particular utility are those anti-HCMV antibodies or antigen-binding portions thereof that specifically bind to one or more epitopes within SEQ ID NO: 1 found on the glycoprotein gH, e.g. 10C10 and 5C3.

A pharmaceutically acceptable anti-HCMV antibody or antigen-binding portions thereof composition suitable for patient administration will contain an effective amount of the anti-HCMV antibody or antibodies or antigen-binding portions thereof in a formulation which both retains biological activity while also promoting maximal stability during storage within an acceptable temperature range. The pharmaceutical compositions can also include, depending on the formulation desired, pharmaceutically acceptable diluents, pharmaceutically acceptable carriers and/or pharmaceutically acceptable excipients, or any such vehicle commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. The amount of an excipient that is useful in the pharmaceutical composition or formulation of this invention is an amount that serves to uniformly distribute the antibody throughout the composition so that it can be uniformly dispersed when it is to be delivered to a subject in need thereof. It may serve to dilute the antibody to a concentration which provides the desired beneficial palliative or curative results while at the same time minimizing any adverse side effects that might occur from too high a concentration. It may also have a preservative effect. Thus, for antibodies having a high physiological activity, more of the excipient will be employed. On the other hand, for any active ingredient(s) that exhibit a lower physiological activity, a lesser quantity of the excipient will be employed.

The pharmaceutically acceptable composition may be in liquid form or solid form. A solid formulation is generally, but not necessarily, lyophilized and brought into solution prior to administration for either single or multiple dosing. The formulations should not be exposed to extreme temperature or pH so as to avoid thermal denaturation. Thus, it is essential to formulate an antibody composition of the present disclosure within a biologically relevant pH range. A solution buffered to maintain a proper pH range during storage is often necessary, especially for liquid formulations stored for longer periods of time between formulation and administration. Typically, both liquid and solid formulations require storage at lower temperatures (usually 2-8° C.) in order to retain stability for longer periods. Formulated antibody compositions, especially liquid formulations, may contain a bacteriostat to prevent or minimize proteolysis during storage, including but not limited to effective concentrations (usually <1% w/v) of benzyl alcohol, phenol, m-cresol, chlorobutanol, methylparaben, and/or propylparaben. A bacteriostat may be contraindicated for some patients. Therefore, a lyophilized formulation may be reconstituted in a solution either containing or not containing such a component. Additional components may be added to either a buffered liquid or solid antibody formulation, including but not limited to sugars as a cryoprotectant (including but not necessarily limited to polyhydroxy hydrocarbons such as sorbitol, mannitol, glycerol and dulcitol and/or disaccharides such as sucrose, lactose, maltose or trehalose) and, in some instances, a relevant salt (including but not limited to NaCl, KCl or LiCl). Such antibody formulations, especially liquid formulations slated for long term storage, will rely on a useful range of total osmolarity to both promote long term stability at temperature of 2-8° C., or higher, while also making the formulation useful for parenteral injection. For example, but not necessarily, an effective range of total osmolarity (the total number of molecules in solution) may be from about 200 mOs/L to about 800 mOs/L. It will be apparent that the amount of a cyroprotectant, such as sucrose or sorbitol, will depend upon the amount of salt in the formulation in order for the total osmolarity of the solution to remain within an appropriate range. Therefore a salt free formulation may, but not necessarily, contain from about 5% to about 25% sucrose.

Alternatively, a salt free sorbitol-based formulation may, but not necessarily, contain sorbitol within a range from about 3% to about 12%. Salt-free formulations will of course warrant increased ranges of the respective cryoprotectant in order to maintain effective osmolarity levels. These formulation may also contain a divalent cation (including but not necessarily limited to $MgCl_2$, $CaCl_2$ and $MnCl_2$); and a non-32 ionic surfactant (including but not necessarily limited to Polysorbate-80 (Tween 80®), Polysorbate-60 (Tween 60®), Polysorbate-40 (Tween 40®) and Polysorbate-20 (Tween 20®), polyoxyethylene alkyl ethers, including but not limited to Brij 58®, Brij 35®, as well as others such as Triton X-100®, Triton X 114®, NP40®, Span 85 and the Pluronic series of non-ionic surfactants (e.g., Pluronic 121)). Any combination of such components, including probable inclusion of a bacteriostat, may be useful to fill the antibody-containing formulations of the present disclosure. The anti-HCMV antibodies or antigen-binding portions thereof of the present disclosure may also be a "chemical derivative", which describes antibodies that contain additional chemical moieties which are not normally a part of the immunoglobulin molecule (e.g., pegylation). Such moieties may improve the solubility, half-life, absorption, etc. of the base molecule. Alternatively the moieties may attenuate undesirable side effects of the base molecule or decrease the toxicity of the base molecule.

For in vivo treatment of human and non-human patients, the patient is administered or provided a pharmaceutical formulation including at least one anti-HCMV antibody or antigen-binding portions thereof of the present disclosure. When used for in vivo therapy, the anti-HCMV antibodies or antigen-binding portions thereof of the invention are administered to the patient in therapeutically effective amounts (i.e., amounts that eliminate or reduce the total bacterial load). The antibodies are administered to a human patient, in accord with known methods, such as intravenous administration, for example, as a bolus or by continuous infusion over a period of time, by intramuscular, intraperitoneal, intracerobrospinal, subcutaneous, intra-articular, intrasynovial, intrathecal, oral, topical, or inhalation routes. The antibodies or antigen-binding portions thereof can be administered parenterally, when possible, at the target cell site, or intravenously. In some embodiments, antibody is administered by intravenous or subcutaneous administration. Therapeutic compositions of the invention may be administered to a patient or subject systemically, parenterally, or locally. The above parameters for assessing successful treatment and improvement in the disease are readily measurable by routine procedures familiar to a physician.

For parenteral administration, the anti-HCMV antibodies or antigen-binding portions thereof may formulated in a unit dosage injectable form (solution, suspension, emulsion) in association with a pharmaceutically acceptable, parenteral vehicle. Examples of such vehicles include, but are not limited, water, saline, Ringer's solution, dextrose solution, and 5% human serum albumin. Non-aqueous vehicles include, but are not limited to, fixed oils and ethyl oleate. Liposomes can be used as carriers. The vehicle may contain minor amounts of additives such as substances that enhance isotonicity and chemical stability, such as, for example, buffers and preservatives.

The anti-HCMV antibodies or antigen-binding portions thereof of the present disclosure may be administered to the host in any manner, strategy and/or combination available in the art in amounts sufficient to offer a therapeutic treatment against human cytomegalovirus. These compositions may be provided to the individual by a variety of routes known in the art, especially parenteral routes, including but in no way limited to parenteral routes such as intravenous (IV), intramuscular (IM); or subcutaneous (SC) administration, with IV administration being the norm within the art of therapeutic antibody administration. These compositions may be administered as separate or multiple doses (i.e., administration of the antibody at staggered times by maintaining the sterile condition of the formulation through the treatment regime).

The dose and dosage regimen depends upon a variety of factors readily determined by a physician, such as the nature of the infection, for example, its therapeutic index, the patient, and the patient's history. Generally, a therapeutically effective amount of an antibody is administered to a patient. In some embodiments, the amount of antibody administered is in the range of about 0.001 mg/kg to about 1000 mg/kg of patient body weight, and any range in between. Depending on the type and severity of the infection, about 0.1 mg/kg to about 50 mg/kg body weight (for example, about 0.1-15 mg/kg/dose) of antibody is an initial candidate dosage for administration to the patient, whether, for example, by one or more separate administrations, or by continuous infusion. The anti-HCMV antibodies can be delivered relatively low volume rates, for example but not necessarily from about 0.001 ml/day to 10 ml/day so as to minimize tissue disturbance or trauma near the site where the formulation is released. The formulation may be released at a rate of, depending on the specific biological agent(s), at a low dose, e.g., from about 0.01 µg/hr or 0.1 µg/hr, 0.25 µg/hr, 1 µg/hr, generally up to about 200 µg/hr, or the formulation is delivered at a low volume rate e.g., a volume rate of from about 0.001 ml/day to about 1 ml/day, for example, 0.01 micrograms per day up to about 20 milligrams per day. Dosage depends on a number of factors such as potency, bioavailability, and toxicity of the active ingredient used (e.g. the anti-HCMV antibodies or antigen-binding portions thereof) and the requirements of the subject. The progress of this therapy is readily monitored by conventional methods and assays and based on criteria known to the physician or other persons of skill in the art. The above parameters for assessing successful treatment and improvement in the disease are readily measurable by routine procedures familiar to a physician.

Specific embodiments for delivery vehicles for anti-HCMV antibodies of the present disclosure include PLGA microspheres, as discussed herein and as further known in the art, as well as polymer-based non-degradable vehicles comprising poly (ethylene-co-vinyl acetate; PEVAc). Additionally, controlled-release and localized delivery of antibody-based therapeutic products is reviewed in Grainger, et al., 2004, Expert Opin. Biol. Ther. 4(7): 1029-1044), hereby incorporated by reference in its entirety. Suitable microcapsules capable of encapsulating the antibody may also include hydroxymethylcellulose or gelatin-microcapsules and polymethyl methacrylate microcapsules prepared by coacervation techniques or by interfacial polymerization. See PCT publication WO 99/24061 entitled "Method for Producing IGF-1 Sustained-Release Formulations," wherein a protein is encapsulated in PLGA microspheres, this reference which is hereby incorporated herein by reference in its entirety. In addition, microemulsions or colloidal drug delivery systems such as liposomes and albumin microspheres, may also be used. Other preferred sustained-release compositions employ a bioadhesive to retain the antibody at the site of administration. As noted above, the sustained-release formulation may comprise a biodegradable polymer into which the antibody is disposed, which may provide for non-immediate release. Non-injectable devices may be described herein as an "implant", "pharmaceutical depot implant", "depot implant", "non-injectable depot" or some such similar term. Common depot implants may include, but are not limited to, solid biodegradable and non-biodegradable polymer devices (such as an extended polymer or coaxial rod shaped device), as well as numerous pump systems also known in the art. Injectable devices are split into bolus injections (release and dissipation of the drug subsequent to injection), and repository or depot injections, which provide a storage reservoir at the site of injection, allowing for sustained-release of the biological agent over time. A depot implant may be surgically tethered to the point of delivery so as to provide an adequate reservoir for the prolonged release of the antibody over time. Such a device will be capable of carrying the drug formulation in such quantities as therapeutically or prophylactically required for treatment over the pre-selected period. The depot implant may also provide protection to the formulation from degradation by body processes (such as proteases) for the duration of treatment. As known in the art, the term "sustained-release" refers to the gradual (continuous or discontinuous) release of such an agent from the block polymer matrix over an extended period of time. Regardless of the specific device, the sustained-release of the composition will result in a local biologically effective concentrations of the antibody. A sustained release of the biological agent(s) will be for a period of a single day, several days, a week or more; but most likely for a month or more, or up to about six months, depending on the formulation. Natural or synthetic polymers known in the art will be useful as a depot implant due to characteristics such as versatile degradation kinetics, safety, and biocompatibility. These copolymers can be manipulated to modify the pharmacokinetics of the active ingredient, shield the agent from enzymatic attack, as well as degrading over time at the site of attachment or injection. The artisan will understand that there are ample teachings in the art to manipulate the properties of these copolymers, including the respective production process, catalysts used, and final molecular weight of the sustained-release depot implant or depot injection. Natural polymers include but are not limited to proteins (e.g., collagen, albumin or gelatin); polysaccharides (cellulose, starch, alginates, chitin, chitosan, cyclodextrin, dextran, hyaluronic acid) and lipids. Biodegradable synthetic polymers may include but are not limited to various polyesters, copolymers of L-glutamic acid and gamma ethyl-L-glutamate (Sidman et al., 1983, Biopolymers 22:547-556), polylactides ([PLA]; U.S. Pat. No. 3,773,919 and EP 058,481), polylactate polyglycolate (PLGA) such as polylactide-co-glycolide (see, for example, U.S. Pat. Nos. 4,767,628 and 5,654,008), polyglycolide (PG), polyethylene glycol (PEG) conjugates of poly(α-hydroxy acids), polyorthoesters, polyaspirins, polyphosphagenes, vinylpyrrolidone, polyvinyl alcohol (PVA), PVA-g-PLGA, PEGT-PBT copolymer (polyactive), methacrylates, poly(N-isopropylacrylamide), PEO-PPO-PEO (pluronics), PEO-PPO-PAA copolymers, PLGA-PEO-PLGA, polyorthoesters (POE), or any combinations thereof, as described above (see, for example, U.S. Pat. No. 6,991,654 and U.S. Pat. Appl. No. 20050187631, each of which is incorporated herein by reference in its entirety, hydrogels (see, for example, Langer et al., 1981, J. Biomed. Mater. Res. 15:167-277; Langer, 1982, Chem. Tech. 12:98-105, non-degradable ethylene-vinyl acetate (e.g. ethylene vinyl acetate disks and poly(ethylene-co-vinyl acetate)), degradable lactic acid-glycolic acid copolymers such as the Lupron Depot™, poly-D-(-)-3-hydroxybutyric acid (EP 133,988), hyaluronic acid gels (see, for example, U.S. Pat. No. 4,636,524), alginic acid suspensions, polyorthoesters (POE), and the like. Polylactide (PLA) and its copolymers with glycolide (PLGA) have been well known in the art since the commercialization of the Lupron Depot™, approved in 1989 as the first parenteral sustained-release formulation utilizing PLA polymers. Additional examples of products which utilize PLA and PLGA as excipients to achieve sustained-release of the active ingredient include Amidox (PLA; periodontal disease), Nutropin Depot (PLGA; with hGH), and the Trelstar Depot (PLGA; prostate cancer). Other synthetic polymers included but are not limited to poly(c-caprolactone), poly3-hydroxybutyrate, poly(β-malic acid) and poly(dioxanone)]; polyanhydrides, polyurethane (see WO 2005/013936), polyamides, cyclodestrans, polyorthoesters, n-vinyl alcohol, polyethylene oxide/polyethylene terephthalate, polyphosphate, polyphosphonate, polyorthoester, polycyanoacrylate, polyethylenegylcol, polydihydropyran, and polyacytal. Non-biodegradable devices include but are not limited to various cellulose derivatives (carboxymethyl cellulose, cellulose acetate, cellulose acetate propionate, ethyl cellulose, hydroxypropyl methyl cellulose) silicon-based implants (polydimethylsiloxane), acrylic polymers, (polymethacrylate, polymethylmethacrylate, polyhydroxy(ethylmethylacrylate), as well as polyethylene-co-(vinyl acetate), poloxamer, polyvinylpyrrolidone, poloxamine, polypropylene, polyamide, polyacetal, polyester, poly ethylene-chlorotrifluoroethylene, polytetrafluoroethylene (PTFE or "Teflon™"), styrene butadiene rubber, polyethylene, polypropylene, polyphenylene oxide-polystyrene, poly-a-chloro-p-xylene, polymethylpentene, polysulfone and other related biostable polymers. Carriers suitable for sustained-release depot formulations include, but are not limited to, microspheres, films, capsules, particles, gels, coatings, matrices, wafers, pills or other pharmaceutical delivery compositions. Examples of such sustained-release formulations are described above. See also U.S. Pat. Nos. 6,953,593; 6,946,146; 6,656,508; 6,541,033; and 6,451,346, the contents of each which are incorporated herein by reference. The dosage form must be capable of carrying the drug formulation in such quantities and concentration as therapeutically required for treatment over the pre-selected period, and must provide sufficient protection to the formulation from degradation by body processes for the duration of treatment. For example, the dosage form can be surrounded by an exterior made of a material that has properties to protect against degradation from metabolic processes and the risk of, e.g., leakage, cracking, breakage, or distortion. This can prevent expelling of the dosage form contents in an uncontrolled manner under stresses it would be subjected to during use, e.g., due to physical forces exerted upon the drug release device as a result of normal joint articulation and other movements by the subject or for example, in convective drug delivery devices, physical forces associated with pressure generated within the reservoir. The drug reservoir or other means for holding or containing the drug must also be of such material as to avoid unintended reactions with the active agent formulation, and is preferably biocompatible (e.g., where the dosage form is implanted, it is substantially non-reactive with respect to a subject's body or body fluids). Generally, the anti-HCMV antibodies are administered to an individual for at least 12 hours to at least a week, and most likely via an implant designed to deliver a drug for at least 10, 20, 30, 100 days or at least 4 months, or at least 6 months, 12 months, 24 months or more, as required.

In some embodiments, the anti-HCMV antibodies or antigen-binding portions thereof of the present disclosure may be co-administered with one or more additional treatments for HCMV, e.g. co-administered with one or more antivirals and/or additional anti-HCMV antibodies or antigen-binding portions thereof, including but not limited to additional anti-HCMV antibodies or antigen-binding portions thereof of the present disclosure. The most common antiviral treatment for HCMV is ganciclovir, and accordingly in one embodiment the anti-HCMV antibodies or antigen-binding portions thereof of the present disclosure may be co-administered with ganciclovir. Other antivirals that would be acceptable include valganciclovir, forscarnet, and cidofovir, either in combination or alone, including in combination with ganciclovir. Additionally, co-administration may or may not be with additional anti-HCMV antibodies or antigen-binding portions thereof. Purely by way of example, those anti-HCMV antibodies which specifically bind to one or more epitopes within SEQ ID NO: 1 (e.g. 10C10 and 5C3) may be administered with additional anti-HCMV antibodies or antigen-binding portions thereof, including those that also target glycoprotein gH (but target a different epitope) such as MSL-109, as although previous studies have shown that human-derived MSL-109 is not broadly neutralizing, MSL-109 may be effective in combination with those anti-HCMV antibodies which specifically bind to one or more epitopes within SEQ ID NO: 1 (e.g. 10C10 and 5C3 or recombinant antibodies generated using the variable heavy/light regions or CDRs of such). Likewise, anti-HCMV antibodies which specifically bind to one or more epitopes within SEQ ID NO: 1 may be administered with antibodies that target glycoprotein gB, including the present anti-HCMV antibodies that target gB, as although not broadly neutralizing, are capable of neutralizing infection in at least some strains. For example, although 8H12 has not shown to be broadly neutralizing by itself, it may be effective in combination with those anti-HCMV antibodies which specifically bind to one or more epitopes within SEQ ID NO: 1 (e.g. 10C10 and 5C3 or recombinant antibodies generated using the variable heavy/light regions or CDRs of such) and thus should be considered part of this invention. The anti-HCMV antibodies or antigen-binding portions thereof that specifically target glycoprotein gH or antigenic fragments thereof may possibly combined other anti-HCMV antibodies or antigen-binding portions thereof, such as those targeting glycoprotein gL, which may be especially effective considering how glycoprotein gL is involved with gH in a heterodimer, trimer, and pentamer, or even anti-HCMV antibodies or antigen-binding portions thereof that target other antigens on the viral surface of HCMV, e.g. UL128, UL130 and/or UL131a. The anti-HCMV antibodies or antigen-binding portions thereof of the present disclosure may be administered with a variety of additional existing antibodies, such as Cytogam®. These antibody combinations may or may not be co-administered with one or more antivirals, e.g. ganciclovir, valganciclovir, forscarnet, and/or cidofovir, and any other appropriate antivirals. Co-administration of the anti-HCMV antibodies of the present disclosure with each other or any other anti-HCMV antibodies and/or antivirals may or may not take place concurrently.

According to another embodiment, the present disclosure provides a passive vaccine or pharmaceutical compositions containing at least one anti-HCMV antibody or antigen-binding portions thereof of the invention and a pharmaceutically acceptable carrier. According to one embodiment, the vaccine or pharmaceutical compositions is a composition containing at least one antibody described herein and a pharmaceutically acceptable excipient. The vaccine can include a plurality of the antibodies having the characteristics described herein in any combination and can further include other anti-HCMV antibodies or antigen-binding portions thereof. The passive vaccine may comprise one or more pharmaceutically acceptable preservatives, carriers, and/or excipients, which are known in the art. In other embodiments, the present disclosure provides an active vaccine or pharmaceutical compositions containing HCMV or an antigenic fragment thereof. If HCMV is used, it may be attenuated. It may be heat-killed. If antigenic fragments are utilized, it may be preferable, although not necessary, to use glycoprotein gH, although fragments of glycoprotein gH such as those including SEQ ID NO: 1 may be acceptable, although the fragments containing SEQ ID NO: 1 should be large enough as to ensure that a proper conformational epitope is formed.

The present compositions may be used in an immunogenic composition to immunize an animal. Such immunogenic composition according to the invention may be used for the preparation of a vaccine. Preferably a prophylactic and/or therapeutic vaccine is produced. Thus, within the scope of this invention is an immunogenic or vaccine composition that contains a pharmaceutically acceptable carrier and an effective amount of an antigen as described supra. The carriers used in the composition can be selected on the basis of the mode and route of administration, and standard pharmaceutical practice. The composition can also contain an adjuvant. Examples of an adjuvant include a cholera toxin, *Escherichia coli* heat-labile enterotoxin, liposome, unmethylated DNA (CpG) or any other innate immune-stimulating complex. Various adjuvants that can be used to further increase the immunological response depend on the host species and include Freund's adjuvant (complete and incomplete), mineral gels such as aluminum hydroxide, surface-active substances such as lysolecithin, pluronic polyols, polyanions, peptides, oil emulsions, keyhole limpet hemocyanin, and dinitrophenol.

A vaccine formulation may be administered to a subject per se or in the form of a pharmaceutical or therapeutic composition. Compositions of the invention and an adjuvant may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries which facilitate processing of the antigens of the invention into preparations which can be used pharmaceutically. Proper formulation is dependent upon the route of administration chosen.

For injection, vaccine preparations may be formulated in aqueous solutions, preferably in physiologically compatible buffers such as Hanks' solution, Ringer's solution, phosphate buffered saline, or any other physiological saline buffer. The solution may contain formulatory agents such as suspending, stabilizing and/or dispersing agents. Alternatively, the composition may be in powder form for constitution with a suitable vehicle, e.g., sterile pyrogen-free water, before use.

The amount of a composition administered depends, for example, on the particular antigen in the composition, whether an adjuvant is co-administered with the antigen, the type of adjuvant co-administered, the mode and frequency of administration, and the desired effect (e.g., protection or treatment), as can be determined by one skilled in the art. Determination of an effective amount of the vaccine formulation for administration is well within the capabilities of those skilled in the art, especially in light of the detailed disclosure provided herein. An effective dose can be estimated initially from in vitro assays. For example, a dose can be formulated in animal models to achieve an induction of an immune response using techniques that are well known in the art. One having ordinary skill in the art could readily optimize administration to all animal species based on results described herein. Dosage amount and interval may be adjusted individually. For example, when used as a vaccine, the vaccine formulations of the invention may be administered in about 1 to 3 doses for a 1-36 week period. Preferably, 1 or 2 doses are administered, at intervals of about 3 weeks to about 4 months, and booster vaccinations may be given periodically thereafter. Alternative protocols may be appropriate for individual animals. A suitable dose is an amount of the vaccine formulation that, when administered as described above, is capable of raising an immune response in an immunized animal sufficient to protect the animal from an infection for at least 4 to 12 months. In general, the amount of the antigen present in a dose ranges from about 1 pg to about 100 mg per kg of host, typically from about 10 pg to about 1 mg, and preferably from about 100 pg to about 1 pg. Suitable dose range will vary with the route of injection and the size of the subject, but will typically range from about 0.1 mL to about 5 mL. Additional boosters can be given as needed.

F. Equivalents

Where a value of ranges is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Although any methods and materials similar or equivalent to those described herein can also be used in the practice or testing of the present disclosure, the preferred methods and materials are now described. All publications mentioned herein are incorporated herein by reference in their entireties.

As used herein and in the appended claims, the singular forms "a", "and" and "the" include plural references unless the context clearly dictates otherwise.

The term "about" refers to a range of values which would not be considered by a person of ordinary skill in the art as substantially different from the baseline values. For example, the term "about" may refer to a value that is within 20%, 15%, 10%, 9%, 8%, 7%, 6%, 5%, 4%, 3%, 2%, 1%, 0.5%, 0.1%, 0.05%, or 0.01% of the stated value, as well as values intervening such stated values. Context will dictate what is appropriate in each circumstance.

Publications disclosed herein are provided solely for their disclosure prior to the filing date of the present disclosure. Nothing herein is to be construed as an admission that the present disclosure is not entitled to antedate such publication by virtue of prior invention. Further, the dates of publication provided may be different from the actual publication dates which may need to be independently confirmed.

Each of the applications and patents cited in this text, as well as each document or reference, patent or non-patent literature, cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference in their entirety. More generally, documents or references are cited in this text, either in a Reference List before the claims; or in the text itself; and, each of these documents or references ("herein-cited references"), as well as each document or reference cited in each of the herein-cited references (including any manufacturer's specifications, instructions, etc.), is hereby expressly incorporated herein by reference.

The following non-limiting examples serve to further illustrate the present disclosure.

VII. EXAMPLES

These examples identify and characterize potent, broad-spectrum human cytomegalovirus (HCMV) antibodies, specifically monoclonal antibodies (mAbs) that block infection of multiple cell types through a non-biased screening approach. High throughput selection of hybridomas derived from CMV-inoculated mice coupled with high-content neutralization (HCN) assays based on YFP reporter viruses were utilized to rapidly screen a large hybridoma library and identify an initial panel of 7 neutralizing mAbs. Two mAbs targeting the gH glycoprotein displayed remarkable potency, broad-spectrum properties, and the ability to inhibit both cell-free and cell-cell viral dissemination. Detailed biochemical characterization revealed that the gH mAbs bind to both the gH trimer and gH pentamer complexes, and the generation of conformational epitope libraries led to identification of a core binding region (SEQ ID NO: 1) in the central alpha helix-rich domain of the gH glycoproteins. In addition to developing anti-HCMV antibodies, the platform described here has led to the identification of an epitope within HCMV glycoprotein gH that is highly susceptible to antibody-mediated neutralization.

1. Generation of Broadly-Neutralizing Anti-HCMV Antibodies

In this example, broad-spectrum anti-HCMV antibodies were generated using a high-throughput neutralization (HTN) assay. The measurement of fluorescent emission from cells infected with HCMV reporter strains provides an accurate proxy of HCMV infection levels. To validate that the reporter HCMV strain AD169 encoding for a chimeric IE2 protein Yellow Fluorescent Protein (YFP) (AD169$_{IE2-YFP}$) could be utilized in a neutralization assay, various sources of anti-HCMV antibodies were tested for their neutralizing properties. HCMV-positive serum, purified anti-gH mAb 14-4b, supernatant from 14-4b hybridoma, and as controls HCMV-negative serum, an isotype control directed to MHCI heavy chain peptide (HC-10), and supernatant from anti-human CD44 hybridoma were pre-incubated with AD169$_{IE2-YFP}$ virus before adding to MRC5 cells. Fluorescence intensity from infected cells was than measured at 16 hpi using an Acumen $^eX3$ fluorescent cytometer. Comparing mock-infected cells as 100% infection, purified 14-4b and supernatant from the 14-4b hybridoma were capable of neutralizing HCMV infection, while the isotype controls had no effect on infection levels, and the decrease of HCMV infection from virus incubated with HCMV-positive serum further validated the neutralization assay (FIG. 1A). Together the data support the validity of an AD169$_{IE2-YFP}$-based neutralization assay to identify neutralizing antibody clones.

The use of a rapid and accurate fluorescent readout for quantifying HCMV infection presented an excellent strategy for the identification of novel neutralizing HCMV-antibodies. It was hypothesized that antibodies targeting the core binding and fusion envelope proteins (e.g. gB, gH, gL) would provide the best targets for broad-spectrum antibodies. To that end, mice were immunized with the lab strain AD169 because it expresses the core entry factors and lacks the pentamer complex due to the deletion of UL131a. The lack of the pentameric complex would thus exclude the generation of antibodies to the immunodominant UL128, UL130, and UL131 proteins. Following a series of immunization and boosts with purified virus, serum samples from various mice were analyzed for neutralization activity using the AD169$_{IE2\text{-}YFP}$ neutralization assay (FIG. 1B). A significant reduction in infection was observed with serum from immunized mice and HCMV-seropositive individual, but not when pre-incubated with normal mouse serum (NMS). The data indicated that AD169-inoculated mice possess circulating antibodies capable of neutralizing a CMV infection.

Subsequently, ~2000 hybridoma clones were generated from the spleen of two mice using an automated clone picker to generate individual clones for identification of neutralizing antibodies. Supernatant from each hybridoma was subjected to the AD169$_{IE2\text{-}YFP}$-MRC5 HTN assay. Following an initial neutralization assay (FIG. 7A), clones that decreased infection by at least 50% were further examined in a dose-dependence HTN assay to identify six clones that consistently limited a virus infection (FIG. 7B). The six hybridoma clones were expanded and subjected to a 5-point dose-dependence HTN assay (FIG. 1D). All six hybridoma clones displayed dose-dependent neutralization capability, with clones 5C3 and 10C10 displaying significant neutralization at all dilutions.

To determine whether the neutralizing clones target viral glycoproteins, MRC5 fibroblasts infected with AD169$_{IE2\text{-}YFP}$ (MOI: 3) were subjected to flow cytometry with hybridoma clones (FIGS. 1D and 1E). Optimization of assay conditions using anti-gH mAb 14-4b (FIG. 1E) demonstrated that only a small proportion of double-positive cells were observed at 96 hpi and was dramatically enhanced upon permeabilization with 0.1% saponin (FIG. 1E, bottom row). The data showed the majority of gH expressed during an infection is localized within intracellular compartments. The reactivity of the antibodies was examined in the neutralizing hybridomas to label permeabilized, AD169$_{IE2\text{-}YFP}$-infected cells (FIG. 1F). All of the neutralizing clones exclusively labeled virus-infected cells, while a non-neutralizing hybridoma supernatant was negative. The data showed that the targets of the HCMV-neutralizing antibodies demonstrate similar expression kinetics as a quintessential HCMV glycoprotein.

2. Identification of the HCMV-Neutralizing Antibody Viral Glycoprotein Targets

To determine the antigenic target(s) of the HCMV-neutralizing antibodies, an initial $^{35}$S-methionine metabolic labeling experiment was conducted. MRC5 fibroblasts infected with AD169$_{IE2\text{-}YFP}$ (MOI: 5) were pulsed at 72 hpi for 12 hours prior to cell lysis. The antigenic targets of the neutralizing antibodies or an isotype control specific to GFP were recovered from cell lysates and resolved on a SDS-polyacrylamide gel (FIG. 2A). The neutralizing antibodies recovered various polypeptides segregating into two distinct groups. Group I antibodies recovered 3 major protein species that migrated at ~130 kDa, 100 kDa, and 60 kDa, respectively (FIG. 2A, left panel); a result consistent with immature and mature forms of the gB protein. The neutralizing mAbs 10C10 and 5C3 (group II) recovered distinct protein species that migrated at ~100 kDa, 37 kDa, and 12 kDa, respectively (FIG. 2A, right panel). The migration pattern of proteins was consistent with gH complexes that include gH, gL and UL128. It was further validated that the mAbs target were glycoproteins. The proteins recovered with the neutralizing mAbs from metabolically labeled AD169$_{IE2\text{-}YFP}$-infected cells were subjected to peptide-N-Glycosidase F (PNGaseF) digestion (FIG. 2B). PNGase digestion of the putative gB proteins resulted in a shift in all three major peptide species (FIG. 2B, left panel). Similarly, the putative gH-complex proteins gH and gL demonstrated a shift following PNGase digestion (FIG. 2B, right panel). Thus it was concluded that the neutralizing antibodies identified in the screen recover glycosylated protein species.

As further confirmation of the identity of the proteins precipitated by the neutralizing antibodies, protein complexes recovered from AD169-infected fibroblasts with the Group I mAb 2F4 and Group II mAb 10C10 were resolved by SDS-PAGE and the predominant polypeptides were subjected to mass spectrometry analysis. The excised polypeptides recovered with 2F4 identified gB, while the 5C3-recovered proteins correspond to gH and gL peptides (Table 4). The data indicated that the neutralizing antibodies recover complexes that possess gH and gB glycoproteins.

To verify that the protein targets of the neutralizing antibodies were gB and gH, U373 glioblastoma cell lines expressing either the gH or gB protein that were cloned from the HCMV strain TB40/E (U373$^{gH}$ and U373$^{gB}$) were generated (FIG. 2C). An initial immunoblot analysis of total cell lysates from U373$^{gH}$ or U373$^{gB}$ with an anti-gB (FIG. 2C, lanes 1 and 2) and anti-gH (FIG. 2C, lanes 3 and 4) antibody validated the stable expression of gH or gB in the cell lines. U373$^{gH}$ and U373$^{gB}$ cells were next used in a flow cytometry assay to measure binding by the neutralizing antibodies (FIG. 2D). Staining with the anti-MHCI heavy chain antibody W6/32 demonstrated proper conditions for antibody labeling and detection by flow cytometry (FIG. 8A). Group I antibodies 5A6, 7H7, 8H2, and 2F4, bound preferentially to the U373$^{gB}$ cells rather than the U373$^{gH}$ cells (FIG. 2D, left column), while the anti-gH antibody 14-4b, and the Group I antibodies 5C3 and 10C10 both bound preferentially to U373$^{gH}$ cells rather than U373$^{gB}$ cells (FIG. 2D, right column). This supported the hypothesis that group I neutralizing mAbs from the panel targeted HCMV gB, while the group II mAbs targeted HCMV gH.

In further validating that the antibodies recognize either gB or gH, the neutralizing antibodies were incubated with cell lysates from U373$^{gH}$ and U373$^{gB}$ cells and the recovered proteins were subjected to either an anti-gB or anti-gH immunoblot (FIG. 2E). The group I neutralizing mAbs 2F4, 5A6, 7H7, and 8H2 recovered gB proteins only from U373$^{gB}$ cell lysates (FIG. 2E, top panel, lanes 5-8), while the control gH mAb, 14-4b, along with group II neutralizing mAbs 10C10 and 5C3 recovered gH proteins only from U373$^{gH}$ cell lysates (FIG. 2E, bottom panel, lanes 13-15). Taken together, the data indicated that the neutralizing antibodies bind to the HCMV glycoproteins gB and gH. To determine if the antibodies recognize a linear epitope, the HCMV-neutralizing hybridomas were used to probe total cell lysates from U373$^{gH}$ and U373$^{gB}$ cell lines by immunoblot analysis (FIG. 8B). No polypeptides were identified in any of the samples indicating that the neutralizing antibodies bind to conformational epitopes of their respective target.

TABLE 4

| | | Excised polypeptides | | | | |
|---|---|---|---|---|---|---|
| Antibody Group | Clone | Molecular Weight (kDa) | Rank | Log(I) | Gene | Protein |
| 1 | 2F4 | 130 | 1 | 7.8 | UL55 | gB |
| 2 | 10C10 | 100 | 1 | 8.01 | UL75 | gH |
| | | 30 | 1 | 7.74 | UL115 | gL |

3. Analysis of the Potency of HCMV-Neutralizing Antibodies

In order to examine the specificity of our HCMV-neutralizing antibodies, a reporter virus derived from the TB40/E HCMV strain was utilized, in which the US28 coding region was replaced with a DNA cassette encoding a FLAG-tagged YFP chimera (TB40/E$_{FLAG-YFP}$). The TB40/E$_{FLAG-YFP}$ strain creates a robust fluorescent signal in the cytoplasm of infected cells that can be visualized beginning at 48 hpi and increasing in intensity throughout the infection cycle. TB40/E$_{FLAG-YFP}$ pre-incubated with α-gH and α-gB supernatants at 3 concentrations was used to infect MRC5 fibroblasts. At 120 hpi, fluorescence intensity was used to determine the number of YFP+ cells to calculate % infection using a non-neutralizing hybridoma as 100% (FIG. 3A). Surprisingly, while supernatant from α-gH hybridomas 14-4b, 10C10 and 5C3 significantly blocked infection at all concentrations, the gB antibodies did not reduce infection levels at any of the dilutions tested. These results imply that the anti-gB mAbs, while potentially being capable of neutralizing individual HCMV viral strains, do not broadly-inhibit a HCMV infection by themselves.

To further assess the potency of the antibody panel, the IC50 values of the neutralizing antibodies were calculated using a AD169$_{IE2-YFP}$ or TB40/E$_{FLAG-YFP}$ HTN assay (FIGS. 3B, 3C, and 3D). The neutralizing capability of the antibodies was compared to Cytogam® antibodies, a commercially-available polyclonal IgG preparation derived from HCMV seropositive individuals and currently used for treatment of reactivated HCMV infection. All of the antibodies from the panel potently neutralized AD169$_{IE2-YFP}$ infection, with IC50 values ranging from 0.24 µg/mL (5C3) to 5.2 µg/mL (7H7) (FIGS. 3C, 3D, left columns), while the Cytogam® polyclonal antisera exhibited an IC50 value of 18.62 µg/mL (FIG. 3B, left column). Anti-gH antibodies 10C10 and 5C3 displayed potent neutralization of TB40/E$_{FLAG-YFP}$ infection, with IC50 values of 0.38 µg/mL and 0.07 µg/mL, respectively (FIG. 3C, right column). The Cytogam® polyclonal antisera exhibited also displayed an improved IC50 value of 0.46 µg/mL (FIG. 3B, right column). Strikingly, purified anti-gB antibodies were unable to reduce infection levels, even at a concentration exceeding 24 µg/mL (FIG. 3D, right column). To determine whether the anti-gB antibodies were capable of binding to the gB protein from the TB40/E strain, the anti-gB neutralizing mAbs were incubated with lysates from TB40/E WT-infected MRC5 cells and the recovered proteins were subjected to an anti-gB immunoblot (FIG. 3E). All gB antibodies were capable of recovering gB protein from TB40/E-infected cells. Although the gB-specific antibodies were capable of binding to the TB40/E gB protein, they were unable to neutralize a TB40/E infection. Collectively, the data demonstrate that the neutralizing antibody panel consists of anti-gH and anti-gB antibodies with diverse potency.

4. Analysis of the Ability of Anti-gH Antibodies to Block Viral Infection and Dissemination The ability of the α-gH antibodies to neutralize additional clinical-like CMV strains was examined. Monoclonal antibodies 10C10 and 5C3 were pre-incubated with HCMV strains TB40/E, DAVIS, VHL/E, and TR at 9 µg/mL prior to infection of MRC5 fibroblasts. At 72 hpi, total cell lysate were subjected to immunoblot analysis using an antibody to late antigen (FIG. 9A). Cells infected with non-treated virus demonstrated late antigen expression in all cases while cells infected with virus samples pre-incubated with 10C10 or 5C3 showed a nearly complete reduction of late antigen expression. This data demonstrates that α-gH antibodies are capable of limiting clinical HCMV infection in fibroblasts.

To determine the potency of the α-gH mAbs against clinical-like strains, w a HTN assay using a fluorescently labeled antibody against the Immediate Early (IE) gene product (α-IE$^{FITC}$) was developed. AD169WT, TB40/EWT, VHL/E, and TR were pre-incubated with increasing concentrations of α-gH mAb or Cytogam® antibodies (FIG. 4A) followed by analysis of α-IE$^{FITC}$+ cells and the determination of the % infection. Both mAbs 10C10 and 5C3 potently neutralized infection of fibroblasts by clinical-like strains with IC50 values ranging from 0.28 µg/mL to 4.18 µg/mL (FIG. 4C, top two rows, and Table 5), while the Cytogam® antibodies were unable to block any of the viral infections at identical concentrations (FIG. 4C, bottom row, and Table 5).

Finally, to assess how α-gH mAbs affect HCMV proliferation, plaque reduction assays were performed in MRC5 cells infected with clinical-like strains DAVIS, TB40/EWT, VHL/E and TR (FIG. 4B). The α-gH mAbs reduced infection by all of the clinical strains analyzed with IC50 values ranging between 0.02 µg/mL and 2.43 µg/mL (FIG. 4B, top two rows, and Table 5). Strikingly, the Cytogam® antibodies were unable to limit plaque numbers of any of the clinical-like strains with the exception of VHL/E, where it exhibited an IC50 of 0.12 µg/mL (FIG. 4B, bottom row, and Table 5). These data demonstrated the ability of the neutralizing anti-HCMV mAbs to block cell-free infection and limit viral dissemination.

5. Examination of the Broad-Spectrum Neutralization Capability of Anti-gH mAbs in Epithelial Cells To further analyze the efficacy of the α-gH mAbs as a broad spectrum anti-viral, the potency in blocking virus infection of human retinal pigment epithelial cells (ARPE-19) was examinde. Accordingly, the TB40/E$_{FLAG-YFP}$ reporter strain was utilized to measure the efficacy of α-gH mAbs to block infection of ARPE-19 cells (FIG. 9B). The mAbs 10C10 and 5C3 potently blocked infection with IC50 values of 0.13 µg/mL (10C10) and 0.04 µg/mL (5C3) (Table 5). Additionally, the capacity of 10C10 and 5C3 to inhibit infection of TB40/E-WT, VHL/E, and TR were analyzed using the HTN assay with α-IE$^{FITC}$. The IC50 values of the mAbs against the viruses ranged from 0.11 to 1.35 µg/mL (FIG. 4C, rows 1-2 and Table 5). The Cytogam® antibodies exhibited variable ability to neutralize ARPE-19 infection, with IC50 values exceeding 6 µg/mL for TB40/E WT and VHL/E infection, and 1.58 µg/mL for the clinical strain TR (FIG. 4C, bottom row and Table 5). This demonstrated that the α-gH mAbs 10C10 and 5C3 are capable of neutralizing epithelial cell infection by various clinical-like strains.

TABLE 5

Different HCMV strains and assays performed

| | Strain | | | | | | | | | |
|---|---|---|---|---|---|---|---|---|---|---|
| | AD169-IE2-YFO | TB40/E FLAG-YFP | TR | | TB40/E | | VHL/E | | | Davis |
| | | | Cell Type | | | | | | | |
| | Fibroblast | Fibroblast | Fibroblast | Epithelial | Fibroblast | Epithelial | Fibroblast | Epithelial | | Fibroblasts |
| Assay | IE2 | FLAG-YFP | Plaque α-IE | α-IE | Plaque α-IE | α-IE | Plaque α-IE | α-IE | | Plaque |
| 10C10 | 0.5 | 0.38 | 2.43 2.34 | 0.44 | 1.28 4.18 | 1.35 | 0.24 0.24 | 0.11 | | 0.37 |
| 5C3 | 0.24 | 0.07 | 2.13 0.63 | 0.16 | 0.45 0.88 | 0.96 | 0.02 0.02 | 0.11 | | 0.22 |
| Cytogam | 18.62 | 0.46 | >6.25 >12.15 | 1.58 | >6.25 >12.15 | 6.86 | 0.12 >12.15 | 10.91 | | >6.25 |

6. Examination of the Capacity of Anti-gH mAbs to Block Cell-To-Cell Dissemination To test whether the mAbs could also neutralize infection of replicated virus, transwell infection studies were conducted in fibroblast and epithelial cells (FIG. 4D). MRC5 fibroblasts in the top (transwell) layer were infected with TB40/E (moi: 1) and two days later, the membrane was inserted into a receiver well consisting of a monolayer of MRC5 fibroblasts (FIG. 4E left panel) or ARPE-19 cells (FIG. 4E, right panel). The receiver well contained various concentrations of α-gH mAb, Cytogam® antibodies, or an isotype control (0.1-44 mL). At 7 days post infection (dpi), the receiver wells were stained with α-IE$^{FITC}$ to determine number of virus-infected cells. In all cases, the anti-gH mAbs decreased infection in a dose-dependent manner, while the isotype control had no neutralization effect. In alignment with the epithelial cell neutralization data, the α-gH mAbs more potently neutralized infection of ARPE-19 cells than MRC5 cells. In contrast, the Cytogam® antibodies were only able to prevent infection in ARPE-19 cells at these concentrations. The data supports the model that anti-gH mAbs can directly inhibit virus infection of virus produced from infected cells.

To examine the ability of α-gH mAbs to block cell-to-cell dissemination, ARPE-19 cells were infected with TB40/E-WT (moi: 0.1). At 48 hpi, cell supernatant was replaced with media containing various concentrations of α-gH mAb, Cytogam® antibodies, or an isotype control (0.5-12 µg/mL). At 10 dpi, cells stained with an IE-FITC antibody to determine number of virus-infected cells. Cytogam® and α-gH mAbs were capable of limiting dissemination in a dose-dependent manner (FIG. 4F). Visualization of the infected wells revealed fewer and more diffuse IE-positive plaques in wells exposed to Cytogam® or anti-gH mAbs compared to isotype-treated cells (FIG. 4G). Additionally, infection of primary CD14+ monocytes followed by coculture with MRC5 cells in the presence of the anti-gH mAbs demonstrated their ability to block dissemination from monocytes to fibroblasts (FIG. 10). Together the data indicated that α-gH mAbs can limit both nascent cell-free dissemination to fibroblast, and epithelial cells, and limit cell-cell dissemination in epithelial cells and from fibroblasts to monocytes.

7. α-gH mAbs Bind to Multiple Glycoprotein Complexes

Given that gH undergoes extensive post-translational glycosylation and covalently binds to multiple viral proteins to generate a trimeric (gH/gL/gO) and pentameric complex (gH/gL/UL128/UL130/UL131), it was examiner whether the neutralizing α-gH mAbs recognize diverse gH-containing complexes. Protein complexes recovered by anti-HCMV mAbs 10C10 and 5C3 from TB40/E-infected cells metabolically labeled with $^{35}$S methionine at 120 hpi were subjected to PNGase treatment followed by SDS-PAGE under non-reducing conditions (FIG. 5A). Both 10C10 and 5C3 recovered protein complexes that migrated faster following PNGase treatment (FIG. 5A, lanes 3-6). Based on the relative molecular weights of the envelope glycoproteins, it was determined that the two large complexes that migrate >250 kDa are likely covalent multimers of fully glycosylated gH/gL/gO trimers (FIG. 5A, lanes 3 and 5). Furthermore, a complex that migrated at ~130 kDa likely represents the gH/gL/UL128 trimer, while proteins between 100-130 kDa are glycosylated versions of gH/gL dimers. The polypeptide <100 kDa represents the nascent gH protein. PNGase treatment resulted in faster migrating species, verifying glycosylation of the proteins (FIG. 5A, lanes 4 and 6). The data demonstrate that the anti-gH mAbs recover diverse gH-containing complexes.

To confirm the identity of the protein complexes recovered by the gH mAbs, gH complexes recovered with 10C10 and 5C3 from TB40/E-infected fibroblasts were subjected to non-reducing SDS-PAGE followed by immunoblot analysis with an α-gH mAb, rabbit anti-gL or anti-UL128 antibodies. The detection of UL128 that covalently binds to gH is used as a proxy for the pentameric complex. As predicted, the anti-gH immunoblot revealed protein complexes with a wide range of molecular weights from ~90 kDa to >250 kDa (FIG. 5B, lanes 1-3). Interestingly, the anti-gL immunoblot confirmed that the recovered complexes contained both gH and gL; more specifically the proteins between 100-130 kDa, 130, kDa, and several bands >250 kDa, (FIG. 5B, lanes 4-6). Remarkably, blotting with anti-UL128 antibody confirmed the presence of two gH/gL/128 bands at ~130 kDa (FIG. 5B, lanes 7-9). These data suggest that the antibodies can recognize gH complexed to diverse envelope proteins.

Finally, to confirm that the anti-gH antibodies were capable of binding to a region exposed on both gH/gL/gO trimer and the PC, stable U373 cell lines were constructed expressing gH, gL, and gO with a hemagglutinin (HA) tag, and cells that express gH, gL, and UL128 based on the TB40/E amino acid sequence (FIG. 5C). As expected, 10C10 and 5C3 were capable of recovering all three protein species from U373$^{gH/gL/128}$ lysates (FIG. 5C, lanes 1-3, 13-15, and 19-21). Similarly, the anti-gH mAbs were capable of precipitating gH, gL, and gO-HA from U373$^{gH/gL/gO-HA}$ cells (FIG. 5C, lanes 4-6, 10-12, and 16-18). Together, the data demonstrated that the neutralizing α-gH mAbs can interact with the gH-trimer and gH-pentameric structure, which together comprise the glycoprotein machinery involved in entry to all cell types.

8. mAb 5C3 Binds Preferentially to gH Complexes

Cell lysates from U373 cells expressing different envelope proteins were incubated with different amounts of 10C10 or 5C3 mAb (2-0.1 μg/mL) and the recovered protein complexes were resolved by SDS-PAGE and subjected to immunoblot analysis (FIG. 5D). HCMV gH recovered from U373$^{gH}$ cells revealed that 10C10 more efficiently recovered gH based on the amount of antibody that completely recovers gH (0.5 μg/ml) (FIG. 5D, lanes 1-10). This result is surprising given that neutralization studies indicated that 5C3 was more effective at neutralizing a virus infection (Table 4). It was hypothesized that the 5C3 epitope is stabilized when gH is complexed with additional glycoproteins such as gL, gO and UL128. To address this point, cell lysates from U373$^{gH/gL}$ (FIG. 5D, lanes 11-20), U373$^{gH/gL/UL128}$ (FIG. 5D, lanes 21-30), and U373$^{gH/gL/gO}$ (FIG. 5D, lanes 31-40) were incubated with 10C10 and 5C3, and the precipitates were subjected to an anti-gH immunoblot. In contrast to U373$^{gH}$ lysates, 5C3 and 10C10 were capable of recovering comparable amounts of gH indicating that 5C3 interacts preferentially with gH complexes.

9. α-gH mAbs 10C10 and 5C3 Bind to Distinct but Proximal Epitopes

To determine whether 10C10 and 5C3 recognize the same epitope on the gH protein, antibodies labeled with Alexa Fluor 647 dye were utilized in a binding competition assay. U373$^{gH/gL}$ cells were simultaneously exposed to 10C10$^{647}$ at a fixed concentration (1 μg/mL) and non-fluorescent 10C10, 5C3, or an isotype control at increasing concentrations (1-20 μg/mL) (FIG. 5F, top panel). Co-staining of 10C10$^{647}$ with an isotype control showed no decrease in fluorescence levels when compared to only 10C10$^{647}$ staining (grey peak) (FIG. 5F, left panel), even at the highest concentration of antibody tested (20 μg/mL). However, incubation of 10C10$^{647}$ with non-fluorescent 10C10 resulted in a significant dose-dependent decrease in fluorescence (FIG. 5F, center panel). The data demonstrate a specific antibody against the epitope will displace the fluorescently-labeled antibody when added in stoichiometric excess. Incubation of 5C3 with 10C10$^{647}$ did not result in a decrease of fluorescence intensity suggesting that 10C10 and 5C3 do not occupy the same epitope (right panel). To confirm this finding, the reciprocal experiment was performed. U373$^{gH/gL}$ cells were simultaneously exposed to 5C3$^{647}$ along with increasing concentration of non-labeled isotype control, 10C10, or 5C3 (FIG. 5F, bottom panel). Interestingly, while co-staining with non-labeled 10C10 did not reduce fluorescence levels to the extent seen with non-labeled 5C3, a small decrease in fluorescence signal was observed at higher concentrations of 10C10. Quantification of % fluorescence compared to maximum fluorescence observed for 5C3$^{647}$ staining of U373$^{gH/gL}$ cells revealed that 5C3 (gray bars) more efficiently displaced 5C3$^{647}$ than 10C10 (black bars) (FIG. 5G). The data illustrates that 10C10 and 5C3 bind to proximal yet distinct epitopes, and that excessive concentrations of 10C10 may interfere with binding of 5C3 due to steric occlusion.

10. Identification of 10C10 and 5C3 Epitopes

The epitope of 5C3 and 10C10 were identified by generating amino- and carboxyl-terminal mutations of gH (FIG. 11). The amino- and carboxyl-terminal truncations revealed that 5C3 recognizes an epitope between residues 295-717, while 10C10 binds to residues 132-717. In order to further identify the epitopes of 5C3 and 10C10, a cyclic peptide microarray platform (PEPperCHIP®) was utilized. Cyclic peptides of 7, 10 and 13aa long corresponding to residues 25-717 of gH with overlap of 6, 9, and 12 amino acids were generated and cyclized with a thioether linkage between the N' and C' termini to create a conformational epitope library array. The arrays were incubated with mAb 5C3 followed by an anti-mouse DyLight680 antibody and analyzed with a LI-COR Odyssey imaging system (FIG. 6A). Remarkably, 5C3 bound ~3-fold over background to a single region spanning residues 485-493 in all of the peptide libraries generated. The identified region is located in domain 2 of the gH protein according to the conventions assigned to the HSV-1 gH structure (FIG. 6B). Alignment of the HCMV gH protein was conducted using the PHYRE2 protein fold recognition server. HCMV-gH possesses significant structural homology with the gH of herpes simplex 2 (HSV-2), varicella-zoster (VZV), and Epstein-Barr (EBV). While the highest percentage identity score was assigned to EBV gH, recent evidence indicates that the HCMV gH/gL structure resembles the boot-shaped particle of the HSV gH/gL structure. Thus a 3D model of HCMV-gH was predicted based on the alignment between the hidden Markov model of the HSV-2 gH and HCMV-gH. The putative 5C3 epitope amino acid 485-493 region was predicted to exist within an alpha-helical region spanning amino acids 485-495 in HCMV-gH (FIG. 6C). Analysis of the space-filling model indicated that the putative epitope region was located on a surface-exposed alpha helix, thus supporting the model that the 5C3 epitope is exposed on the surface of gH (FIGS. 6D and 6E).

To confirm the identity of the 5C3 epitope and determine if 10C10 also targeted this region of the gH protein, a flow cytometry-based binding assay was established using gH mutants constructed by substituting residues within the putative epitope region with alanine. The mutant constructs were then transfected into HEK-293 cells together with gL, and binding by anti-gH antibodies was analyzed with flow cytometry. The validity of the assay was first demonstrated by transfecting wildtype gH, a mutant construct containing two alanine substitutions upstream of the putative epitope region (478-79), and a mutant containing a single alanine substitution in the human anti-gH monoclonal antibody MSL-109 epitope region (aa168) (FIG. 6F). While 10C10, 5C3 and MSL-109 all bound to the wildtype gH or the 478-79 alanine substitution mutant, only 10C10 and 5C3 exhibited binding to the gH 168 mutant. Next, two additional mutants containing consecutive alanine substitutions spanning within the putative epitope region (aa480-486 and 485-492) were generated for binding analysis (FIG. 6G). Remarkably, while MSL-109 bound both of these constructs at levels similar to those observed for the wildtype gH, both 10C10 and 5C3 were unable to bind the 480-486 mutant (FIG. 6G, left column and FIG. 6H). Strikingly, while 5C3 binding was restored in the 485-492 mutant, 10C10 was again unable to bind to the mutant (FIG. 6G, right column and FIG. 6H). The binding studies validate that both 5C3 and 10C10 recognize one or more epitopes, believed to be conformational, within SEQ ID NO: 1.

For a high-resolution picture of the specific residues required for binding by 10C10 or 5C3, sequential alanine substitutions were incorporated between residues 480 and 492, in which two residues at a time were replaced with alanines (FIG. 6I). While MSL-109 and 5C3 bound to all of the 2 amino acid substitution mutants at comparable levels, 10C10 binding was completely abrogated upon disruption of amino acids 484-487, while mutations outside of this region restored wildtype binding levels. The data indicated that the epitopes of both 5C3 and 10C10 are contained within SEQ ID NO: 1. To determine the conservation of this epitope region across HCMV strains, sequence alignment of the gH proteins from HCMV strains isolated from distinct geographic locations was carried out (FIG. 6J). Among 10 distinct HCMV strains, 100% identity was observed in the 10C10/5C3 epitope domain, indicating that the SEQ ID NO: 1 is highly conserved across HCMV strains, thus likely owing to the broadly neutralizing capabilities of 5C3 and 10C10.

TABLE 6 average binding of antibodies to different HCMV gH alanine mutants

| Alanine Mutant | Avg. binding (% of mass) | | |
|---|---|---|---|
| | MSL-109 | | MSL-109 |
| 480-486 | 66 | 3 | 14 |
| 485-492 | 65 | 2 | 49 |
| 478-488 | 100 | 100 | 100 |
| 480-481 | 87 | 70 | 72 |
| 482-483 | 92 | 91 | 85 |
| 484-485 | 86 | 3 | 76 |
| 486-487 | 66 | 2 | 56 |
| 488-489 | 111 | 98 | 113 |
| 490-491 | 89 | 72 | 92 |

11. Genomic Analysis of Anti-HCMV mAbs

Messenger RNA (mRNA) and cDNA was generated from hybridoma cells expressing the monoclonal antibodies using standard techniques. To amplify heavy and light antibody chains, a polymerase chain reaction (PCR) was performed in two rounds using a set of multi-family specific primers for heavy and light variable genes in the first round, followed by sequencing; see Table 1 supra. From the sequence data, a set of specific primers were generated for the variable portion of the antibody gene which included a specific 5' and 3' primer to the VH and JH ends of the heavy chain variable gene and the VL and JL ends of the light chain variable gene. These specific primers also contained restriction enzyme sequences for cloning the PCR product into a plasmid vector. The second round of PCR was performed on the mRNA using the specific set of primers. DNA products from the PCR were isolated using a DNA purification kit and digested with restriction enzymes specific for the sites included in the primers. The heavy and light variable genes were then cloned using standard techniques known in the art into commercial or self-made plasmid vectors containing heavy or light constant genes, respectively, on the 3' end of the cloning site, and a signal sequence derived from a commonly expressed protein on the 5' end of the cloning site. Vectors also contained additional genes and promoters for amplification and selection in bacteria and also genes and promoters for expression and selection of the recombinant antibody in mammalian cells.

12. Examination of Serum from Pregnant Women

Supplementation of serum drawn from pregnant women during the first trimester of pregnancy with mAb 5C3 demonstrated enhanced HCMV neutralizing ability regardless of serostatus (FIG. 14). Neutralization of both fibroblast and epithelial cells by Cytogam® was also augmented by the addition of 5C3 (FIGS. 14B and 14C), further demonstrating the potential utility of passive immunization with anti-gH mAbs.

It will be understood by those of skill in the art that numerous and various modifications can be made without departing from the scope and spirit of the present disclosure. Therefore, it should be understood that various embodiments of the invention described herein are illustrative only and not intended to limit the scope of the invention. All references cited herein are hereby incorporated by reference in their entirety.

What is claimed is:

1. An isolated anti-HCMV antibody, or antigen-binding portion thereof, comprising:
   (a) a heavy chain CDR1 (CDRH1), a heavy chain CDR2 (CDRH2), a heavy chain CDR3 (CDRH3), a light chain CDR1 (CDRL1), a light chain CDR2 (CDRL2), and a light chain CDR3 (CDRL3), wherein:
      (i) CDRH1 comprises SEQ ID NO: 15;
      (ii) CDRH2 comprises SEQ ID NO: 16;
      (iii) CDRH3 comprises SEQ ID NO: 17;
      (iv) CDRL1 comprises SEQ ID NO: 18;
      (v) CDRL2 comprises SEQ ID NO: 19; and
      (vi) CDRL3 comprises SEQ ID NO: 20; or
   (b) a CDRH1, a CDRH2, a CDRH3, a CDRL1, a CDRL2, and a CDRL3, wherein:
      (i) CDRH1 comprises SEQ ID NO: 21;
      (ii) CDRH2 comprises SEQ ID NO: 22;
      (iii) CDRH3 comprises SEQ ID NO: 23;
      (iv) CDRL1 comprises SEQ ID NO: 24;
      (v) CDRL2 comprises SEQ ID NO: 25, and
      (vi) CDRL3 comprises SEQ ID NO: 26; or
   (c) a CDRH1, a CDRH2, a CDRH3, a CDRL1, a CDRL2, and a CDRL3, wherein:
      (i) CDRH1 comprising SEQ ID NO: 27;
      (ii) CDRH2 comprises SEQ ID NO: 28;
      (iii) CDRH3 comprises SEQ ID NO: 29;
      (iv) CDRL1 comprises SEQ ID NO: 30;
      (v) CDRL2 comprises SEQ ID NO: 31; and
      (vi) a CDRL3 comprises SEQ ID NO: 32.

2. The isolated anti-HCMV antibody, or antigen-binding portion thereof, of claim 1 having:
   a) a heavy chain comprising SEQ ID NO: 9 or a sequence consisting essentially of SEQ ID NO: 9 but having at least one conservative substitution, and a light chain comprising SEQ ID NO: 10 or a sequence consisting essentially of SEQ ID NO: 10 but having at least one conservative substitution; or
   b) a heavy chain comprising SEQ ID NO: 11 or a sequence consisting essentially of SEQ ID NO: 11 but having at least one conservative substitution, and a light chain comprising SEQ ID NO: 12 or a sequence consisting essentially of SEQ ID NO: 12 but having at least one conservative substitution; or
   c) a heavy chain comprising SEQ ID NO: 13 or a sequence consisting essentially of SEQ ID NO: 13 but having at least one conservative substitution, and a light chain comprising SEQ ID NO: 14 or a sequence consisting essentially of SEQ ID NO: 14 but having at least one conservative substitution.

3. The isolated anti-HCMV antibody, or antigen-binding portion thereof, of claim 1, wherein the antibody is a monoclonal antibody.

4. The isolated anti-HCMV antibody, or antigen-binding portion thereof, of claim 1, wherein the antibody is a human antibody, a humanized antibody, or a chimeric antibody.

5. A kit for detecting the presence of HCMV, or an antigenic fragment of HCMV thereof, in a sample comprising: (i) the isolated anti-HCMV antibody, or antigen-binding portion thereof, of claim 1, and (ii) a buffer.

6. The kit of claim 5, further comprising a secondary antibody that specifically binds to the anti-HCMV antibody, or antigen-binding portion thereof.

7. A method of detecting the presence of HCMV, or an antigenic fragment thereof, in a sample comprising:
   (i) obtaining a sample containing, or suspecting of containing, HCMV, or an antigenic fragment thereof;
   (ii) contacting the sample with the isolated anti-HCMV antibody, or antigen-binding portion thereof, of claim 1; and
   (iii) detecting the presence of specific binding of the anti-HCMV antibody, or antigen-binding portion thereof, to HCMV, or an antigenic fragment thereof.

8. The method of claim 7, further comprising:
   (iv) quantifying the amount of HCMV, or antigenic fragments thereof, present in the sample.

9. The method of claim 7, wherein the sample is an environmental or a biological sample.

10. A method of treating an HCMV infection in an individual in need thereof comprising:

(i) identifying an individual having, or suspected of having, an HCMV infection; and
(ii) administering to the individual a composition comprising the isolated anti-HCMV antibody, or antigen-binding portion thereof, of claim 1 and a pharmaceutically acceptable carrier or excipient.

11. The method of claim 10, further comprising administering to the individual at least one additional anti-HCMV antibody, or antigen-binding portion thereof.

12. A method of treating an HCMV infection in an individual in need thereof comprising:
(i) identifying an individual having, or suspected of having, an HCMV infection; and
(ii) administering to the individual a composition comprising the isolated anti-HCMV antibody, or antigen-binding portion thereof, of claim 1 and a pharmaceutically acceptable carrier or excipient; and
(iii) administering to the individual at least one additional anti-HCMV antibody, or antigen-binding portion thereof, wherein the at least one additional anti-HCMV antibody, or antigen-binding portion thereof, is an anti-HCMV antibody, or antigen-binding portion thereof, of claim 1.

13. The method of claim 10, further comprising administering to the individual at least one antiviral composition.

14. The method of claim 13, wherein the antiviral composition is selected from the group consisting of ganciclovir, valganciclovir, foscarnet, cidofovir, and combinations thereof.

15. A passive vaccine comprising the isolated anti-HCMV antibody, or antigen-binding portion thereof, of claim 1.

16. A method of preventing an HCMV infection in an individual comprising administering to the individual the passive vaccine of claim 15.

17. A pharmaceutical composition comprising (i) the isolated anti-HCMV antibody, or antigen-binding portion thereof, of claim 1, and (ii) a pharmaceutically acceptable carrier, preservative, or excipient.

18. A nucleic acid sequence encoding the isolated anti-HCMV antibody, or antigen-binding portion thereof, of claim 1.

19. The nucleic acid sequence of claim 18 comprising one of SEQ ID NO: 3, SEQ ID NO: 4, SEQ ID NO: 5, SEQ ID NO: 6, SEQ ID NO: 7, and SEQ ID NO: 8, a sequence consisting essentially of SEQ ID NO: 3, SEQ ID NO: 4, SEQ ID NO: 5, SEQ ID NO: 6, SEQ ID NO: 7, and SEQ ID NO: 8 but having conservative substitutions, or a codon-optimized sequence encoding the same antibody or antigen-binding portion thereof.

20. A vector or vector system comprising at least one nucleic acid of claim 18.

21. An isolated cell transformed with the vector or vector system of claim 20.

22. The isolated cell of claim 21, wherein the isolated cell is a bacterial cell, a yeast cell, or a mammalian cell.

23. A method of making recombinant anti-HCMV antibody, or antigen-binding fragment thereof, comprising:
(i) providing a cell of claim 21;
(ii) expressing at least one nucleic acid sequence in the vector or vector system of the cell to create at least one of a heavy chain, a light chain, or combinations thereof; and
(iii) collecting a formed anti-HCMV antibody, or antigen-binding fragment, thereof.

\* \* \* \* \*

SEQUENCE LISTING

```
<160> NUMBER OF SEQ ID NOS: 64

<210> SEQ ID NO 1
<211> LENGTH: 15
<212> TYPE: PRT
<213> ORGANISM: Human cytomegalovirus

<400> SEQUENCE: 1

Val His Thr Thr Glu Arg Arg Glu Ile Phe Ile Val Glu Thr Gly
1               5                   10                  15

<210> SEQ ID NO 2
<211> LENGTH: 743
<212> TYPE: PRT
<213> ORGANISM: Human cytomegalovirus

<400> SEQUENCE: 2

Met Arg Pro Gly Leu Pro Phe Tyr Leu Thr Val Phe Ala Val Tyr Leu
1               5                   10                  15

Leu Ser His Leu Pro Ser Gln Arg Tyr Gly Ala Asp Ala Ala Ser Glu
            20                  25                  30

Ala Leu Asp Pro His Ala Phe His Leu Leu Leu Asn Thr Tyr Gly Arg
        35                  40                  45

Pro Ile Arg Phe Leu Arg Glu Asn Thr Thr Gln Cys Thr Tyr Asn Ser
    50                  55                  60

Ser Leu Arg Asn Ser Thr Val Val Arg Glu Asn Ala Ile Ser Phe Asn
65                  70                  75                  80
```

-continued

```
Phe Phe Gln Ser Tyr Asn Gln Tyr Tyr Val Phe His Met Pro Arg Cys
                 85                  90                  95
Leu Phe Ala Gly Pro Leu Ala Glu Gln Phe Leu Asn Gln Val Asp Leu
            100                 105                 110
Thr Glu Thr Leu Glu Arg Tyr Gln Gln Arg Leu Asn Thr Tyr Ala Leu
        115                 120                 125
Val Ser Lys Asp Leu Ala Ser Tyr Arg Ser Phe Ser Gln Gln Leu Lys
    130                 135                 140
Ala Gln Asp Ser Leu Gly Gln Gln Pro Thr Thr Val Pro Pro Pro Ile
145                 150                 155                 160
Asp Leu Ser Ile Pro His Val Trp Met Pro Pro Gln Thr Thr Pro His
                165                 170                 175
Asp Trp Lys Gly Ser His Thr Thr Ser Gly Leu His Arg Pro His Phe
            180                 185                 190
Asn Gln Thr Cys Ile Leu Phe Asp Gly His Asp Leu Leu Phe Ser Thr
        195                 200                 205
Val Thr Pro Cys Leu His Gln Gly Phe Tyr Leu Met Asp Glu Leu Arg
    210                 215                 220
Tyr Val Lys Ile Thr Leu Thr Glu Asp Phe Phe Val Val Thr Val Ser
225                 230                 235                 240
Ile Asp Asp Asp Thr Pro Met Leu Leu Ile Phe Gly His Leu Pro Arg
                245                 250                 255
Val Leu Phe Lys Ala Pro Tyr Gln Arg Asp Asn Phe Ile Leu Arg Gln
            260                 265                 270
Thr Glu Lys His Glu Leu Leu Val Leu Val Lys Lys Thr Gln Leu Asn
        275                 280                 285
Arg His Ser Tyr Leu Lys Asp Ser Asp Phe Leu Asp Ala Ala Leu Asp
    290                 295                 300
Phe Asn Tyr Leu Asp Leu Ser Ala Leu Leu Arg Asn Ser Phe His Arg
305                 310                 315                 320
Tyr Ala Val Asp Val Leu Lys Ser Gly Arg Cys Gln Met Leu Asp Arg
                325                 330                 335
Arg Thr Val Glu Met Ala Phe Ala Tyr Ala Leu Ala Leu Phe Ala Ala
            340                 345                 350
Ala Arg Gln Glu Glu Ala Gly Thr Glu Ile Ser Ile Pro Arg Ala Leu
        355                 360                 365
Asp Arg Gln Ala Ala Leu Leu Gln Ile Gln Glu Phe Met Ile Thr Cys
    370                 375                 380
Leu Ser Gln Thr Pro Pro Arg Thr Thr Leu Leu Leu Tyr Pro Thr Ala
385                 390                 395                 400
Val Asp Leu Ala Lys Arg Ala Leu Trp Thr Pro Asp Gln Ile Thr Asp
                405                 410                 415
Ile Thr Ser Leu Val Arg Leu Val Tyr Ile Leu Ser Lys Gln Asn Gln
            420                 425                 430
Gln His Leu Ile Pro Gln Trp Ala Leu Arg Gln Ile Ala Asp Phe Ala
        435                 440                 445
Leu Gln Leu His Lys Thr His Leu Ala Ser Phe Leu Ser Ala Phe Ala
    450                 455                 460
Arg Gln Glu Leu Tyr Leu Met Gly Ser Leu Val His Ser Met Leu Val
465                 470                 475                 480
His Thr Thr Glu Arg Arg Glu Ile Phe Ile Val Glu Thr Gly Leu Cys
                485                 490                 495
Ser Leu Ala Glu Leu Ser His Phe Thr Gln Leu Leu Ala His Pro His
```

|   |   |   | 500 |   |   |   | 505 |   |   |   | 510 |
|---|---|---|---|---|---|---|---|---|---|---|---|

His Glu Tyr Leu Ser Asp Leu Tyr Thr Pro Cys Ser Ser Ser Gly Arg
           515                   520                   525

Arg Asp His Ser Leu Glu Arg Leu Thr Arg Leu Phe Pro Asp Ala Thr
      530                   535                   540

Val Pro Ala Thr Val Pro Ala Ala Leu Ser Ile Leu Ser Thr Met Gln
545                   550                   555                   560

Pro Ser Thr Leu Glu Thr Phe Pro Asp Leu Phe Cys Leu Pro Leu Gly
           565                   570                   575

Glu Ser Phe Ser Ala Leu Thr Val Ser Glu His Val Ser Tyr Val Val
           580                   585                   590

Thr Asn Gln Tyr Leu Ile Lys Gly Ile Ser Tyr Pro Val Ser Thr Thr
      595                   600                   605

Val Val Gly Gln Ser Leu Ile Ile Thr Gln Thr Asp Ser Gln Ser Lys
           610                   615                   620

Cys Glu Leu Thr Arg Asn Met His Thr His Ser Ile Thr Ala Ala
625                   630                   635                   640

Leu Asn Ile Ser Leu Glu Asn Cys Ala Phe Cys Gln Ser Ala Leu Leu
           645                   650                   655

Glu Tyr Asp Asp Thr Gln Gly Val Ile Asn Ile Met Tyr Met His Asp
           660                   665                   670

Ser Asp Asp Val Leu Phe Ala Leu Asp Pro Tyr Asn Glu Val Val Val
      675                   680                   685

Ser Ser Pro Arg Thr His Tyr Leu Met Leu Leu Lys Asn Gly Thr Val
           690                   695                   700

Leu Glu Val Thr Asp Val Val Val Asp Ala Thr Asp Ser Arg Leu Leu
705                   710                   715                   720

Met Met Ser Val Tyr Ala Leu Ser Ala Ile Ile Gly Ile Tyr Leu Leu
           725                   730                   735

Tyr Arg Met Leu Lys Thr Cys
           740

<210> SEQ ID NO 3
<211> LENGTH: 348
<212> TYPE: DNA
<213> ORGANISM: Artificial
<220> FEATURE:
<223> OTHER INFORMATION: Synthetic

<400> SEQUENCE: 3
caggtccaac tgcagcagcc tggggctgag ctggtgaggc ctggggcttc agtgaagctg      60
tcctgcaagg cttctggcta caccttcacc acttactgga tgaactgggt gaagcagagg     120
cctggacaag gccttgaatg gattggtatg attgatcctt cagacagtga aactcactac     180
aatcaaatgt tcaaggacaa ggccacattg actgtggaca tcctccag cacagcctac      240 atgcaactca gcagtctgac atctgaggat tctgcggtct attactgtgc aagaggccgg     300
tcctggtttg tttattgggg ccaagggact ctggtcactg tctctagc                 348

<210> SEQ ID NO 4
<211> LENGTH: 336
<212> TYPE: DNA
<213> ORGANISM: Artificial
<220> FEATURE:
<223> OTHER INFORMATION: Synthetic

<400> SEQUENCE: 4

```
gacattgtgc tgacacagtc tcctgcttcc ttagctgttt ctctgggca gagggccacc      60 atctcatgca gggccagcaa aagtgtcagt tcatctggct atagttatgt gcactggtac     120
cagcagaaac cagggcaacc acccaaactc ctcatctatc ttgcatccaa cctagaatct    180
ggggtccctg ccaggttcag tggcagtggg tctgggacag acttcaccct caacatccat    240
tctgtggagg aggaggatgc tgcaacctat tactgtcagc acaatagggg gcttccgtac    300
actttcggag gggggaccaa gctggaaata aaacgg                              336

<210> SEQ ID NO 5
<211> LENGTH: 360
<212> TYPE: DNA
<213> ORGANISM: Artificial
<220> FEATURE:
<223> OTHER INFORMATION: Synthetic

<400> SEQUENCE: 5
gatgtgcagc ttcaggagtc gggacctggc ctggtgaaac cttctcagtc tctgtccctc     60
acctgcactg tcactggcta ctcaatcacc agtgattatg cctggaactg gatccggcag    120
tttccaggaa acaaactgga gtggatgggc tacataagct acagtggtag cactagctac    180
aacccatctc tcaaaagtcg aatctctatc actcgagaca catccaagaa ccagttcttc    240
ctgcagttga attctgtgac tactgaggac acagccacat attactgtgc aagacggagg    300
gattacggag aggactactt tgactactgg ggccaaggca ccactctcac agtctccagc    360

<210> SEQ ID NO 6
<211> LENGTH: 342
<212> TYPE: DNA
<213> ORGANISM: Artificial
<220> FEATURE:
<223> OTHER INFORMATION: Synthetic

<400> SEQUENCE: 6
gacattgtga tgacacagtc tccatcctcc ctgagtgtgt cagcaggaga gaaggtcact     60
atgagctgca gtccagtca gagtctgtta acagtggaa atcaaaggaa ctacttggcc     120
tggtaccagc agaaaccagg gcagcctcct aaactgttaa tctacggggc atccactagg    180
gaatctgggg tccctgatcg cttcacaggc agtggatctg gaaccgattt cactcttacc    240
atcagcagtg tgcaggctga agacctggca gtttattatt gtcagaatga ttatagttat    300
ccattcacgt tcggctcggg gacaaagttg gaaataaaac gg                       342

<210> SEQ ID NO 7
<211> LENGTH: 357
<212> TYPE: DNA
<213> ORGANISM: Artificial
<220> FEATURE:
<223> OTHER INFORMATION: Synthetic

<400> SEQUENCE: 7
gaggtccagc ttcagcagtc aggacctgag ctggtgaagc ctggagtttc aatgaggata     60
tcctgcaagg cttctggttt ctcattcact gactacacca tgaactgggt gaaacagagc    120
catagaaaga accttgagtg gattggactt gttaatcctt acaatggtgg tactagccac    180
aacccgaact caagggcaa ggccacatta actgtagaca gtcatccag cacagcctac     240 atggaactcc tcagtctgac atctgaggac tctgcagtct attactgtgc aagaagggg    300 cgacgcgact atgctttgga ctactggggt cagggaacct cagtcaccgt ctccagc       357
```

```
<210> SEQ ID NO 8
<211> LENGTH: 324
<212> TYPE: DNA
<213> ORGANISM: Artificial
<220> FEATURE:
<223> OTHER INFORMATION: Synthetic

<400> SEQUENCE: 8
gatattgtgc taactcagtc tccagtcacc ctgtctgtga ctccaggaga tagcgtcagt      60
ctttcctgca gggccagcca agtgttagt aacaacctac actggtatca acaaaaatca     120
catgagtctc caaggcttct cataaagtat gcttcccagt ccatctctgg atcccctcc     180 aggttcagag cagtggatc aggacagat ttcactctca gtatcatcag tgtggagact     240
gaagattttg gaatgtattt ctgtcaacag agtaacatct ggcctcacac gttcggtgct    300
gggaccaagc tggagctgaa acgg                                            324

<210> SEQ ID NO 9
<211> LENGTH: 116
<212> TYPE: PRT
<213> ORGANISM: Artificial
<220> FEATURE:
<223> OTHER INFORMATION: Synthetic

<400> SEQUENCE: 9

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Thr Tyr
                20                  25                  30

Trp Met Asn Trp Val Lys Gln Arg Pro Gly Gln Gly Leu Glu Trp Ile
            35                  40                  45

Gly Met Ile Asp Pro Ser Asp Ser Glu Thr His Tyr Asn Gln Met Phe
        50                  55                  60

Lys Asp Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Arg Ser Trp Phe Val Tyr Trp Gly Gln Gly Thr Leu Val
            100                 105                 110

Thr Val Ser Ser
        115

<210> SEQ ID NO 10
<211> LENGTH: 112
<212> TYPE: PRT
<213> ORGANISM: Artificial
<220> FEATURE:
<223> OTHER INFORMATION: Synthetic

<400> SEQUENCE: 10

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Ser Ser
                20                  25                  30

Gly Tyr Ser Tyr Val His Trp Tyr Gln Gln Lys Pro Gly Gln Pro Pro
            35                  40                  45

Lys Leu Leu Ile Tyr Leu Ala Ser Asn Leu Glu Ser Gly Val Pro Ala
        50                  55                  60

Arg Phe Ser Gly Ser Gly Ser Gly Thr Asp Phe Thr Leu Asn Ile His
65                  70                  75                  80
```

Ser Val Glu Glu Glu Asp Ala Ala Thr Tyr Tyr Cys Gln His Asn Arg
            85                  90                  95

Glu Leu Pro Tyr Thr Phe Gly Gly Gly Thr Lys Leu Glu Ile Lys Arg
            100                 105                 110

<210> SEQ ID NO 11
<211> LENGTH: 120
<212> TYPE: PRT
<213> ORGANISM: Artificial
<220> FEATURE:
<223> OTHER INFORMATION: Synthetic

<400> SEQUENCE: 11

Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
            35                  40                  45

Met Gly Tyr Ile Ser Tyr Ser Gly Ser Thr Ser Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
            85                  90                  95

Ala Arg Arg Arg Asp Tyr Gly Glu Asp Tyr Phe Asp Tyr Trp Gly Gln
            100                 105                 110

Gly Thr Thr Leu Thr Val Ser Ser
            115                 120

<210> SEQ ID NO 12
<211> LENGTH: 114
<212> TYPE: PRT
<213> ORGANISM: Artificial
<220> FEATURE:
<223> OTHER INFORMATION: Synthetic

<400> SEQUENCE: 12

Asp Ile Val Met Thr Gln Ser Pro Ser Ser Leu Ser Val Ser Ala Gly
1               5                   10                  15

Glu Lys Val Thr Met Ser Cys Lys Ser Ser Gln Ser Leu Leu Asn Ser
            20                  25                  30

Gly Asn Gln Arg Asn Tyr Leu Ala Trp Tyr Gln Gln Lys Pro Gly Gln
            35                  40                  45

Pro Pro Lys Leu Leu Ile Tyr Gly Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
            85                  90                  95

Asp Tyr Ser Tyr Pro Phe Thr Phe Gly Ser Gly Thr Lys Leu Glu Ile
            100                 105                 110

Lys Arg

<210> SEQ ID NO 13
<211> LENGTH: 119
<212> TYPE: PRT
<213> ORGANISM: Artificial

<220> FEATURE:
<223> OTHER INFORMATION: Synthetic

<400> SEQUENCE: 13

Glu Val Gln Leu Gln Gln Ser Gly Pro Glu Leu Val Lys Pro Gly Val
1               5                   10                  15

Ser Met Arg Ile Ser Cys Lys Ala Ser Gly Phe Ser Phe Thr Asp Tyr
            20                  25                  30

Thr Met Asn Trp Val Lys Gln Ser His Arg Lys Asn Leu Glu Trp Ile
        35                  40                  45

Gly Leu Val Asn Pro Tyr Asn Gly Gly Thr Ser His Asn Pro Asn Phe
50                  55                  60

Lys Gly Lys Ala Thr Leu Thr Val Asp Lys Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Arg Gly Arg Arg Asp Tyr Ala Leu Asp Tyr Trp Gly Gln Gly
            100                 105                 110

Thr Ser Val Thr Val Ser Ser
        115

<210> SEQ ID NO 14
<211> LENGTH: 108
<212> TYPE: PRT
<213> ORGANISM: Artificial
<220> FEATURE:
<223> OTHER INFORMATION: Synthetic

<400> SEQUENCE: 14

Asp Ile Val Leu Thr Gln Ser Pro Val Thr Leu Ser Val Thr Pro Gly
1               5                   10                  15

Asp Ser Val Ser Leu Ser Cys Arg Ala Ser Gln Ser Val Ser Asn Asn
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Arg Gly
50                  55                  60

Ser Gly Ser Gly Thr Asp Phe Thr Leu Ser Ile Ile Ser Val Glu Thr
65                  70                  75                  80

Glu Asp Phe Gly Met Tyr Phe Cys Gln Gln Ser Asn Ile Trp Pro His
                85                  90                  95

Thr Phe Gly Ala Gly Thr Lys Leu Glu Leu Lys Arg
            100                 105

<210> SEQ ID NO 15
<211> LENGTH: 8
<212> TYPE: PRT
<213> ORGANISM: Artificial
<220> FEATURE:
<223> OTHER INFORMATION: Synthetic

<400> SEQUENCE: 15

Gly Tyr Thr Phe Thr Thr Tyr Trp
1               5

<210> SEQ ID NO 16
<211> LENGTH: 8
<212> TYPE: PRT
<213> ORGANISM: Artificial
<220> FEATURE:

```
<223> OTHER INFORMATION: Synthetic

<400> SEQUENCE: 16

Ile Asp Pro Ser Asp Ser Glu Thr
1               5

<210> SEQ ID NO 17
<211> LENGTH: 9
<212> TYPE: PRT
<213> ORGANISM: Artificial
<220> FEATURE:
<223> OTHER INFORMATION: Synthetic

<400> SEQUENCE: 17

Ala Arg Gly Arg Ser Trp Phe Val Tyr
1               5

<210> SEQ ID NO 18
<211> LENGTH: 10
<212> TYPE: PRT
<213> ORGANISM: Artificial
<220> FEATURE:
<223> OTHER INFORMATION: Synthetic

<400> SEQUENCE: 18

Lys Ser Val Ser Ser Gly Tyr Ser Tyr
1               5                   10

<210> SEQ ID NO 19
<211> LENGTH: 3
<212> TYPE: PRT
<213> ORGANISM: Artificial
<220> FEATURE:
<223> OTHER INFORMATION: Synthetic

<400> SEQUENCE: 19

Leu Ala Ser
1

<210> SEQ ID NO 20
<211> LENGTH: 9
<212> TYPE: PRT
<213> ORGANISM: Artificial
<220> FEATURE:
<223> OTHER INFORMATION: Synthetic

<400> SEQUENCE: 20

Gln His Asn Arg Glu Leu Pro Tyr Thr
1               5

<210> SEQ ID NO 21
<211> LENGTH: 9
<212> TYPE: PRT
<213> ORGANISM: Artificial
<220> FEATURE:
<223> OTHER INFORMATION: Synthetic

<400> SEQUENCE: 21

Gly Tyr Ser Ile Thr Ser Asp Tyr Ala
1               5

<210> SEQ ID NO 22
<211> LENGTH: 7
<212> TYPE: PRT
<213> ORGANISM: Artificial
<220> FEATURE:
<223> OTHER INFORMATION: Synthetic
```

```
<400> SEQUENCE: 22

Ile Ser Tyr Ser Gly Ser Thr
1               5

<210> SEQ ID NO 23
<211> LENGTH: 13
<212> TYPE: PRT
<213> ORGANISM: Artificial
<220> FEATURE:
<223> OTHER INFORMATION: Synthetic

<400> SEQUENCE: 23

Ala Arg Arg Arg Asp Tyr Gly Glu Asp Tyr Phe Asp Tyr
1               5                   10

<210> SEQ ID NO 24
<211> LENGTH: 12
<212> TYPE: PRT
<213> ORGANISM: Artificial
<220> FEATURE:
<223> OTHER INFORMATION: Synthetic

<400> SEQUENCE: 24

Gln Ser Leu Leu Asn Ser Gly Asn Gln Arg Asn Tyr
1               5                   10

<210> SEQ ID NO 25
<211> LENGTH: 3
<212> TYPE: PRT
<213> ORGANISM: Artificial
<220> FEATURE:
<223> OTHER INFORMATION: Synthetic

<400> SEQUENCE: 25

Gly Ala Ser
1

<210> SEQ ID NO 26
<211> LENGTH: 9
<212> TYPE: PRT
<213> ORGANISM: Artificial
<220> FEATURE:
<223> OTHER INFORMATION: Synthetic

<400> SEQUENCE: 26

Gln Asn Asp Tyr Ser Tyr Pro Phe Thr
1               5

<210> SEQ ID NO 27
<211> LENGTH: 8
<212> TYPE: PRT
<213> ORGANISM: Artificial
<220> FEATURE:
<223> OTHER INFORMATION: Synthetic

<400> SEQUENCE: 27

Gly Phe Ser Phe Thr Asp Tyr Thr
1               5

<210> SEQ ID NO 28
<211> LENGTH: 8
<212> TYPE: PRT
<213> ORGANISM: Artificial
<220> FEATURE:
<223> OTHER INFORMATION: Synthetic
```

```
<400> SEQUENCE: 28

Val Asn Pro Tyr Asn Gly Gly Thr
1               5

<210> SEQ ID NO 29
<211> LENGTH: 12
<212> TYPE: PRT
<213> ORGANISM: Artificial
<220> FEATURE:
<223> OTHER INFORMATION: Synthetic

<400> SEQUENCE: 29

Ala Arg Arg Gly Arg Arg Asp Tyr Ala Leu Asp Tyr
1               5                   10

<210> SEQ ID NO 30
<211> LENGTH: 6
<212> TYPE: PRT
<213> ORGANISM: Artificial
<220> FEATURE:
<223> OTHER INFORMATION: Synthetic

<400> SEQUENCE: 30

Gln Ser Val Ser Asn Asn
1               5

<210> SEQ ID NO 31
<211> LENGTH: 3
<212> TYPE: PRT
<213> ORGANISM: Artificial
<220> FEATURE:
<223> OTHER INFORMATION: Synthetic

<400> SEQUENCE: 31

Tyr Ala Ser
1

<210> SEQ ID NO 32
<211> LENGTH: 9
<212> TYPE: PRT
<213> ORGANISM: Artificial
<220> FEATURE:
<223> OTHER INFORMATION: Synthetic

<400> SEQUENCE: 32

Gln Gln Ser Asn Ile Trp Pro His Thr
1               5

<210> SEQ ID NO 33
<211> LENGTH: 8
<212> TYPE: PRT
<213> ORGANISM: Human cytomegalovirus

<400> SEQUENCE: 33

Arg Glu Ile Phe Ile Val Glu Thr
1               5

<210> SEQ ID NO 34
<211> LENGTH: 9
<212> TYPE: PRT
<213> ORGANISM: Human cytomegalovirus

<400> SEQUENCE: 34

Arg Arg Glu Ile Phe Ile Val Glu Thr
1               5
```

```
<210> SEQ ID NO 35
<211> LENGTH: 7
<212> TYPE: PRT
<213> ORGANISM: Human cytomegalovirus

<400> SEQUENCE: 35

Thr Glu Arg Arg Glu Ile Phe
1               5

<210> SEQ ID NO 36
<211> LENGTH: 7
<212> TYPE: PRT
<213> ORGANISM: Human cytomegalovirus

<400> SEQUENCE: 36

Glu Arg Arg Glu Ile Phe Ile
1               5

<210> SEQ ID NO 37
<211> LENGTH: 7
<212> TYPE: PRT
<213> ORGANISM: Human cytomegalovirus

<400> SEQUENCE: 37

Arg Arg Glu Ile Phe Ile Val
1               5

<210> SEQ ID NO 38
<211> LENGTH: 7
<212> TYPE: PRT
<213> ORGANISM: Human cytomegalovirus

<400> SEQUENCE: 38

Arg Glu Ile Phe Ile Val Glu
1               5

<210> SEQ ID NO 39
<211> LENGTH: 7
<212> TYPE: PRT
<213> ORGANISM: Human cytomegalovirus

<400> SEQUENCE: 39

Glu Ile Phe Ile Val Glu Thr
1               5

<210> SEQ ID NO 40
<211> LENGTH: 7
<212> TYPE: PRT
<213> ORGANISM: Human cytomegalovirus

<400> SEQUENCE: 40

Ile Phe Ile Val Glu Thr Gly
1               5

<210> SEQ ID NO 41
<211> LENGTH: 10
<212> TYPE: PRT
<213> ORGANISM: Human cytomegalovirus

<400> SEQUENCE: 41

His Thr Thr Glu Arg Arg Glu Ile Phe Ile
1               5                   10

<210> SEQ ID NO 42
```

```
<210> SEQ ID NO 42
<211> LENGTH: 10
<212> TYPE: PRT
<213> ORGANISM: Human cytomegalovirus

<400> SEQUENCE: 42

Thr Thr Glu Arg Arg Glu Ile Phe Ile Val
1               5                   10

<210> SEQ ID NO 43
<211> LENGTH: 10
<212> TYPE: PRT
<213> ORGANISM: Human cytomegalovirus

<400> SEQUENCE: 43

Thr Glu Arg Arg Glu Ile Phe Ile Val Glu
1               5                   10

<210> SEQ ID NO 44
<211> LENGTH: 10
<212> TYPE: PRT
<213> ORGANISM: Human cytomegalovirus

<400> SEQUENCE: 44

Glu Arg Arg Glu Ile Phe Ile Val Glu Thr
1               5                   10

<210> SEQ ID NO 45
<211> LENGTH: 10
<212> TYPE: PRT
<213> ORGANISM: Human cytomegalovirus

<400> SEQUENCE: 45

Arg Arg Glu Ile Phe Ile Val Glu Thr Gly
1               5                   10

<210> SEQ ID NO 46
<211> LENGTH: 10
<212> TYPE: PRT
<213> ORGANISM: Human cytomegalovirus

<400> SEQUENCE: 46

Arg Glu Ile Phe Ile Val Glu Thr Gly Leu
1               5                   10

<210> SEQ ID NO 47
<211> LENGTH: 13
<212> TYPE: PRT
<213> ORGANISM: Human cytomegalovirus

<400> SEQUENCE: 47

Met Leu Val His Thr Thr Glu Arg Arg Glu Ile Phe Ile
1               5                   10

<210> SEQ ID NO 48
<211> LENGTH: 13
<212> TYPE: PRT
<213> ORGANISM: Human cytomegalovirus

<400> SEQUENCE: 48

Leu Val His Thr Thr Glu Arg Arg Glu Ile Phe Ile Val
1               5                   10

<210> SEQ ID NO 49
<211> LENGTH: 13
<212> TYPE: PRT
```

<213> ORGANISM: Human cytomegalovirus

<400> SEQUENCE: 49

Val His Thr Thr Glu Arg Arg Glu Ile Phe Ile Val Glu
1               5                   10

<210> SEQ ID NO 50
<211> LENGTH: 13
<212> TYPE: PRT
<213> ORGANISM: Human cytomegalovirus

<400> SEQUENCE: 50

His Thr Thr Glu Arg Arg Glu Ile Phe Ile Val Glu Thr
1               5                   10

<210> SEQ ID NO 51
<211> LENGTH: 13
<212> TYPE: PRT
<213> ORGANISM: Human cytomegalovirus

<400> SEQUENCE: 51

Thr Thr Glu Arg Arg Glu Ile Phe Ile Val Glu Thr Gly
1               5                   10

<210> SEQ ID NO 52
<211> LENGTH: 13
<212> TYPE: PRT
<213> ORGANISM: Human cytomegalovirus

<400> SEQUENCE: 52

Thr Glu Arg Arg Glu Ile Phe Ile Val Glu Thr Gly Leu
1               5                   10

<210> SEQ ID NO 53
<211> LENGTH: 13
<212> TYPE: PRT
<213> ORGANISM: Human cytomegalovirus

<400> SEQUENCE: 53

Glu Arg Arg Glu Ile Phe Ile Val Glu Thr Gly Leu Cys
1               5                   10

<210> SEQ ID NO 54
<211> LENGTH: 13
<212> TYPE: PRT
<213> ORGANISM: Human cytomegalovirus

<400> SEQUENCE: 54

Arg Arg Glu Ile Phe Ile Val Glu Thr Gly Leu Cys Ser
1               5                   10

<210> SEQ ID NO 55
<211> LENGTH: 13
<212> TYPE: PRT
<213> ORGANISM: Human cytomegalovirus

<400> SEQUENCE: 55

Arg Glu Ile Phe Ile Val Glu Thr Gly Leu Cys Ser Leu
1               5                   10

<210> SEQ ID NO 56
<211> LENGTH: 17
<212> TYPE: PRT
<213> ORGANISM: Human cytomegalovirus

<400> SEQUENCE: 56

Met Leu Val His Thr Thr Glu Arg Arg Glu Ile Phe Ile Val Glu Thr
1               5                   10                  15

Gly

<210> SEQ ID NO 57
<211> LENGTH: 19
<212> TYPE: PRT
<213> ORGANISM: Human cytomegalovirus

<400> SEQUENCE: 57

Met Leu Val His Thr Thr Glu Arg Arg Glu Ile Phe Ile Val Glu Thr
1               5                   10                  15

Gly Leu Cys

<210> SEQ ID NO 58
<211> LENGTH: 12
<212> TYPE: PRT
<213> ORGANISM: Human cytomegalovirus

<400> SEQUENCE: 58

Thr Glu Arg Arg Glu Ile Phe Ile Val Glu Thr Gly
1               5                   10

<210> SEQ ID NO 59
<211> LENGTH: 6
<212> TYPE: PRT
<213> ORGANISM: Artificial Sequence
<220> FEATURE:
<223> OTHER INFORMATION: Synthetic

<400> SEQUENCE: 59

His Ser Ala Ala Val His
1               5

<210> SEQ ID NO 60
<211> LENGTH: 5
<212> TYPE: PRT
<213> ORGANISM: Artificial Sequence
<220> FEATURE:
<223> OTHER INFORMATION: Synthetic

<400> SEQUENCE: 60

His Val Ala Met Pro
1               5

<210> SEQ ID NO 61
<211> LENGTH: 11
<212> TYPE: PRT
<213> ORGANISM: Artificial Sequence
<220> FEATURE:
<223> OTHER INFORMATION: Synthetic

<400> SEQUENCE: 61

Met Leu Ala Ala Ala Ala Ala Ala Ala Glu Ile
1               5                   10

<210> SEQ ID NO 62
<211> LENGTH: 12
<212> TYPE: PRT
<213> ORGANISM: Artificial Sequence
<220> FEATURE:
<223> OTHER INFORMATION: Synthetic

<400> SEQUENCE: 62

```
Thr Glu Ala Ala Ala Ala Ala Ala Ala Thr Gly
1               5                   10

<210> SEQ ID NO 63
<211> LENGTH: 15
<212> TYPE: PRT
<213> ORGANISM: Human cytomegalovirus

<400> SEQUENCE: 63

Met Leu Val His Thr Thr Glu Arg Arg Glu Ile Phe Ile Val Glu
1               5                   10                  15

<210> SEQ ID NO 64
<211> LENGTH: 20
<212> TYPE: PRT
<213> ORGANISM: Human cytomegalovirus

<400> SEQUENCE: 64

His Thr Thr Glu Arg Arg Glu Ile Phe Ile Val Glu Thr Gly Leu Cys
1               5                   10                  15

Ser Leu Ala Glu
            20
```